United States Patent [19]

Belley et al.

[11] Patent Number: 5,266,568
[45] Date of Patent: Nov. 30, 1993

[54] HYDROXYALKYLQUINOLINE ETHER ACIDS AS LEUKOTRIENE ANTAGONISTS

[75] Inventors: Michel L. Belley, Pierrefonds; Yves LeBlanc, Kirkland; Marc Labelle, Ville d'Ile Perrot, all of Canada

[73] Assignee: Merck Frosst Canada, Inc., Kirkland, Canada

[21] Appl. No.: 774,403

[22] Filed: Oct. 10, 1991

Related U.S. Application Data

[63] Continuation-in-part of Ser. No. 596,885, Oct. 12, 1990, abandoned.

[51] Int. Cl.$^5$ .................. A61K 31/54; A61K 31/47; C07D 215/12
[52] U.S. Cl. .................. 514/228.2; 514/235.2; 514/311; 514/314; 544/62; 544/121; 544/128; 546/167; 546/171; 546/172; 546/174
[58] Field of Search ............ 546/174, 167, 171, 172; 544/62, 121, 128; 514/311, 228.2, 235.2, 314

[56] References Cited

U.S. PATENT DOCUMENTS

| | | | |
|---|---|---|---|
| 4,920,130 | 4/1990 | Haang et al. | 546/174 |
| 4,929,626 | 5/1990 | Mohrs et al. | 546/174 |
| 4,962,203 | 10/1990 | Young et al. | 546/174 |

FOREIGN PATENT DOCUMENTS

| | | |
|---|---|---|
| 233763 | 2/1986 | European Pat. Off. |
| 0315399 | 5/1989 | European Pat. Off. |
| 0348155 | 12/1989 | European Pat. Off. |
| 0349062 | 1/1990 | European Pat. Off. |
| 0399818 | 11/1990 | European Pat. Off. |
| 219249 | 2/1986 | New Zealand |
| 89/04303 | 3/1989 | World Int. Prop. O. |

*Primary Examiner*—C. Warren Ivy
*Assistant Examiner*—Raymond Covington
*Attorney, Agent, or Firm*—Mark R. Daniel; Joseph F. DiPrima

[57] ABSTRACT

Compounds having the formula I:

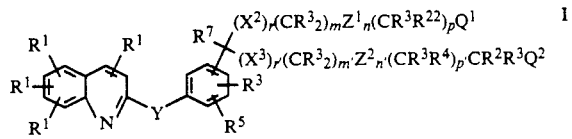

are leukotriene antagonists and inhibitors of leukotriene biosynthesis. These compounds are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection.

19 Claims, No Drawings

HYDROXYALKYLQUINOLINE ETHER ACIDS AS LEUKOTRIENE ANTAGONISTS

CROSS-REFERENCE

This is a continuation-in-part of U.S. Ser. No. 596,885, Oct. 12, 1990, now abandoned.

BACKGROUND OF THE INVENTION

The leukotrienes constitute a group of locally acting hormones, produced in living systems from arachidonic acid. The major leukotrienes are Leukotriene B$_4$ (LTB$_4$), LTC$_4$, LTD$_4$ and LTE$_4$. The biosynthesis of these leukotrienes begins with the action of the enzyme 5-lipoxygenase on arachidonic acid to produce the epoxide known as Leukotriene A$_4$ (LTA$_4$), which is converted to the other leukotrienes by subsequent enzymatic steps. Further details of the biosynthesis as well as the metabolism of the leukotrienes are to be found in *Leukotrienes and Lipoxygenases*, ed. J. Rokach, Elsevier, Amsterdam (1989). The actions of the leukotrienes in living systems and their contribution to various diseases states are also discussed in the book by Rokach.

The art describes certain quinoline-containing compounds as having activity as antagonists of the actions of the leukotrienes. Thus, EP 318,093 (Merck) describes compounds of structure A. Structure B is disclosed in EP 315,399 (Rorer). Structures C and D are described in EP 348,155 (Rorer) and WO 89/04303 (Rorer).

SUMMARY OF THE INVENTION

The present invention relates to hydroxyalkylquinoline ether acids having activity as leukotriene antagonists, to methods for their preparation, and to methods and pharmaceutical formulations for using these compounds in mammals (especially humans).

Because of their activity as leukotriene antagonists, the compounds of the present invention are useful as anti-asthmatic, anti-allergic, anti-inflammatory, and cytoprotective agents. They are also useful in treating angina, cerebral spasm, glomerular nephritis, hepatitis, endotoxemia, uveities, and allograft rejection.

DETAILED DESCRIPTION OF THE INVENTION

The compounds of this invention are best realized by Formula I:

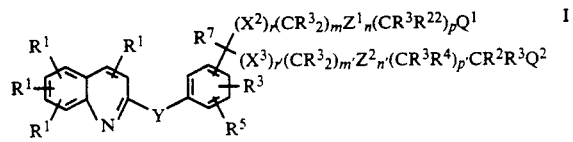

wherein:

R$^1$ is H, halogen, —CF$_3$, —CN, —NO$_2$ or N$_3$;

R$^2$ is lower alkyl, lower alkenyl, lower alkynyl, —CF$_3$, —CH$_2$F, —CHF$_2$, CH$_2$CF$_3$, substituted or unsubstituted phenyl, substituted or unsubstituted benzyl,

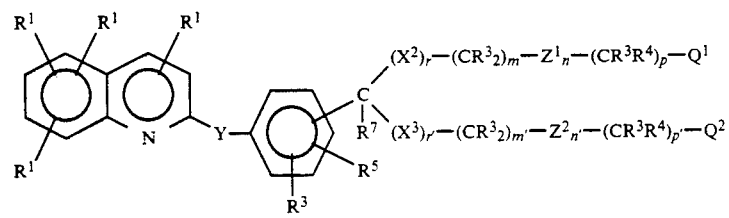

A

EP 318,093 (Merck)

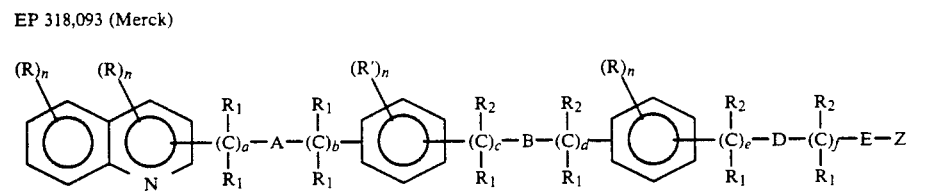

B

EP 315,399 (Rorer)

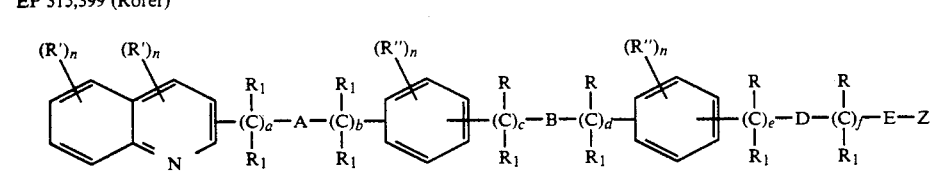

C

EP 348,155 (Rorer)

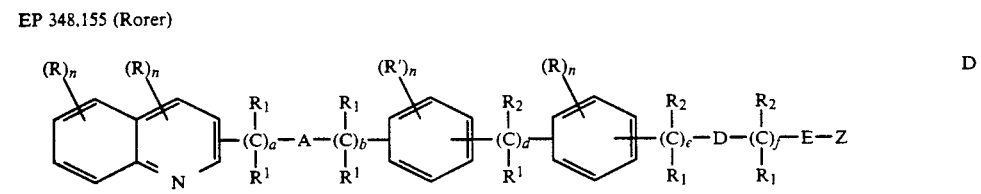

D

WO 89/04303 (Rorer)

substituted or unsubstituted 2-phenethyl, or two $R^2$ groups joined to the same carbon may form a ring of up to 8 members containing 0-2 heteroatoms chosen from O, S, and N;

$R^3$ is H or $R^2$;

$CR^3R^{22}$ may be the radical of a standard amino acid;

$R^4$ is halogen, —$NO_2$, —CN, —$OR^3$, —$SR^3$, $NR^3R^3$, $NR^3C(O)R^7$ or $R^3$;

$R^5$ is H, halogen, —$NO_2$, —$N_3$, —CN, —$SR^2$, —$NR^3R^3$, —$OR^3$, lower alkyl, or —$C(O)R^3$;

$R^6$ is —$(CH_2)_s$—$C(R^7R^7)$—$(CH_2)_s$—$R^8$ or —$CH_2$-$C(O)NR^{12}R^{12}$;

$R^7$ is H or $C_1$-$C_4$ alkyl;

$R^8$ is

A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or B) the radical W-$R^9$;

$R^9$ contains up to 20 carbon atoms and is (1) an alkyl group, or (2) an alkylcarbonyl group of an organic acyclic or monocyclic carboxylic acid containing 0-1 heteroatom in the ring;

$R^{10}$ is —$SR^{11}$, —$OR^{12}$, or —$NR^{12}R^{12}$;

$R^{11}$ is lower alkyl, —$C(O)R^{14}$, unsubstituted phenyl, or unsubstituted benzyl;

$R^{12}$ is H, $R^{11}$, or two $R^{12}$ groups joined to the same N may form a ring of 5 or 6 members containing 1-2 heteroatoms chosen from O, S, and N;

$R^{13}$ is lower alkyl, lower alkenyl, lower alkynyl, —$CF_3$ or substituted or unsubstituted phenyl, benzyl, or 2-phenethyl;

$R^{14}$ is H or $R^{13}$;

$R^{16}$ is H, $C_1$-$C_4$ alkyl, or OH;

$R^{17}$ is lower alkyl, lower alkenyl, lower alkynyl, or substituted or unsubstituted phenyl, benzyl, or 2-phenethyl;

$R^{18}$ is lower alkyl, lower alkenyl, lower alkynyl, —$CF_3$ or substituted or unsubstituted phenyl, benzyl, or 2-phenethyl;

$R^{19}$ is lower alkyl, lower alkenyl, lower alkynyl, —$CF_3$ or substituted or unsubstituted phenyl, benzyl, or 2-phenethyl;

$R^{20}$ is H, $C_1$-$C_4$ alkyl, substituted or unsubstituted phenyl, benzyl, phenethyl, or pyridinyl or two $R^{20}$ groups joined to the same N may form a saturated ring of 5 or 6 members containing 1-2 heteroatoms chosen from O, S, and N;

$R^{21}$ is H or $R^{17}$;

$R^{22}$ is $R^4$, $CHR^7OR^3$, or $CHR^7SR^2$;

m and m' are independently 0-8;

n and n' are independently 0 or 1, p and p' are independently 0-8;

m+n+p is 1-10 when r is 1 and $X^2$ is O, S, S(O), or $S(O)_2$;

m+n+p is 0-10 when r is 1 and $X^2$ is $CR^3R^{16}$;

m+n+p is 0-10 when r is 0;

m'+n'+p' is 0-10;

r and r' are independently 0 or 1;

s is 0-3;

$Q^1$ is —$C(O)OR^3$, —1H (or 2H)-tetrazol-5-yl, —$C(O)OR^6$, —$C(O)NHS(O)_2R^{13}$, —CN, —$C(O)NR^{12}R^{12}$, —$NR^{21}S(O)_2R^{13}$, —$NR^{12}C(O)NR^{12}R^{12}$, —$NR^{21}C(O)R^{18}$, —$OC(O)NR^{12}R^{12}$, —$C(O)R^{19}$, —$S(O)R^{18}$, —$S(O)_2R^{18}$, —$S(O)_2NR^{12}R^{12}$, —$NO_2$, —$NR^{21}C(O)OR^{17}$, —$C(NR^{12}R^{12})$=$NR^{12}$, —$C(R^{13})$=NOH; or if $Q^1$ is —C(O)OH and $R^{22}$ is —OH, —SH, —$CHR^7OH$ or —$NHR^3$, then $Q^1$ and $R^{22}$ and the carbons through which they are attached may form a heterocyclic ring by loss of water;

$Q^2$ is OH or $NR^{20}R^{20}$;

W is O, S, or $NR^3$;

$X^1$ is O, S, S(O), $S(O)_2$, or $NR^3$;

$X^2$ and $X^3$ are independently O, S, S(O), $S(O)_2$, or $CR^3R^{16}$;

Y is —$CR^3R^3$—$X^1$—, —$X^1$—$CR^3R^3$—, —$CR^3R^3$—$X^1$—$CR^3R^3$—, —$NR^3C(O)$—, or —$C(O)NR^3$—;

$Z^1$ and $Z^2$ are independently —HET(—$R^3$—$R^5$)—;

HET is the diradical of a benzene, a pyridine, a furan, or a thiophene;

and the pharmaceutically acceptable salts thereof.

DEFINITIONS

The following abbreviations have the indicated meanings:

Et=ethyl
Me=methyl
Bz=benzyl
Ph=phenyl
t-Bu=tertiary butyl
i-Pr=isopropyl
n-Pr=normal propyl
c-Hex=cyclohexyl
c-Pr=cyclopropyl
1,1-c-Bu=1,1-bis-cyclobutyl
1,1-c-Pr=1,1-bispcyclopropyl (e.g., $HOCH_2$(1,1-c-Pr)$CH_2CO_2Me$ is methyl 1-(hydroxymethyl)cyclopropaneacetate)
c-=cyclo
Ac=acetyl
Tz=1H(or 2H)-tetrazol-5-yl
Th=2- or 3-thienyl
$C_3H_5$=allyl
c-Pen=cyclopentyl
c-Bu=cyclobutyl
phe=benzenediyl
pye=pyridinediyl
fur=furandiyl
thio=thiophenediyl
DEAD=diethyl azodicarboxylate
DHP=dihydropyran
DIAD=diisopropyl azodicarboxylate
r.t.=room temperature Alkyl, alkenyl, and alkynyl are intended to include linear, branched, and cyclic structures and combinations thereof.

"Alkyl" includes "lower alkyl" and extends to cover carbon fragments having up to 20 carbon atoms. Examples of alkyl groups include octyl, nonyl, norbornyl, undecyl, dodecyl, tridecyl, tetradecyl, pentadecyl, eicosyl, 3,7-diethyl-2,2-dimethyl-4-propylnonyl, 2-(cyclododecyl)ethyl, adamantyl, and the like.

"Lower alkyl" means alkyl groups of from 1 to 7 carbon atoms. Examples of lower alkenyl groups include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, 2-methylcyclopropyl, cyclopropylmethyl, and the like.

"Lower alkenyl" groups means alkenyl groups of 2 to 7 carbon atoms. Examples of lower alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, and the like.

"Lower alkynyl" means alkynyl groups of 2 to 7 carbon atoms. Examples of lower alkynyl groups include ethynyl, propargyl, 3-methyl-1-pentynyl, 2-heptynyl, and the like.

"Alkylcarbonyl" means alkylcarbonyl groups of 1 to 20 carbon atoms of a straight, branched or cyclic configuration. Examples of alkylcarbonyl groups are 2-methylbutanoyl, octadecanoyl, 11-cyclohexylundecanoyl and the like. Thus, the 11-cyclohexylundecanoyl group is c-Hex—$(CH_2)_{10}$—C(O)—.

Substituted phenyl, benzyl, 2-phenethyl and pyridinyl means structures with 1 or 2 substituents on the aromatic ring selected from lower alkyl, $R^{10}$, $NO_2$, $SCF_3$, halogen, —C(O)$R^7$, —C(O)$R^{10}$, CN, $CF_3$, and $CN_4H$.

Halogen means F, Cl, Br and I.

The prodrug esters of Q (i.e., when Q=—C(O)$OR^6$) are intended to mean the esters such as are described by Saari et al., J. Med. Chem., 21, No. 8, 746-753 (1978), Sakamoto et al., Chem. Pharm. Bull., 32, No. 6, 2241-2248 (1984) and Bundgaard et al., J. Med. Chem., 30, No. 3, 451-454 (1987). Within the definition of $R^8$, some representative monocyclic or bicyclic heterocyclic radicals are:

2,5-dioxo-1-pyrrolidinyl,
(3-pyridinylcarbonyl)amino,
1,3-dihydro-1,3-dioxo-2H-isoindol-2-yl,
1,3-dihydro-2H-isoindol-2-yl,
2,4-imidazolinedion-1-yl,
2,6-piperidinedion-1-yl,
2-imidazolyl,
2-oxo-1,3-dioxolen-4-yl,
piperidin-1-yl,
morpholin-1-yl, and
piperazin-1-yl.

When $Q^1$ and $R^{22}$ and the carbons through which they are attached form a ring, the rings thus formed include lactones, lactams, and thiolactones.

It is intended that the definitions of any substituent (e.g., $R^1$, $R^2$, m, Q, X, etc.) in a particular molecule be independent of its definitions elsewhere in the molecule. Thus, —$NR^3R^3$ represents —NHH, —$NHCH_3$, —$NHC_6H_5$, etc.

The heterocycles formed when two $R^3$, $R^{12}$, or $R^{20}$ groups join through N include pyrrolidine, piperidine, morpholine, thiamorpholine, piperazine, and N-methylpiperazine.

"Standard amino acids", the radical of which may be $CR^3R^{22}$, means the following amino acids: alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine, and valine. (See F. H. C. Crick, Symposium of the Society of Experimental Biology, 12, 140 (1958)).

Some of the compounds described herein contain one or more centers of asymmetry and may thus give rise to diastereoisomers and optical isomers. The present invention is meant to comprehend such possible diastereoisomers as well as their racemic and resolved, optically active forms. Optically active (R) and (S) isomers may be resolved using conventional techniques.

Some of the compounds described herein contain olefinic double bonds, and unless specified otherwise, are meant to include both E and Z geometric isomers.

Preferred compounds of Formula I are those wherein:

$R^1$ is H, halogen, $CF_3$ or —CN;
$R^2$ is $C_1$-$C_4$ alkyl, —$CF_3$, —$CHF_2$, —$CH_2F$, or two $R^2$ groups joined to the same carbon may form a ring of up to 6 carbons;
$R^3$ is H or $R^2$;
$CR^3R^{22}$ may be the radical of a standard amino acid;
$R^4$ is —$OR^3$, —$SR^3$, $NR^3R^3$, $NHC(O)CH_3$, or $R^3$;
$R^5$ is H or halogen;
$R^6$ is —$(CH_2)_s$—C($R^7R^7$)—$(CH_2)_s$—$R^8$ or —$CH_2$-C(O)$NR^{12}R^{12}$;
$R^7$ is H or $C_1$-$C_4$ alkyl;
$R^8$ is
A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or
B) the radical W-$R^9$;
$R^9$ contains up to 20 carbon atoms and is (1) an alkyl group or (2) an alkylcarbonyl group;
$R^{10}$ is —$SR^{11}$, —$OR^{12}$, or —$NR^{12}R^{12}$;
$R^{11}$ is lower alkyl, —C(O)$R^{14}$, unsubstituted phenyl, or unsubstituted benzyl;
$R^{12}$ is H, $R^{11}$, or two $R^{12}$ groups joined to the same N may form a ring of 5 or 6 members containing 1-2 heteroatoms chosen from O, S, and N;
$R^{13}$ is lower alkyl, —$CF_3$, or unsubstituted phenyl, benzyl, or 2-phenethyl;
$R^{14}$ is H or $R^{13}$;
$R^{16}$ is H, $C_1$-$C_4$ alkyl, or OH;
$R^{22}$ is $R^4$, —$CH_2OR^3$, or —$CH_2SR^2$;
m and m' are independently 0-4;
n and n' are independently 0 or 1;
p and p' are independently 0-4;
m+n+p is 1-9 when r is 1 and $X^2$ is O or S;
m+n+p is 0-9 when r is 1 and $X^2$ is $CR^3R^{16}$;
m+n+p is 0-9 when r is 0;
m'+n'+p' is 1-9;
r and r' are independently 0 or 1;
s is 0-3;
$Q^1$ is —C(O)$OR^3$, 1H(or 2H)-tetrazol-5-yl, —C(O)$OR^6$, —C(O)NHS(O)$_2R^{13}$, —C(O)$NR^{12}R^{12}$, —NHS(O)$_2R^{13}$; or if $Q^1$ is C(O)OH and $R^{22}$ is —OH, —SH, —$CH_2OH$ or —$NHR^3$ then $Q^1$ and $R^{22}$ and the carbons through which they are attached may form a heterocyclic ring by loss of water;
$Q^2$ is OH;
W is O, S, or NH;
$X^1$ is O, S, or $NR^3$;
$X^2$ and $X^3$ are independently O, S, or $CR^3R^{16}$;
Y is —$CR^3R^3$—$X^1$—;
$Z^1$ and $Z^2$ are independently —HET(—$R^3$—$R^5$)—;
HET is the diradical of a benzene, pyridine, furan, or thiophene;
and the pharmaceutically acceptable salts thereof.

Another group of preferred compounds are those wherein the $R^{22}$ α to $Q^1$ is lower alkyl, $CF_3$, or substituted or unsubstituted phenyl.

More preferred compounds of Formula I are represented by Formula Ia:

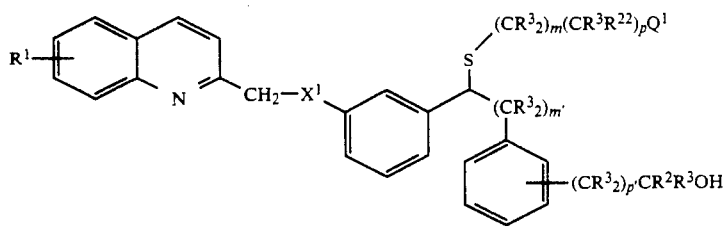

wherein:
R$^1$ is H, halogen, CF$_3$, or CN;
R$^{22}$ is R$^3$, —CH$_2$OR$^3$, or —CH$_2$SR$^2$;
Q$^1$ is —C(O)OH, 1H(or 2H)-tetrazol-5-yl, —C(O)NHS(O)$_2$R$^{13}$, —C(O)NR$^{12}$R$^{12}$, or —NHS(O)$_2$R$^{13}$;
m' is 2 or 3;
p' is 0 or 1;
m+p is 1-5;
the remaining definitions are as in Formula I; and the pharmaceutically acceptable salts thereof.

Another group of more preferred compounds are as in Formula Ia, wherein:
m' is 0;
and the remaining definitions are as in Formula Ia.

Another group of more preferred compounds of Formula I are represented by Formula Ib:

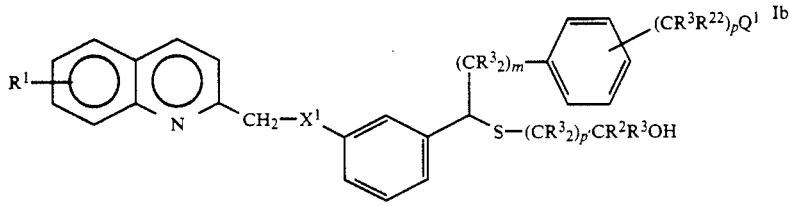

wherein:
m is 0, 2 or 3;
p is 0 or 1;
p' is 1-4;
m+p is 0-4;
the remaining definitions are as in Formula Ia; and the pharmaceutically acceptable salt thereof.

The most preferred compound of Formulas Ia and Ib are those wherein X$^1$ is 0. The most preferred compounds of Formula Ia also have a lower alkyl on the carbon α to the group Q$^1$.

SALTS

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

It will be understood that in the discussion of methods of treatment which follows, references to the compounds of Formula I are meant to also include the pharmaceutically acceptable salts.

UTILITIES

The compounds of the present invention have modest activity as inhibitors of leukotriene biosynthesis, and are of utility principally because of their excellent activity as antagonists of the actions of the leukotrienes.

The ability of the compounds of Formula I to antagonize the actions of the leukotrienes makes them useful for preventing or reversing the symptoms induced by the leukotrienes in a human subject. This antagonism of the actions of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as psoriasis, atopic eczema, and the like, 6) cardiovascular disorders such as angina, myocardial ischemia, hypertension, platelet aggregation and the like, 7) renal insufficiency arising from ischaemia induced by immunological or chemical (cyclosporin) etiology, 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small and large-airway diseases, and 15) cholecystitis.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. The compounds also exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in EP 140,684.

DOSE RANGES

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

PHARMACEUTICAL COMPOSITIONS

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (opthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of compound I in suitable propellants, such as fluorocarbons or hydrocarbons.

Suitable topical formulations of Compound I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
|---|---|
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

COMBINATIONS WITH OTHER DRUGS

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the oxicams; and
(5) the biphenylcarboxylic acid derivatives;
or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free $-CH(CH_3)COOH$ or $-CH_2CH_2COOH$ group (which optionally can be in the form of a pharmaceutically acceptable salt group, e.g., $-CH(CH_3)COO^-Na^+$ or $-CH_2CH$-

$_2COO^-Na^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —$CH_2COOH$ group (which optionally can be in the form of a pharmaceutically acceptable salt group, e.g. —$CH_2COO^-Na^+$), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

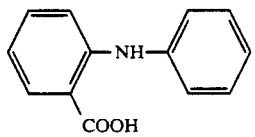

which can bear a variety of substituents and in which the free —COOH group can be in the form of a pharmaceutically acceptable salt group, e.g., —$COO^-Na^+$. The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

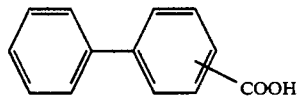

which can bear a variety of substituents and in which the free —COOH group can be in the form of a pharmaceutically acceptable salt group, e.g., —$COO^-Na^+$.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non narcotic analgesics/non-steroidal anti-inflammatory drugs which have the general formula:

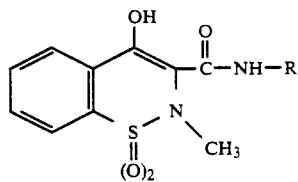

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid and ufenamate.

The following NSAIDs, designated by company code number (see e.g., Pharmaprojects), may also be used:

480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDS are acetyl salicylic acid, diclofenac, fenbufen, fenoprofen, flurbiprofen, ibuprofen, ketoprofen, naproxen, phenylbutazone, piroxicam, sulindac and tolmetin.

Pharmaceutical compositions comprising the Formula I compounds may also contain inhibitors of the biosynthesis of the leukotrienes such as are disclosed in EP 138,481 (Apr. 24, 1985), EP 115,394 Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as a-fluoromethylhistidine, described in U.S. Pat. No. 4,325,961. The compounds of the Formula I may also be advantageously combined with an $H_1$ or $H_2$-receptor antagonist, such as for instance acetamazole, aminothiadiazoles disclosed in EP 40,696 Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906.

Another useful pharmaceutical composition comprises the Formula I compounds in combination with serotonin antagonists such as methysergide, the serotonin antagonists described in *Nature*, Vol. 316, pages 126–131, 1985, and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

REPRESENTATIVE COMPOUNDS

Table I illustrates compounds representative of the present invention. Table II provides elemental analyses for compounds of Table I.

TABLE I

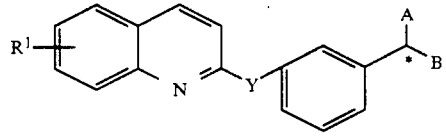

I'

| EX. | * | $R^1$ | Y | A | B |
|---|---|---|---|---|---|
| 1 | RS | 7-Cl | $CH_2O$ | $SCH_2CHMeCO_2H$ | $(CH_2)_2(1,2\text{-phe})CMe_2OH$ |
| 2 | RS | 7-Cl | $CH_2O$ | $S(CH_2)_2CO_2H$ | $(CH_2)_2(1,2\text{-phe})C((CH_2)_4)OH$ |
| 3 | RS | 7-Cl | $CH_2O$ | $S(CH_2)_2CO_2H$ | $(CH_2)_2(4\text{-Cl-1,2-phe})CMe_2OH$ |
| 4 | RS | 7-Cl | $CH_2O$ | $SCH_2CHMeCO_2H$ | $(1,3\text{-phe})CMe_2OH$ |
| 5 | RS | 7-Cl | $CH_2O$ | $SCH_2(R)CH(NHAc)CO_2H$ | $(CH_2)_2(1,2\text{-phe})CMe_2OH$ |
| 6 | R | 7-Cl | $CH_2O$ | $SCH_2(S)CHMeCO_2H$ | $(CH_2)_2(1,2\text{-phe})CMe_2OH$ |
| 7 | R | 7-Cl | $CH_2O$ | $SCH_2(R)CHMeCO_2H$ | $(CH_2)_2(1,2\text{-phe})CMe_2OH$ |
| 8 | S | 7-Cl | $CH_2O$ | $SCH_2(S)CHMeCO_2H$ | $(CH_2)_2(1,2\text{-phe})CMe_2OH$ |
| 9 | S | 7-Cl | $CH_2O$ | $SCH_2(R)CHMeCO_2H$ | $(CH_2)_2(1,2\text{-phe})CMe_2OH$ |
| 10 | RS | 7-Cl | $CH_2O$ | $SCH_2CHEtCO_2H$ | $(CH_2)_2(1,2\text{-phe})CMe_2OH$ |
| 11 | RS | 7-Cl | $CH_2O$ | $S(CH_2)_2CO_2H$ | $(CH_2)_2(1,2\text{-phe})CMe_2OH$ |
| 12 | RS | 7-Cl | $CH_2O$ | $SCH_2CMe_2CO_2H$ | $(CH_2)_2(1,2\text{-phe})CMe_2OH$ |
| 13 | RS | 7-Cl | $CH_2S$ | $SCH_2CHMeCO_2H$ | $(CH_2)_2(1,2\text{-phe})CMe_2OH$ |
| 14 | RS | 7-Cl | $CH_2O$ | $S(CH_2)_2CO_2H$ | $(CH_2)_2(1,2\text{-phe})CMe_2OH$ |
| 15 | RS | 7-Br | $CH_2O$ | $SCH_2CHMeCO_2H$ | $(CH_2)_2(1,2\text{-phe})CMe_2OH$ |
| 16 | S | 7-Br | $CH_2O$ | $SCH_2(S)CHMeCO_2H$ | $(CH_2)_2(1,2\text{-phe})CMe_2OH$ |
| 17 | R | 7-Br | $CH_2O$ | $SCH_2(S)CHMeCO_2H$ | $(CH_2)_2(1,2\text{-phe})CMe_2OH$ |
| 18 | S | 7-Cl | $CH_2O$ | $S(CH_2)_2CO_2H$ | $S(CH_2)_2CMe_2OH$ |
| 19 | S | 7-Cl | $CH_2O$ | $SCH_2CHMeCO_2H$ | $(CH_2)_2(1,3\text{-phe})C(CF_3)_2OH$ |
| 20 | RS | 7-Cl | $CH_2O$ | $SCH_2CHMeCO_2H$ | $(CH_2)_2(1,2\text{-phe})C(CF_3)_2OH$ |
| 21 | RS | 7-Cl | $CH_2O$ | $SCH_2CHMeCO_2H$ | $(CH_2)_2(1,3\text{-phe})CMe_2OH$ |
| 22 | RS | 7-Cl | $CH_2O$ | $SCH_2CHEtCO_2H$ | $SCH_2CMe_2CMe_2OH$ |
| 23 | RS | 7-Cl | $CH_2O$ | $SCH_2CHMeCMe_2OH$ | $(CH_2)_2(1,2\text{-phe})CO_2H$ |
| 24 | RS | 7-Cl | $CH_2O$ | $SCH_2CHMeCMe_2OH$ | $(CH_2)_2(1,2\text{-phe})CONH_2$ |
| 25 | RS | 7-Cl | $CH_2O$ | $SCH_2CHMeCO_2H$ | $SCH_2(1,2\text{-phe})CMe_2OH$ |
| 26 | RS | 7-Cl | $CH_2O$ | $SCH_2CHMeCO_2H$ | $(CH_2)_2(1,4\text{-phe})CMe_2OH$ |
| 27 | RS | 7-Cl | $CH_2S$ | $SCH_2CHEtCO_2H$ | $(CH_2)_2(1,3\text{-phe})CMe_2OH$ |
| 28 | RS | 7-Cl | $CH_2O$ | $SCH_2CH(OMe)CO_2H$ | $(CH_2)_2(1,2\text{-phe})CMe_2OH$ |
| 29 | S | 7-Cl | $CH_2O$ | $SCH_2(R)CHEtCO_2H$ | $(CH_2)_2(1,2\text{-phe})CMe_2OH$ |
| 30 | RS | 7-Cl | $CH_2O$ | $S(CH_2)_2CO_2H$ | $(CH_2)_2(1,2\text{-phe})CH(CF_3)OH$ |
| 31 | RS | 7-Cl | $CH_2OCH_2$ | $SCH_2CHEtCO_2H$ | $(CH_2)_2(1,2\text{-phe})CMe_2OH$ |
| 32 | RS | 7-F | $CH_2O$ | $SCH_2CH(n\text{-Pr})CO_2H$ | $(CH_2)_2(1,2\text{-phe})CMe_2OH$ |
| 33 | RS | 7-Cl | $CH_2O$ | $SCH_2CMe_2CO_2H$ | $(CH_2)_2(1,2\text{-phe})CMe_2OH$ |
| 34 | RS | 7-Cl | $CH_2O$ | $SCH_2CHEtCO_2H$ | $(CH_2)_2(1,3\text{-phe})CMe_2OH$ |
| 35 | RS | 7-$CF_3$ | $CH_2O$ | $SCH_2CHEtCO_2H$ | $(CH_2)_2(1,2\text{-phe})C(CF_3)_2OH$ |
| 36 | RS | H | $CH_2O$ | $SCH_2CHEtCO_2H$ | $(CH_2)_2(1,2\text{-phe})CMe_2OH$ |
| 37 | RS | H | $CH_2O$ | $SCH_2CHEtCO_2H$ | $(1,3\text{-phe})CMe_2OH$ |
| 38 | RS | 7-Cl | $CH_2O$ | $SCH_2CHEtCO_2H$ | $(CH_2)_2(4\text{-Br-1,2-phe})CMe_2OH$ |
| 39 | RS | 7-Cl | $CH_2O$ | $SCH_2CHEtCO_2H$ | $(CH_2)_2(1,2\text{-phe})CMeEtOH$ |
| 40 | RS | 7-Cl | $CH_2O$ | $SCH_2CHEtCO_2H$ | $(CH_2)_2(1,2\text{-phe})CEt_2OH$ |
| 41 | RS | 7-Cl | $CH_2O$ | $SCH_2CHEtCO_2H$ | $(CH_2)_2(1,2\text{-phe})C((CH_2)_3)OH$ |
| 42 | RS | 7-Cl | $CH_2O$ | $SCH_2CHMeCO_2H$ | $(CH_2)_2(1,2\text{-phe})CMe_2NH_2$ |
| 43 | RS | 7-CL | $CH_2O$ | $SCH_2CHEtCO_2H$ | $(CH_2)_2(1,2\text{-phe})CHMeNHMe$ |

TABLE I-continued

I'

Structure: quinoline with $R^1$ substituent, connected at 2-position via Y to a phenyl ring bearing -CH(A)(B) group (with * indicating chirality)

| EX. | * | $R^1$ | Y | A | B |
|---|---|---|---|---|---|
| 44 | RS | 7-Cl | $CH_2O$ | $SCH_2CHEtCO_2H$ | $(CH_2)_2(1,2$-phe$)CHMeNMe_2$ |
| 45 | RS | 7-Cl | $CH_2O$ | $SCH_2CHEtCO_2H$ | $(CH_2)_2(2,5$-fur$)CMe_2OH$ |
| 46 | RS | 7-Cl | $CH_2O$ | $SCH_2CHEtCO_2H$ | $(CH_2)_2(2,6$-pye$)CMe_2OH$ |
| 47 | RS | 7-Cl | $CH_2O$ | $SCH_2CHEtCO_2H$ | $(CH_2)_2(4,2$-pye$)CMe_2OH$ |
| 48 | RS | 7-Cl | $CH_2O$ | $SCH_2CHEtCO_2H$ | $(CH_2)_2(2,5$-thio$)CMe_2OH$ |
| 49 | RS | 7-Cl | $CH_2O$ | $SCH_2CHEtCO_2H$ | $(CH_2)_2(3,2$-pye$)CMe_2OH$ |
| 50 | RS | 7-CN | $CH_2O$ | $SCH_2CHEtCO_2H$ | $(CH_2)_2(1,4$-phe$)CMe_2OH$ |
| 51 | RS | 7-Cl | $CH_2O$ | $SCH_2CHEtCO_2H$ | $(CH_2)_2(1,4$-phe$)CMe_2OH$ |
| 52 | RS | 7-Cl | $CH_2O$ | $SCH_2CHMeCONHS(O)_2Me$ | $(CH_2)_2(1,2$-phe$)CMe_2OH$ |
| 53 | RS | 7-Cl | $CH_2O$ | $SCH_2CHMeCONH_2$ | $(CH_2)_2(1,2$-phe$)CMe_2OH$ |
| 54 | RS | 7-Cl | $CH_2O$ | $SCH_2CHMeCONHMe$ | $(CH_2)_2(1,2$-phe$)CMe_2OH$ |
| 55 | RS | 7-Cl | $CH_2O$ | $SCH_2CHMeTz$ | $(CH_2)_2(1,2$-phe$)CMe_2OH$ |
| 56 | RS | 7-Cl | $CH_2O$ | $SCH_2CHEtTz$ | $(CH_2)_2(1,2$-phe$)CEt_2OH$ |
| 57 | RS | 7-Cl | $CH_2O$ | $SCH_2CHEtCONHS(O)_2CF_3$ | $(CH_2)_2(1,2$-phe$)CMe_2OH$ |
| 58 | RS | 7-Cl | $CH_2O$ | $SCH_2CHMeNO_2$ | $(CH_2)_2(1,2$-phe$)CMe_2OH$ |
| 59 | RS | 7-Cl | $CH_2O$ | $S(CH_2)_2CONHS(O)_2Ph$ | $(CH_2)_2(1,2$-phe$)CMe_2OH$ |
| 60 | R | 7-Cl | $CH_2O$ | $SCH_2(S)CHEtCO_2H$ | $(CH_2)_2(1,2$-phe$)C(n$-Pr$)_2OH$ |
| 61 | RS | 7-Cl | $CH_2O$ | $S(CH_2)_2CO_2H$ | $(CH_2)_2(1,2$-phe$)CH_2CMe_2OH$ |
| 62 | S | 7-Cl | $CH_2O$ | $SCH_2(S)CHEtCO_2H$ | $(CH_2)_2(1,2$-phe$)CMe_2OH$ |
| 63 | RS | 7-Cl | $CH_2O$ | $SCH_2CH(n$-Pr$)CO_2H$ | $(CH_2)_2(1,2$-phe$)CMe_2NH_2$ |
| 64 | S | 7-Cl | $CH_2O$ | $SCH_2CH(CH_2(4$-ClPh$))CO_2H$ | $(CH_2)_2(1,2$-phe$)CMe_2OH$ |
| 65 | S | 7-Cl | $CH_2O$ | $SCH_2CH(CH_2CH=CH_2)CO_2H$ | $(CH_2)_2(1,2$-phe$)CMe_2OH$ |
| 66 | S | 7-Cl | $CH_2S(O)_2$ | $SCH_2CHEtCO_2H$ | $(CH_2)_2(1,2$-phe$)CHMeOH$ |
| 67 | S | 7-Cl | $CH_2O$ | $SCH_2CH(CH_2SMe)CO_2H$ | $(CH_2)_2(1,2$-phe$)CMe_2OH$ |
| 68 | S | 7-Cl | $CH_2O$ | $SCH_2CH(c$-Pr$)CO_2H$ | $(CH_2)_2(1,2$-phe$)CMe_2OH$ |
| 69 | S | 7-Cl | $CH_2O$ | $SCH_2CH(CH_2C\equiv CH)CO_2H$ | $(CH_2)_2(1,2$-phe$)CMe_2OH$ |
| 70 | S | 7-Cl | $CH_2O$ | $SCH_2CH(CH_2Ph)CO_2H$ | $(CH_2)_2(1,2$-phe$)CMe_2OH$ |
| 71 | RS | 7-Cl | $CH_2O$ | $SCH_2CHMeCO_2H$ | $(CH_2)_2(1,2$-phe$)CHMeOH$ |
| 72 | S | 7-Cl | $CH_2O$ | $SCH_2CHPhCO_2H$ | $(CH_2)_2(1,2$-phe$)CMe_2OH$ |
| 73 | S | 7-Cl | $CH_2S$ | $SCH_2CHMeCO_2H$ | $(CH_2)_2(1,2$-phe$)CH_2CMe_2OH$ |
| 74 | S | 7-Cl | $CH_2O$ | $SCH_2CHEtCO_2H$ | $(CH_2)_2(1,2$-phe$)CH_2CMe_2OH$ |
| 75 | S | 7-Cl | $CH_2O$ | $SCH_2CH(n$-Pr$)CO_2H$ | $(CH_2)_2(1,2$-phe$)CMe_2OH$ |
| 76 | RS | 7-Cl | $CH_2O$ | $SCH_2CHEtCO_2H$ | $(1,2$-phe$)CMe_2OH$ |
| 77 | S | 7-Cl | $CH_2O$ | $SCH_2CHEtCO_2H$ | $(CH_2)_2(1,2$-phe$)C(CH_2OCH_2)OH$ |
| 78 | RS | 7-Cl | $CH_2O$ | $S(CH_2)_2CMe_2OH$ | $(CH_2)_2(1,2$-phe$)CO_2H$ |
| 79 | RS | 7-Cl | $CH_2O$ | $S(CH_2)_2CMe_2OH$ | $(1,3$-phe$)CO_2H$ |
| 80 | RS | 7-Cl | $CH_2O$ | $S(CH_2)_2CO_2H$ | $CH_2CHOH(1,4$-phe$)CN$ |
| 81 | RS | 7-Cl | $CH_2O$ | $S(CH_2)_2CO_2H$ | $CH_2CHOH(1,3$-phe$)CN_4H$ |
| 82 | RS | 7-Cl | $CH_2O$ | $S(CH_2)_2CO_2H$ | $CH_2CHOH(1,4$-phe$)CN_4H$ |
| 83 | S | 7-Cl | $CH_2O$ | $S(CH_2)_2CO_2H$ | $(CH_2)_2(1,2$-phe$)CMe_2OH$ |
| 84 | S | 7-Cl | $CH_2O$ | $SCH_2CHCF_3CO_2H$ | $(CH_2)_2(1,2$-phe$)CMe_2OH$ |
| 85 | S | 7-Cl | $CH_2O$ | $S(CH_2)_3CO_2H$ | $(CH_2)_2(1,2$-phe$)CMe_2OH$ |
| 86 | S | 7-Cl | $CH_2O$ | $S(CH_2)_2CHMeCO_2H$ | $(CH_2)_21,2$-phe$)CMe_2OH$ |
| 87 | S | 7-Cl | $CH_2O$ | $S(O)_2CH_2(S)CHEtCO_2H$ | $(CH_2)_2(1,2$-phe$)CMe_2OH$ |
| 88 | S | 7-Cl | $CH_2O$ | $SCH_2CH(CH_2OMe)CO_2H$ | $(CH_2)_2(1,2$-phe$)CMe_2OH$ |
| 89 | S | 7-Cl | $CH_2O$ | $S(CH_2)_2CMe_2OH$ | $(CH_2)_2(1,2$-phe$)CO_2H$ |
| 90 | R | 7-Cl | $CH_2O$ | $S(CH_2)_2CMe_2OH$ | $(CH_2)_2(1,2$-phe$)CO_2H$ |
| 91 | S | 7-Cl | $CH_2O$ | $SCH_2(S)CHEtCO_2H$ | $(CH_2)_2(1,3$-phe$)CMe_2OH$ |
| 92 | S | 7-Cl | $CH_2O$ | $SCH_2CHEtCO_2H$ | $(CH_2)_2(1,3$-phe$)(1,1$-c-Bu$)OH$ |
| 93 | S | 7-Cl | $CH_2O$ | $S(CH_2)_2CMe_2OH$ | $(CH_2)_3(1,2$-phe$)COOH$ |
| 94 | R | 7-Cl | $CH_2O$ | $S(CH_2)_2CO_2H$ | $S(CH_2)_2(1$-1-c-Pen$)OH$ |
| 95 | S | 7-Cl | $CH_2O$ | $SCH_2CH(CH_2CF_3)CO_2H$ | $(CH_2)_2(1,2$-phe$)CMe_2OH$ |
| 96 | S | 7-Cl | $CH_2O$ | $S(CH_2)_2CMe_2OH$ | $(CH_2)_2(4$-Cl-$1,2$-phe$)CO_2H$ |
| 97 | R | 7-Cl | $CH_2O$ | $SCH_2(S)CHEtCONHS(O)_2Me$ | $(CH_2)_2(1,2$-phe$)CMe_2OH$ |
| 98 | S | 7-Cl | $CH_2O$ | $S(CH_2)_2CMeOH$ | $(CH_2)_2(1,3$-phe$)CMe_2CO_2H$ |
| 99 | S | 7-Cl | $CH_2O$ | $S(CH_2)_2CMeOH$ | $(CH_2)_2(1,3$-phe$)CHMeCO_2H$ |
| 100 | S | 7-Cl | $CH_2O$ | $S(CH_2)_3CMe_2OH$ | $(CH_2)_2(1,2$-phe$)CO_2H$ |
| 101 | S | 7-Cl | $CH_2O$ | $SCH_2(S)CHEtCO_2H$ | $(CH_2)_2(1,4$-phe$)CMe_2OH$ |
| 102 | RS | 7-Cl | $CH_2O$ | $S(CH_2)_2CMe_2OH$ | $(CH_2)_2(1,3$-phe$)CN_4H$ |
| 103 | S | 7-Cl | $CH_2O$ | $S(CH_2)_3CMe_2OH$ | $(CH_2)_2(1,2$-phe$)CHMeCO_2H$ |
| 104 | S | 7-Cl | $CH_2O$ | $S(CH_2)_3CMe_2OH$ | $(CH_2)_2(1,2$-phe$)CHMeCONHS(O)_2CH_3$ |
| 105 | S | 7-Cl | $CH_2O$ | $S(CH_2)_2CMe_2OH$ | $(CH_2)_3(1,2$-phe$)CO_2H$ |
| 106 | R | 7-Cl | $CH_2O$ | $S(O)_2CH_2(S)CHEtCO_2H$ | $(CH_2)_2(1,2$-phe$)CMe_2OH$ |
| 107 | S | 7-Cl | $CH_2O$ | $S(CH_2)_2CMe_2OH$ | $(CH_2)_2(4$-Cl-$1,2$-phe$)CHMeCO_2H$ |
| 108 | S | 7-Cl | $CH_2O$ | $SCH_2(S)CHMeCO_2H$ | $(CH_2)_2(1,2$-phe$)CH_2CMe_2OH$ |
| 109 | S | 7-Cl | $CH_2O$ | $S(CH_2)_3CMe_2OH$ | $(CH_2)_2(4$-Cl-$1,2$-phe$)CO_2H$ |
| 110 | R | 7-Cl | $CH_2O$ | $S(CH_2)_2CMe_2OH$ | $(CH_2)_2(4$-Cl-$1,2$-phe$)CO_2H$ |
| 111 | S | 7-Cl | $CH_2O$ | $S(CH_2)_3CMe_2OH$ | $(CH_2)_2(1,2$-phe$)CMe_2CO_2H$ |
| 112 | S | 7-Cl | $CH_2O$ | $S(CH_2)_2CMe_2OH$ | $(CH_2)_3(R)CHMe_2CO_2H$ |
| 113 | S | 7-Cl | $CH_2O$ | $S(CH_2)_3CEt_2OH$ | $(CH_2)_2(1,2$-phe$)CO_2H$ |
| 114 | S | 7-Cl | $CH_2O$ | $S(CH_2)_3CEt_2OH$ | $(CH_2)_2(1,2$-phe$)CHMeCO_2H$ |
| 115 | R | 7-Cl | $CH_2O$ | $SCHMeCH_2CO_2H$ | $(CH_2)_2(1,2$-phe$)CMe_2OH$ |
| 116 | S | 7-Cl | $CH_2O$ | $S(CH_2)_3CMe_2OH$ | $(CH_2)_2(1,2$-phe$)CHEtCO_2H$ |

TABLE I-continued

I'

| EX. | * | R¹ | Y | A | B |
|---|---|---|---|---|---|
| 117 | S | 7-Cl | CH₂O | S(CH₂)₃CMe₂OH | (CH₂)₂(1,2-phe)CH(n-Pr)CO₂H |
| 118 | S | 7-Cl | CH₂O | S(CH₂)₃CMe₂OH | (CH₂)₂(1,2-phe)CH(i-Pr)CO₂H |
| 119 | R | 7-Cl | CH₂O | SCH₂MeCHMeCO₂H | (CH₂)₂(1,2-phe)CMe₂OH |
| 120 | R | 7-Cl | CH₂O | S(CH₂)₂CMe₂OH | (CH₂)₃(R)CHMeCO₂H |
| 121 | R | 7-Cl | CH₂O | SCH₂(S)CHMeCN₄H | (CH₂)₂(1,2-phe)CMe₂OH |
| 122 | S | 7-Cl | CH₂O | SCH₂(S)CHMeCO₂H | (CH₂)₂(3-OH-1,4-phe)CHMeOH |
| 123 | S | 7-Cl | CH₂O | S(CH₂)₃CHMeOH | (CH₂)₂(1,2-phe)CHMeCO₂H |
| 124 | R | 7-Cl | CH₂O | S(S)CHMeCH₂CO₂H | (CH₂)₂(1,2-phe)CMe₂OH |
| 125 | R | 7-Cl | CH₂O | S(R)CHMeCH₂CO₂H | (CH₂)₂(1,2-phe)CMe₂OH |
| 126 | R | 7-Cl | CH₂O | S(S)CHMe(S)CHMeCO₂H | (CH₂)₂(1,2-phe)CMe₂OH |
| 127 | R | 7-Cl | CH₂O | S(R)CHMe(R)CHMeCO₂H | (CH₂)₂(1,2-phe)CMe₂OH |
| 128 | R | 7-Cl | CH₂O | SCHEtCH₂CO₂H | (CH₂)₂(1,2-phe)CMe₂OH |
| 129 | S | 7-Cl | CH₂O | S(CH₂)₃CHMeOH | (CH₂)₂(1,2-phe)CHEtCO₂H |
| 130 | S | 7-Cl | CH₂O | SCH₂(S)CHMeCO₂H | (CH₂)₂(1,2-phe)CH(OH)CH₂—(OH)Ph |
| 131 | R | 7-Cl | CH₂O | SCMe₂CH₂CO₂H | (CH₂)₂(1,2-phe)CMe₂OH |
| 132 | R | 7-Cl | CH₂O | SCH₂CHMeCH₂CO₂H | (CH₂)₂(1,2-phe)CMe₂OH |
| 133 | R | 7-Cl | CH₂S | SCH₂(1,1-c-Pr)CH₂CO₂H | (CH₂)₂(1,2-phe)CMe₂OH |
| 134 | S | 7-Cl | CH₂SO₂ | SCH₂(1,1-c-Pr)CH₂CO₂H | (CH₂)₂(1,2-phe)CO₂H |
| 135 | S | 7-Cl | CH₂O | S(CH₂)₃CMe₂OH | (CH₂)₂(1,2-phe)(R)CHEtCO₂H |
| 136 | S | 7-Cl | CH₂O | S(CH₂)₃CMe₂OH | (CH₂)₂(1,2-phe)(S)CHEtCO₂H |
| 137 | S | 7-Cl | CH₂O | S(CH₂)₃CMe₂OH | (CH₂)₂(4-Cl-1,2-phe)CHEtCO₂H |
| 138 | S | 7-Cl | CH₂O | S(CH₂)₃CMe₂OH | (CH₂)₂(1,2-phe)CEt₂CO₂H |
| 139 | S | 7-Cl | CH₂O | S(CH₂)₃CMe₂OH | (CH₂)₂(1,2-phe)CH₂CO₂H |
| 140 | S | 7-Cl | CH₂O | S(CH₂)₃CMe₂OH | (CH₂)₂(1,2-phe)CH(OH)CO₂H |
| 141 | S | 7-Cl | CH₂S | SCH₂Me₂CH₂CO₂H | (CH₂)₂(1,2-phe)CHEtCO₂H |
| 142 | S | 7-Cl | CH₂O | S(CH₂)₃CMe₂OH | (CH₂)₂CHMeCH₂CO₂H |
| 143 | R | 7-Cl | CH₂O | SCH₂CMe₂CH₂CO₂H | (CH₂)₂(1,2-phe)CMe₂OH |
| 144 | S | 7-Cl | CH₂O | S(CH₂)₄CMe₂OH | (CH₂)₂(1,2-phe)CHEtCO₂H |
| 145 | S | 7-F | CH₂O | SCH₂Me₂CH₂CO₂H | (CH₂)₂(1,2-phe)CO₂H |
| 146 | S | 7-Br | CH₂O | SCH₂Me₂CH₂CO₂H | (CH₂)₂(1,2-phe)CO₂H |
| 147 | S | 7-I | CH₂O | SCH₂(1,1-c-Pr)CH₂CO₂H | (CH₂)₂(1,2-phe)CMe₂OH |
| 148 | S | 7-CF₃ | CH₂O | SCH₂(1,1-c-Bu)CH₂CO₂H | (CH₂)₂(1,2-phe)CMe₂OH |
| 149 | S | 7-CN | CH₂O | SCH₂Me₂CH₂CO₂H | (CH₂)₂(1,2-phe)CEt₂OH |
| 150 | S | 7-NO₂ | CH₂O | SCH₂(1,1-c-Pr)CH₂CO₂H | (CH₂)₂(1,2-phe)CMe₂OH |
| 151 | R | 7-N₃ | CH₂O | SCH₂(1,1-c-Pr)CH₂CO₂H | (CH₂)₂(1,2-phe)CMe₂OH |
| 152 | RS | 7-Cl | CH₂O | S(CH₂)₂CMe₂OH | (CH₂)₂CMe₂CH₂CO₂H |
| 153 | S | 7-Cl | CH₂O | S(1,2-phe)CH₂CO₂H | (CH₂)₂(1,2-phe)CMe₂OH |
| 154 | R | 7-Cl | CH₂O | S(CH₂)₃CMe₂OH | (CH₂)₂(1,2-phe)CHEtCO₂H |
| 155 | S | 7-Cl | CH₂O | S(CH₂)₂CMe₂OH | (CH₂)₂(1,2-phe)CHEtCO₂H |
| 156 | S | 7-Cl | CH₂O | S(CH₂)₃CMe(4-Cl—Ph)OH | (CH₂)₂(1,2-phe)CHEtCO₂H |
| 157 | R | 7-Cl | CH₂O | SCH₂(1,2-phe)CMe₂OH | (CH₂)₂CMe₂CH₂CO₂H |
| 158 | R | 7-Cl | CH₂O | SCH₂(1,1-c-Pr)CH₂CO₂H | (CH₂)₂(1,2-phe)CMe₂OH |
| 159 | R | 7-Cl | CH₂CH₂ | SCH₂(1,1-c-Pr)CH₂CO₂H | (CH₂)₂(1,2-phe)CMe₂OH |
| 160 | R | 7-Cl | CH₂O | SCH₂CMe₂CHMeCO₂H | (CH₂)₂(1,2-phe)CMe₂OH |
| 161 | S | 7-Cl | CH₂O | SCH₂(1,2-phe)CMe₂OH | (CH₂)₂CMe₂CH₂CO₂H |
| 162 | R | 7-Cl | CH₂O | SCHMeCMe₂CH₂CO₂H | (CH₂)₂(1,2-phe)CMe₂OH |
| 163 | R | 7-Cl | CH₂O | S(1,1-c-Pr)CH₂CO₂H | (CH₂)₂(1,2-phe)CMe₂OH |
| 164 | R | 7-Cl | CH₂O | S(1,1-c-Pr)CHMeCO₂H | (CH₂)₂(1,2-phe)CMe₂OH |
| 165 | R | 7-Cl | CH₂O | S(1,1-c-Pr)CH₂CO₂H | (CH₂)₂(1,3-phe)CMe₂OH |
| 166 | R | 7-Cl | CH₂O | S(1,1-c-Pr)CH₂CO₂H | (CH₂)₂(1,2-phe)(1,1-c-Bu)OH |
| 167 | R | 7-Cl | CH₂O | S(1,1-c-Pr)CH₂CO₂H | (CH₂)₂(1,3-phe)(1,1-c-Bu)OH |
| 168 | R | 7-Cl | CH₂O | SCH₂(1,1-c-Pr)CH₂CO₂H | (CH₂)₂(1,3-phe)CMe₂OH |
| 169 | R | 7-Cl | 1 | SCH₂(1,1-c-Pr)CH₂CO₂H | (CH₂)₂(1,2-phe)CMe₂OH |
| 170 | R | 7-Cl | OCH₂ | S(1,1-c-Pr)CH₂CO₂H | (CH₂)₂(1,2-phe)CMe₂OH |
| 171 | R | 7-F | 2 | S(1,1-c-Pr)CH₂CO₂H | (CH₂)₂(1,2-phe)CMe₂OH |
| 172 | R | 6,7-F₂ | CH₂O | S(1,1-c-Pr)CH₂CO₂H | (CH₂)₂(1,2-phe)CMe₂OH |

1 = (1,1-c-Pr)O
2 = O(1,1-c-Pr)

TABLE II

ELEMENTAL ANALYSES

| EX. | FORMULA | CALCULATED | | | FOUND | | |
|---|---|---|---|---|---|---|---|
| | | C | H | N | C | H | N |
| 96 | C₃₁H₃₀Cl₂NO₄SNa.0.5H₂O | 60.49 | 5.08 | 2.28 | 60.75 | 5.07 | 2.33 |
| 124 | C₃₂H₃₃ClNO₄SNa.1.2H₂O | 63.24 | 5.87 | 2.30 | 63.12 | 5.68 | 2.29 |
| 131 | C₃₃H₃₅ClNO₄SNa.0.3H₂O | 65.45 | 5.93 | 2.31 | 65.45 | 6.23 | 2.10 |
| 158 | C₃₄H₃₅ClNO₄SNa.2.0H₂O | 63.06 | 6.02 | 2.16 | 63.26 | 6.15 | 2.12 |

METHODS OF SYNTHESIS

Compounds of the present invention can be prepared according to the following methods. Temperatures are in degrees Celsius.

Method A

Bromoacid II is treated with 2 equivalents of a base such as n-butyllithium in a suitable solvent such as THF at $-100°$ C., then at $-78°$ C. to afford III, which is reacted with IV (see EP 318,093, May 31, 1989 and U.S. Pat. No. 4,851,409, Jul. 25, 1989) to yield the hydroxyacid V. V is then esterified using conditions such as methanol/HCl, $CH_2N_2$ or $MeI/K_2CO_3$ and an organometallic reagent is then added to give the diol VI. The benzylic alcohol of VI is then reacted with the thiol IX by: (1) making the chloride by reaction with methanesulfonyl chloride in the presence of triethylamine, and (2) substituting the chloride by the thiol IX in the presence of a base such as sodium hydride or cesium carbonate to afford VII. In the cases where $Q^1$ is an ester, hydrolysis with a base such as NaOH, LiOH or $K_2CO_3$ (followed by acidification) affords the acid VIII. VII and VIII are both representatives of structure I.

Method B

The ketone IV is reduced to the benzylic alcohol using a reagent such as $NaBH_4$. This benzylic alcohol is converted to the benzylic bromide, using conditions such as carbon tetrabromide/1,2-bis-(diphenylphosphino)ethane, and treatment with triphenylphosphine affords the phosphonium salt X. Using a base such as potassium hexamethyldisilazide, the ylid of X is formed and is added to a lactol. Oxidation of the benzylic alcohol so obtained using conditions such as (1) $MnO_2$ in EtOAc and (2) $MnO_2/HCN/MeOH$ affords the ester XI. The thiol IX is then added to XI using a Lewis acid such as $AlCl_3$ or $TiCl_4$ to give the thioether XII. Reaction of XII with an organometallic compound such as a lithium or a magnesium salt, yield, in the cases where $Q^1$ is stable in these conditions, the tertiary alcohol XIII, which is a representative of structure I.

Method C

The enol acetate of XIV is obtained from the heating of XIV in isopropenyl acetate in the presence of an acid. Ozolysis of this enol ester yields the aldehyde XV. Starting from a bromophenol, protection of the alcohol and addition of a reagent such as butyllithium, lithium or magnesium afford the organometallic XVI, which is reacted with XV to give the hydroxyacid XVII. XVII is reacted with another organometallic and the reaction mixture is quenched with chlorotrimethylsilane. Deprotection of the phenol is done by using a reagent such as tetrabutylammonium fluoride in the case of silyl ether or pyridinium p-toluenesulfonate when P is a 2-tetrahydropyranyl group. Reaction of that phenol with a 2-(bromomethyl)quinoline derivative in the presence of $K_2CO_3$ yields the hydroxyketone XVIII. The benzylic alcohol is then reacted with methanesulfonyl chloride in the presence of a base such as triethylamine. The mesylate so obtained is substituted by the thiolate derivative of IX to afford XIX. Finally, an organometallic reaction or a reduction using a reagent such as $NaBH_4$ on XIX gave the alcohol XX. Using this method, two different R groups can be added to give a secondary or an unsymmetrical tertiary alcohol.

Method D

The hydroxyacid XVII is cyclized to the lactone using a reagent such as 2-chloro-N-methylpyridinium iodide. Deprotection of the phenol and coupling to the (bromomethyl)quinoline derivative as in Method C afford the lactone XXI. An organometallic reagent is then added to XXI to give the diol XXII. Finally, the secondary alcohol is substituted by the thiol IX as in Method C to yield the thioether XX.

Method E

The aldehyde XXIII, a derivative of IV, is reacted with an organometallic reagent and the benzylic alcohol so obtained is oxidized to XXIV with an oxidant like activated manganese dioxide. XXIV is then reacted with the iodide XXV in the presence of a base such as lithium diisopropylamide to yield the alkylation product XXVI. Reduction with sodium borohydride or addition of an organometallic reagent afford the hydroxyester XXVII, which is then treated as the lactone XXI in Method D to give the thioether XXVIII.

Method F

The enolate of the ketone XXIX, obtained by treatment of XXIX with a base such as KH or NaH, is reacted with dimethylcarbonate to yield the ketoester XXX. XXX is enolized with a base such as NaH and treated with the iodide XXXI, the methyl ester of XXV. The adduct so obtained is then decarboxylated using conditions such as heating with HCl in acetic acid to afford a mixture of the ester XXXII and the corresponding acid. Esterification of the mixture, using a reagent such as diazomethane, yields XXXII, which is then converted to XXXIII as described in Method G.

Method G

The hydroxyester XVII is esterifid using conditions such as heating with MeI and $K_2CO_3$ or reacting with diazomethane. Treatment of this hydroxyester with an oxidant such as pyridinium chlorochromate or activated manganese dioxide affords the ketoester XXXIV. The ketone is then reduced using the chiral oxazaborolidine XXXV in the presence of borane/THF complex. Reaction of the ester with an organometallic, deprotection of the phenol and reaction with a (bromomethyl)-quinoline derivative as in Method C gave the diol XXXVI, which is chiral XXII. Protection of the secondary alcohol with tert-butylchlorodiphenylsilane in the presence of a base such as 4-(dimethylamino)pyridine, protection of the tertiary alcohol as the 2-tetrahydropyranyl ether and removal of the silyl ether afford XXXVII. The chiral center of XXXVII can be inverted to give XXXVIII using conditions such as: (1) treatment with triphenylphosphine, diethyl azodicarboxylate and an acid such as R-(—)α-methoxyphenylacetic acid (chiral acid improves the resolution), and (2) hydrolysis of the ester so obtained with a base such as NaOH. Formation of the mesylate and substitution with the thiol IX as in Method C, followed by hydrolysis of the 2-tetrahydropyranyl ether using conditions such as pyridinium p-toluenesulfonate in methanol afford the thioethers XXXIXa and XXXIXb.

Method H

The phenylacetic acid XL is reduced to the alcohol XLI using a reagent such as borane in tetrahydrofuran. Formation of the alcoholate with one equivalent of a Grignard reagent, followed by treatment with magnesium afford the dimagnesium salt of XLI. It is added to a ketone or an aldehyde to yield the alcohol XLII. The bromide XLIII is then formed using conditions such as (1) formation of the mesylate with methanesulfonyl chloride and triethylamine and (2) substitution of the mesylate by sodium bromide in N,N-dimethyl formamide. The dimagnesium salt of XLIII is then formed as previously described and added to the ketone IV. The adduct XLIV is then reacted with the thiol IX as in Method C to yield XLV.

Method I

The ketoester XXX is treated with the iodide XLVI and decarboxylated as in Method F. Reduction of the ketone with a reagent such as $NaBH_4$ yields the alcohol XLVII. By reaction with an organometallic in toluene, the nitrile XLVII is converted to the amine XLVIII. The thiol IX is then added as in Method C to afford XLIX. Reaction of an iodide with the amine XLIX gives a secondary or tertiary amine L. Both XLIX and L are representatives of structure I.

Method J

Vinylmagnesium bromide or allylmagnesium bromide is added to the aldehyde derivative of IV to yield LI. Using the procedure of R. C. Larock et al. (Tetrahedron Letters, 30 6629 (1989)), the aryl halogenide LII is coupled to the alcohol LI to give LIII. When $Q^3$ is an ester or an alcohol, LIII can be converted to LIV or its isomer, a structure representative of Ia, using the procedure of Method G. Also, when $Q^3$ is $Q^1$, chiral reduction of the ketone LIII with XXXV as in Method G followed by formation of the mesylate and substitution by the thiol LV affords LVI, a structure representative of Ib.

In the following schemata

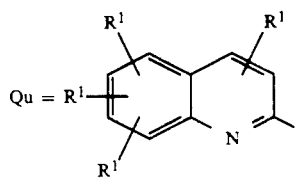

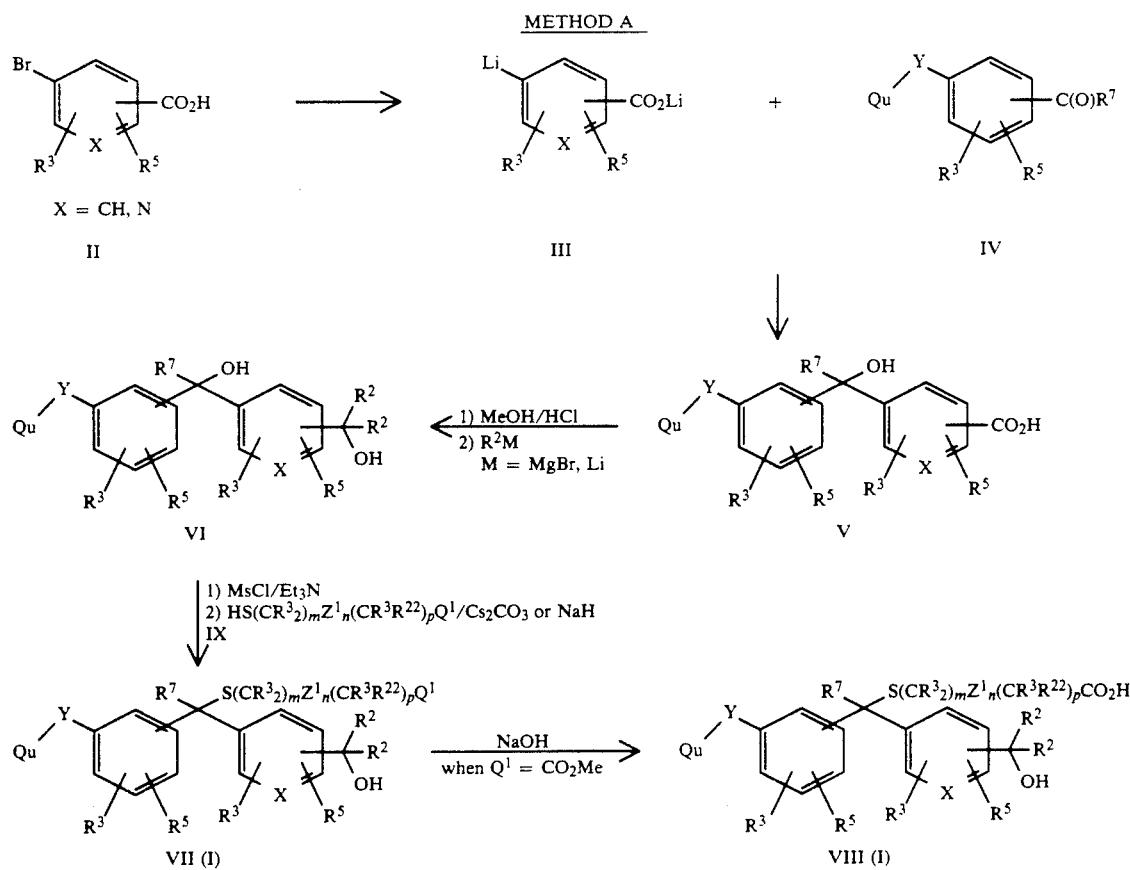

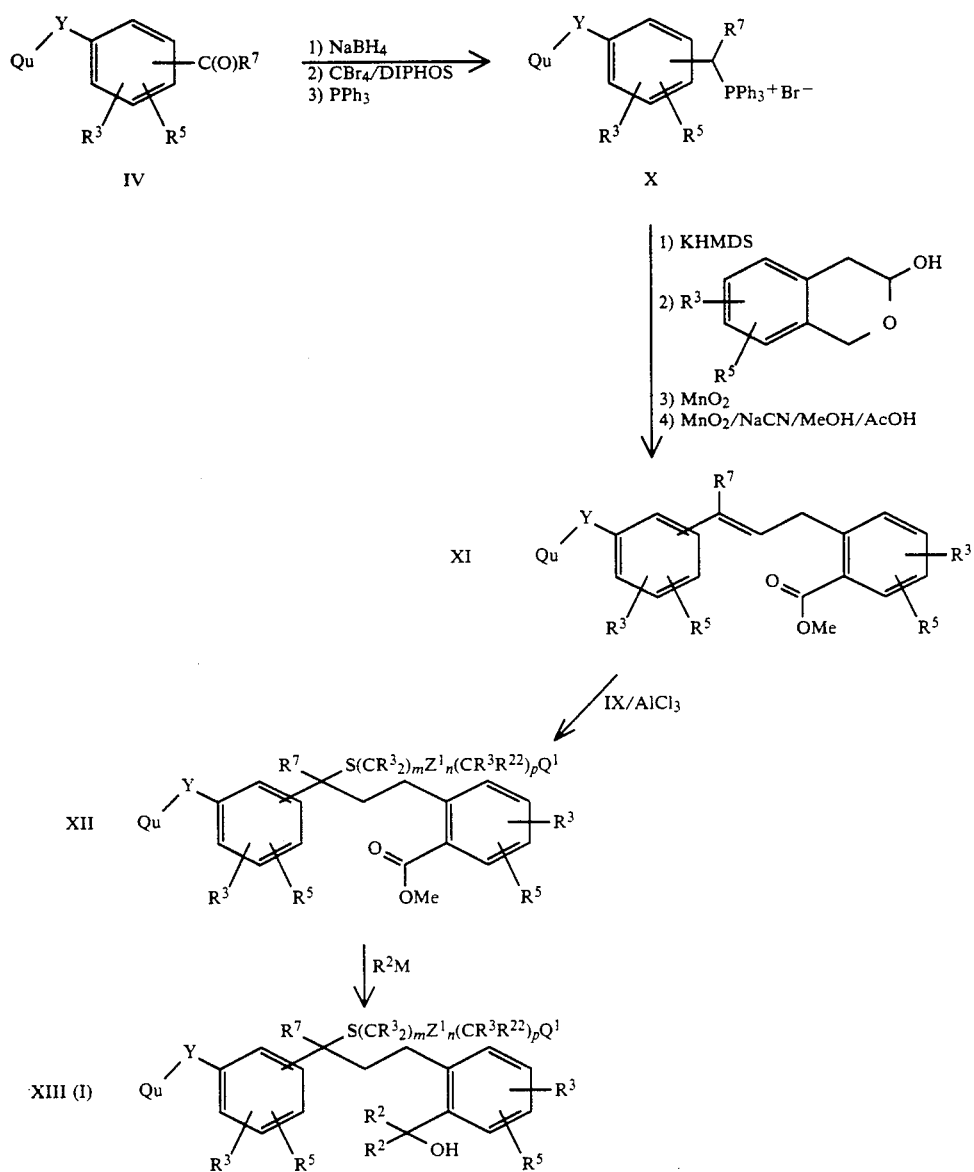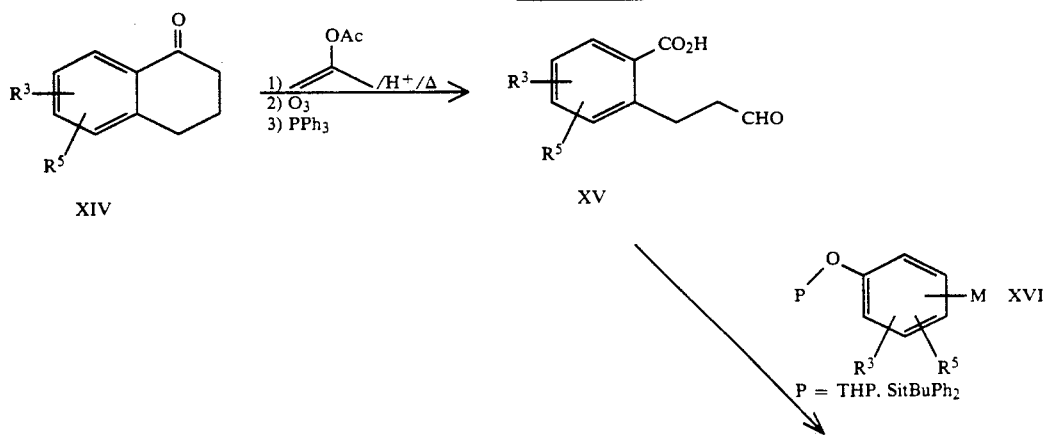

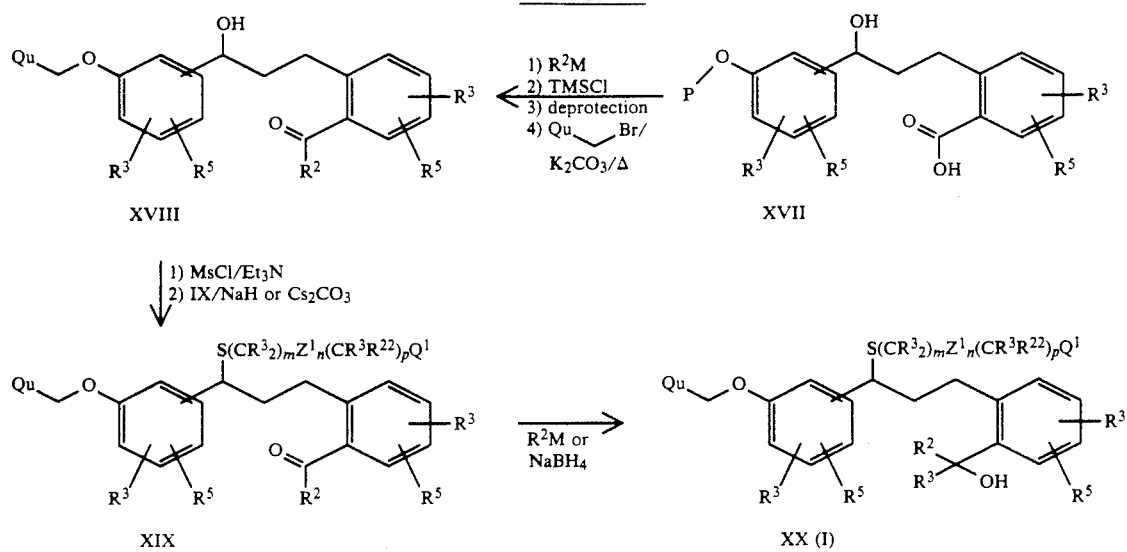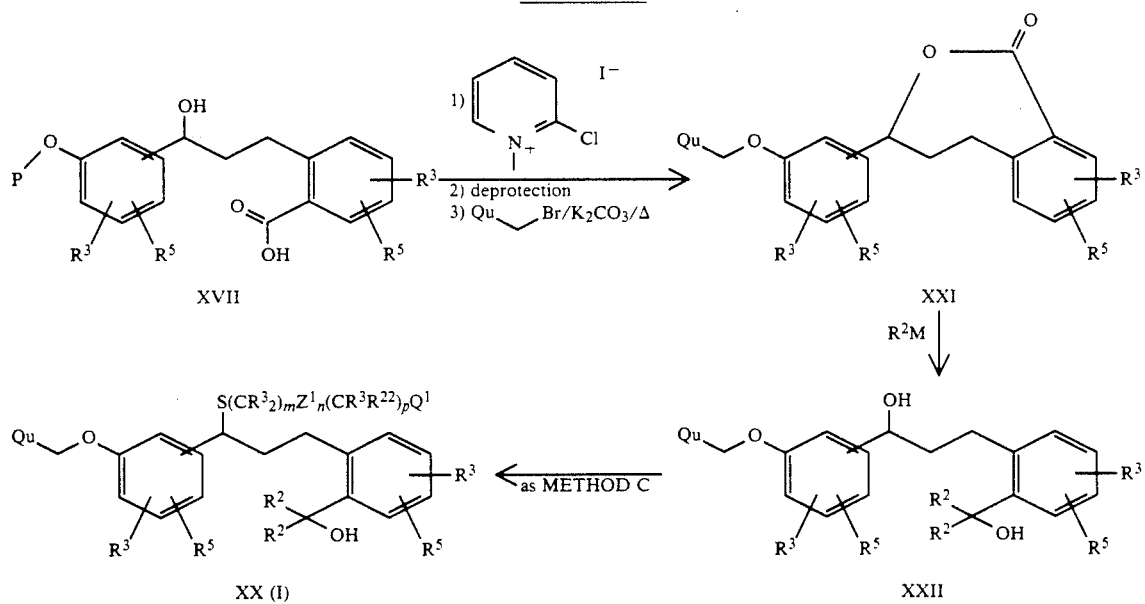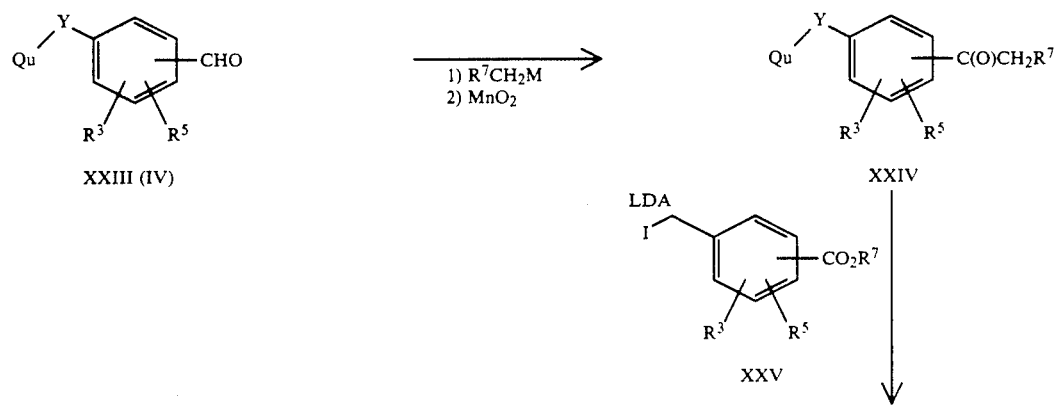

-continued
METHOD E
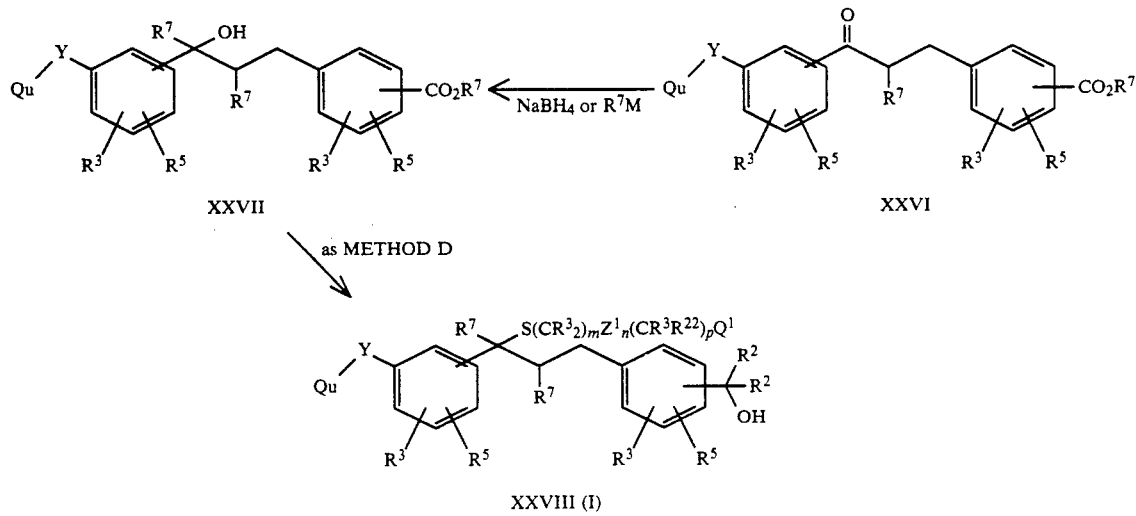
METHOD F
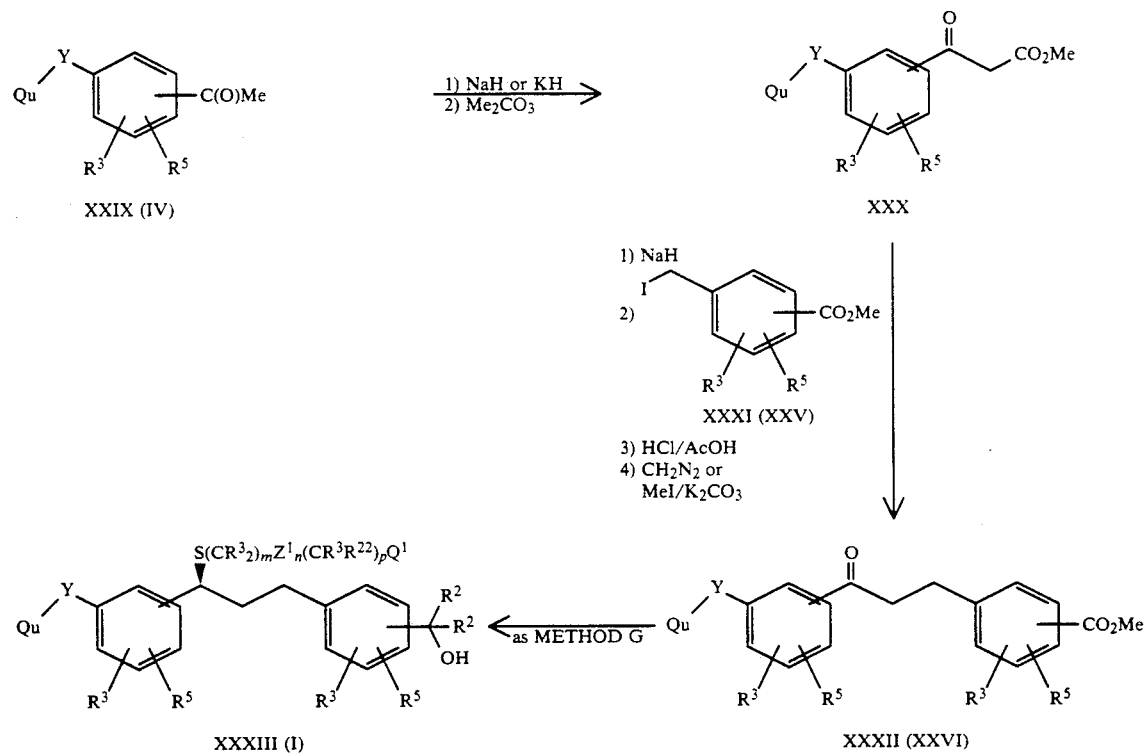
METHOD G
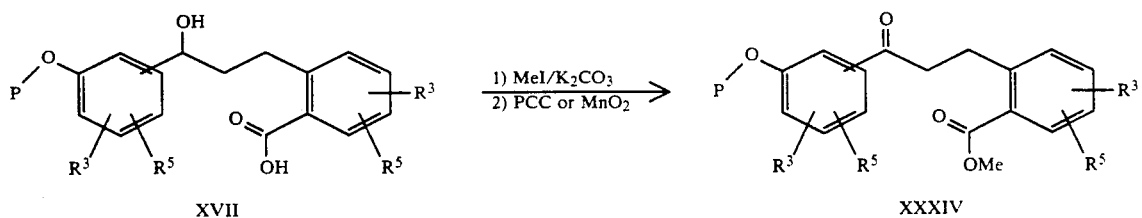

-continued
METHOD G
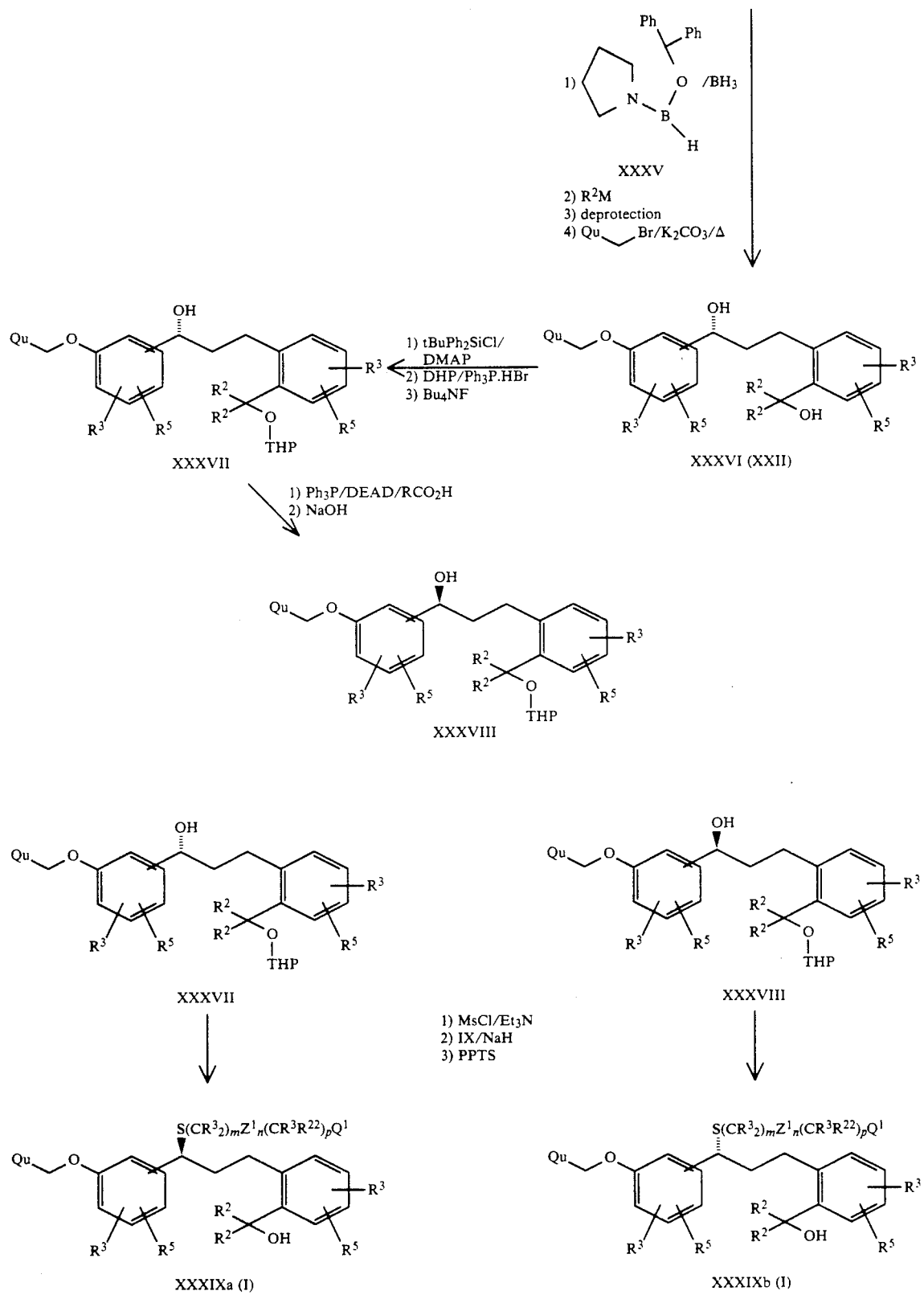

METHOD H
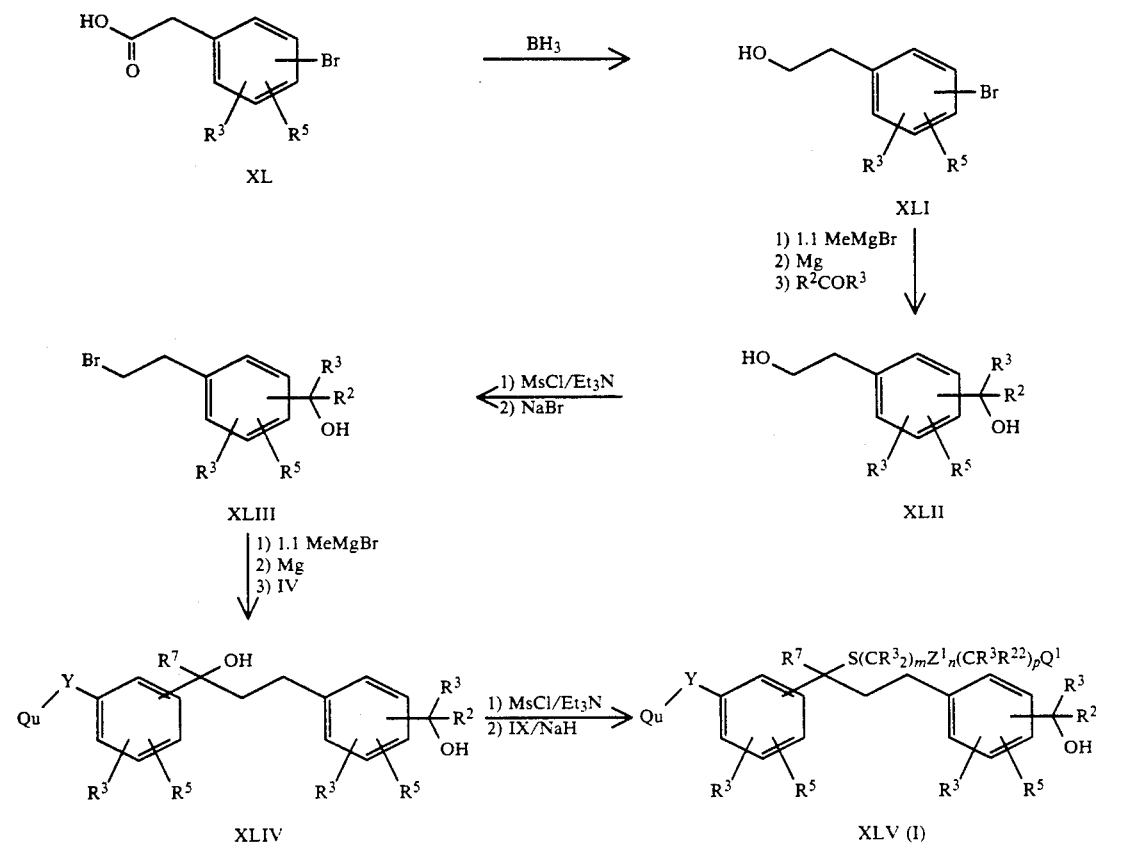
METHOD I
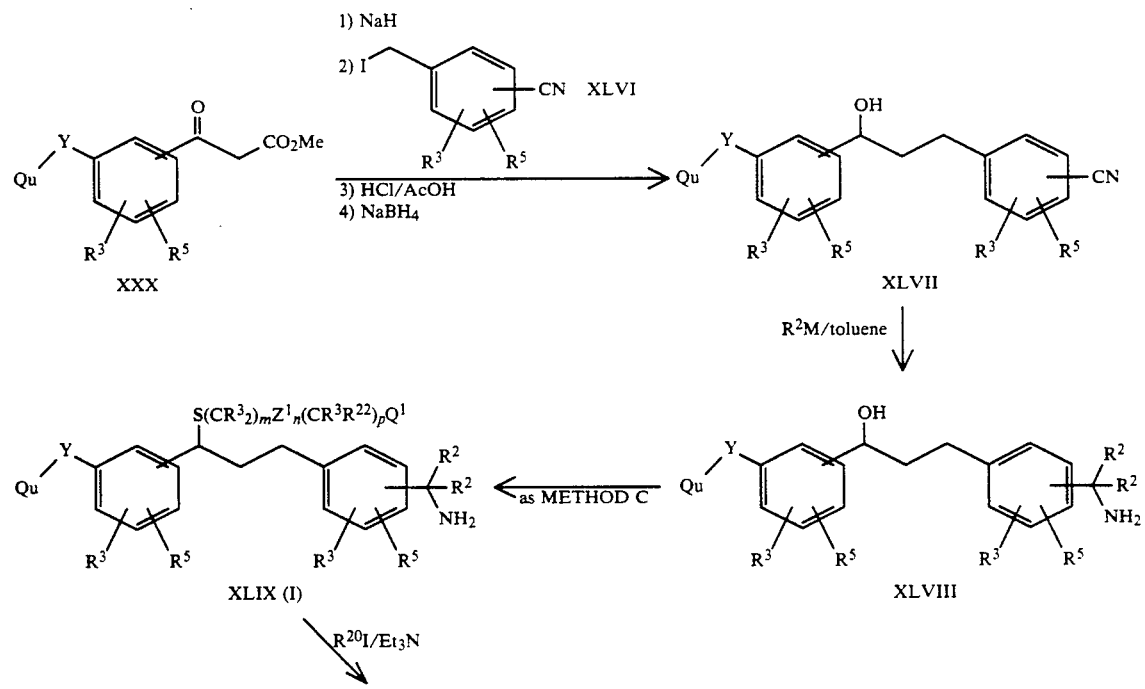

-continued
METHOD I
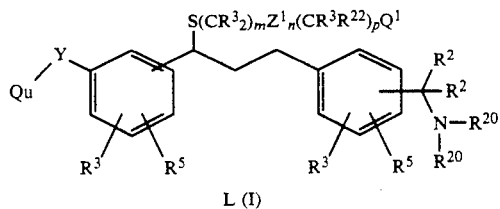
L (I)
METHOD J
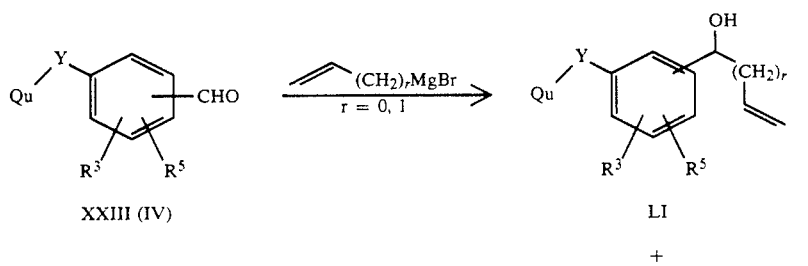
XXIII (IV)            LI
+
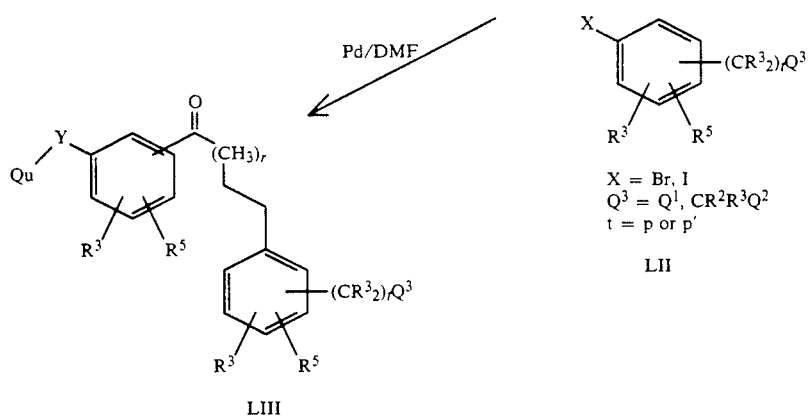
$X = Br, I$
$Q^3 = Q^1, CR^2R^3Q^2$
$t = p$ or $p'$
LII
LIII
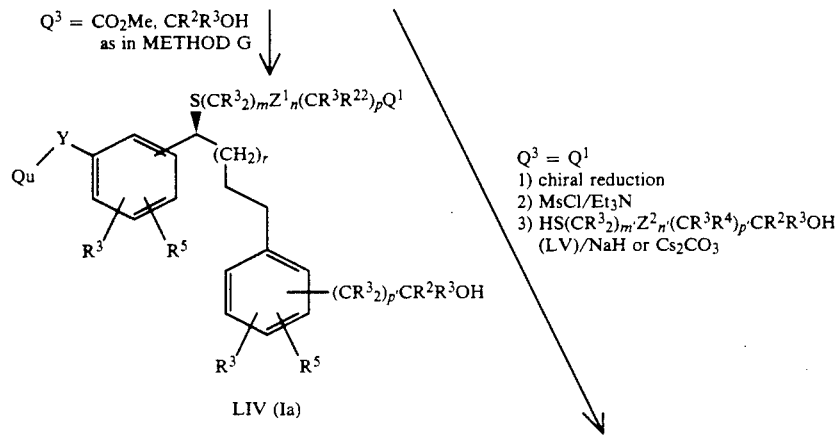
LIV (Ia)
$Q^3 = Q^1$
1) chiral reduction
2) MsCl/Et$_3$N
3) HS(CR$^3{}_2$)$_{m'}$·Z$^2{}_{n'}$·(CR$^3$R$^4$)$_{p'}$·CR$^2$R$^3$OH
   (LV)/NaH or Cs$_2$CO$_3$ -continued
METHOD J

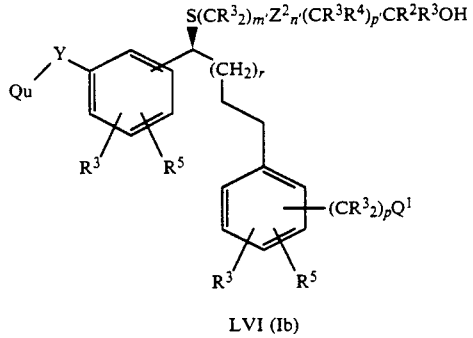

LVI (Ib)

ASSAYS FOR DETERMINING BIOLOGICAL ACTIVITY

Compounds of Formula I can be tested using the following assays to determine their mammalian leukotriene antagonist activity and their ability to inhibit leukotriene biosynthesis.

The leukotriene antagonist properties of compounds of the present invention were evaluated using the following assays.

LTD$_4$ RECEPTOR BINDING STUDIES IN GUINEA PIG LUNG MEMBRANES, GUINEA PIG TRACHEA AND IN VIVO STUDIES IN ANESTHETIZED GUINEA PIGS

A complete description of these three tests is given by T. R. Jones et al., Can. J. Physiol. Pharmacol., 67, 17–28 (1989).

Compounds of Formula I were tested using the following assays to determine their mammalian leukotriene biosynthesis inhibiting activity.

DETERMINATION OF INHIBITION OF 5-LIPOXYGENASE

The activity of 5-lipoxygenase was measured from the conversion of [$^{14}$C]-arachidonic acid to 5-HETE and 5,12-diHETEs catalyzed by the 10,000×g supernatant fraction from rat PMN leukocytes, using the procedure of Riendeau and Leblanc (*Biochem. Biophys. Res. Commun.*, 141, 534–540, (1986)) with minor modifications. The incubation mixture contained 25 mM Na+/K+ phosphate buffer, pH 7.3, 1 mM ATP, 0.5 mM CaCl$_2$, 0.5 mM mercaptoethanol and an aliquot of the enzyme preparation in a final volume of 0.2 ml. The enzyme was pre-incubated with the inhibitor for 2 min at 37° C. before initiation of the reaction with the addition of 2 ml of [$^{14}$C]-arachidonic acid (25,000 DPM) in ethanol to obtain a final concentration of 10 mM. Inhibitors were added as 500-fold concentrated solutions in DMSO. After incubation for 10 min at 37° C., the reaction was stopped by adding 0.8 mL of diethyl ether/methanol/1M cirtric acid (30:4:1). The samples were centrifuged at 1,000×g for 5 min and the organic phases analyzed by TLC on Baker Si250F-PA to Whatman silica gel 60A LKGF plates using diethyl ether/petroleum ether/acetic acid (50:50:1) as solvent. The amount of radioactivity migrating at the positions of arachidonic acid, 5-HETE and 5,12-diHETEs was detemrined using a Berthold TLC analyzer LB 2842. The activity of 5-lipoxygenase was calculated from the percentage of conversion of arachidonic acid to 5-HETE and 5,12-diHETs after the 10 min incubation.

HUMAN POLYMORPHONUCLEAR (PMN) LEUKOCYTE LTB$_4$ ASSAY

A. Preparation of Human PMN

Human blood was obtained by antecubital venepuncture from consenting volunteers who had not taken medication within the previous 7 days. The blood was immediately added to 10% (v/v) trisodium citrate (0.13M) or 5% (v/v) sodium heparin (1000 IU/mL). PMNs were isolated from anticoagulated blood by dexran semidmenation of erythrocytes followed by centrifugation through Ficoll-Hypaeque (specific gravity 1.077), as described in Boyyum.[1] Contaminating erythrocytes were removed by lysis following exposure to ammonium chloride (0.16M) in Tris buffer (pH 7.65), and the PMNs resuspended at 5×10$^5$ cells/mL in HEPES (15 mM)-buffered Hanks balanced salt solution containing Ca$^{2+}$ (1.4 mM) and Mg$^{2+}$ (0.7 mM), pH 7.4. Viability was assessed by Trypan blue exclusion and was typically greater than 98%.

(1) Boyum, A. Scand. J. Clin. Lab. Invest., (21 (Supp 97), 77 (1968).

B. Generation and Radioimmunoassay of LTB$_4$

PMNs (0.5 mL; 2.5×10$^5$ cells) were placed in plastic tubes and incubated (37° C., 2 min) with test compounds at the desired concentration or vehicle (DMSO, final concentration 0.2%) as control. The synthesis of LTB$_4$ was initiated by the addition of calcium ionophore A23187 (final concentration 10 mM) or vehicle in control samples and allowed to proceed for 5 minutes at 37° C. The reactions were then terminated by the addition of cold methanol (0.25 mL) and samples of the entire PMN reaction mixture were removed for radioimmunoassay of LTB$_4$.

Samples (50 mL) of authentic LTB$_4$ of known concentration in radioimmunoassay buffer (RIA) buffer (potassium phosphate 1 mM; disodium EDTA 0.1 mM; Thimerosal 0.025 mM; gelatin 0.1%, pH 7.3) or PMN reaction mixture diluted 1:1 with RIA buffer were added to reaction tubes. Thereafter [$^3$H]-LTB$_4$ (10 nCi in 100 mL RIA buffer) and LTB$_4$-antiserum (100 mL of a 1:3000 dilution in RIA buffer) were added and the tubes vortexed. Reactants were allowed to equilibrate by incubation overnight at 4° C. To separate antibody-bound from free LTB$_4$, aliquots (50 mL) of activated charcoal (3% activated charcoal in RIA buffer containing 0.25% Dextran T-70) were added, the tubes vortexed, and allowed to stand at room temperature for 10 minutes prior to centrifugation (1500×g; 10 min; 4° C.). The supernatants containing antibody-bound LTB$_4$ were decanted into vials and Aquasol 2 (4 mL) was added. Radioactivity was quantified by liquid scintillation spectrometry. Preliminary studies established that the amount of methanol carried into the radioimmunoassay did not influence the results. The specificity of the antiserum and the sensitivity of the procedure have been described by Rokach et al.[2] The amount of $LTB_4$ produced in test and control (approx. 20 ng/$10^6$ cells) samples were calculated. Inhibitory dose-response curves were constructed using a four-parameter algorithm and from these the $IC_{50}$ values were determined.

(2) Rokach, J.; Hayes, E. C.; Girard, Y.; Lombardo, D. L.; Maycock, A. L.; Rosenthal, A. S.; Young, R. N.; Zamboni, R.; Zweerink, H. J. *Prostaglandins Leukotrienes and Medicine*, 13, 21 (1984).

Compounds of Formula I were tested in the following assays to determine their in vivo activity as both leukotriene antagonist and leukotriene biosynthesis inhibitor.

ASTHMATIC RAT ASSAY

Rats are obtained from an inbred line of asthmatic rats. Both female (190-250 g) and male (260-400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate was supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a Devilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 postsensitization. In order to eliminate the serotonin component of the response, rats are pretreated intravenously 5 minutes prior to aerosol challenge with 3.0 mgm/kg of methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1-4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

PULMONARY MECHANICS IN TRAINED CONSCIOUS SQUIRREL MONKEYS

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65HG, 400 cps) and given in a volume of 1 ml/kg body weight. For aerosol administraiton of compounds, a DeVilbiss ultrasonic nebulizer is utilized. Pretreatment periods vary from 5 minutes to 4 hours before the monkeys are challenged with aerosol doses of either leukotriene $D_4$ ($LTD_4$) or Ascaris antigen.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of $LTD_4$ or Ascaris antigen response by the test compound. For statistical analysis, paired t-test is used. (References: McFarlane, C. S. et al., *Prostaglandins*, 28, 173-182 (1984) and McFarlane, C. S. et al., *Agents Actions* 22, 63-68 (1987)).

PREVENTION OF INDUCED BRONCHOCONSTRICTION IN ALLERGIC SHEEP

A. Rationale:

Certain allergic sheep with known sensitivity to a specific antigen (*Ascaris suum*) respond to inhalation challenge with acute and late bronchial responses. The time course of both the acute and the late bronchial responses approximates the time course observed in asthmatics and the pharmacological modification of both responses is similar to that found in man. The effects of antigen in these sheep are largely observed in the large airways and are conveniently monitored as changes in lung resistance or specific lung resistance.

B. Methods:

Animal Preparation: Adult sheep with a mean weight of 35 kg (range, 18 to 50 kg) are used. All animals used meet two criteria: a) they have a natural cutaneous reaction to 1:1,000 or 1:10,000 dilutions of *Ascaris suum* extract (Greer Diagnostics, Lenois, N.C.) and b) they have previously responded to inhalation challenge with *Ascaris suum* with both an acute bronchoconstriction and a late bronchial obstruction (Abraham, W. M., Delehunt, J. C., Yerger, L. and Marchette, B., Am. Rev. Resp. Dis., 128, 839-44 (1983)).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one ml of air), which is positioned such that inspiration produces a negative pressure deflection with clearly discernible cardiogenic oscillations. Lateral pressure in the trachea is measured with a sidehole catheter (inner dimensions, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). Testing of the pressure transducer catheter system reveals no phase shift between pressure and flow to a frequency of 9 Hz. For the measurement of pulmonary resistance ($R_L$), the maximal end of the nasotracheal tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_L$ from transpulmonary pressure, respiratory volume obtained by integration and flow. Analysis of 10–15 breaths is used for the determination of $R_L$. Thoracic gas volume ($V_{tg}$) is measured in a body plethysmograph, to obtain specific pulmonary resistance ($SR_L = R_L \cdot V_{tg}$).

Aerosol Delivery Systems: Aerosols of *Ascaris suum* extract (1:20) are generated using a disposable medical nebulizer (Raindrop®, Puritan Bennett), which produces an aerosol with a mass median aerodynamic diameter of 6.2 μM (geometric standard deviation, 2.1) as determined by an electric size analyzer (Model 3030; Thermal Systems, St. Paul, Minn.). The output from the nebulizer is directed into a plastic t-piece, one end of which is attached to the nasotracheal tube, the other end of which is connected to the inspiratory part of a Harvard respirator. The aerosol is delivered at a tidal volume of 500 ml of a rate of 20 per minute. Thus, each sheep receives an equivalent dose of antigen in both placebo and drug trials.

Experimental Protocol: Prior to antigen challenge baseline measurements of $SR_L$ are obtained, infusion of the test compound is started 1 hr prior to challenge, the measurement of $SR_L$ repeated and then the sheep undergoes inhalation challenge with *Ascaris suum* antigen. Measurements of $SR_L$ are obtained immediately after antigen challenge and at 1, 2, 3, 4, 5, 6, 6.5, 7, 7.5 and 8 hr after antigen challenge. Placebo and drug tests are separated by at least 14 days. In a further study, sheep are given a bolus dose of the test compound followed by an infusion of the test compound for 0.5–1 hr prior to ascaris challenge and for 8 hr after ascaris as described above.

Statistical Analysis: A Kruskal-Wallis one way ANOVA test was used to compare the acute immediate responses to antigen and the peak late response in the controls and the drug treated animals.

The invention is further defined by reference to the following examples, which are intended to be illustrative and not limiting. All temperatures are in degrees Celsius.

EXAMPLE 1

Sodium 3-((1-(3-((7-chloro-2-quinolinyl)methoxy)phenyl)-3-(2-(2-hydroxy-2-propyl)phenyl)propyl)thio)-2-methylpropanoate

Method A

Step 1: 3-((7-chloro-2-quinolinyl)methoxy)benzaldehyde

A suspension of 7-chloro-2-(bromomethyl)quinoline (50.5 g, 197 mmol, EP 233,763, Example 4, Step 1), 3-hydroxybenzaldehyde (22.9 g, 188 mmol) and $K_2CO_3$ (51.7 g, 375 mmol) in 600 mL of acetone was heated to reflux for 2 h. After cooling down, 200 mL of $CH_2Cl_2$ was added and the mixture was filtered through celite with acetone:$CH_2Cl_2$ 3:1. The title product was purified by flash chromatography on silica with EtOAc:toluene 5:95 to yield 46.64 g, 83%. (Alternatively, the product may be purified by a swish in ether:hexane 7:1).

$^1$H NMR ($CD_3COCD_3$): δ 5.47 (2H, s), 7.40 (1H, m), 7.53–7.64 (4H, m), 7.78 (1H, d), 8.03 (1H, d), 8.05 (1H, d), 8.43 (1H, d), 10.00 (1H, s).

Step 2: 3-((7-chloro-2-quinolinyl)methoxy)benzenemethanol

The aldehyde of Step 1 (46.64 g, 156.6 mmol) was dissolved in 300 mL of THF. At 0° C., 800 mL of EtOH was added, followed by $NaBH_4$ (5.93 g, 157 mmol). The mixture was then stirred at r.t. (room temperature) for 1 h and poured into cold 25% aq (aqueous) $NH_4OAc$. The organic solvents were evaporated and the title alcohol was extracted with toluene:THF 1:1, dried over $Na_2SO_4$ and filtered through silica to yield 47.9 g of the title compound.

Step 3: 2-((3-(bromomethyl)phenoxy)methyl)-7-chloroquinoline

To the benzylic alcohol of Step 2 (47.0 g, 157 mmol) and $CBr_4$ (60.08 g, 181 mmol) in $CH_2Cl_2$ (750 mL) at 0° C., a solution of 1,2-bis(diphenylphosphino) ethane (DIPHOS, 36.29 g, 91.1 mmol) in $CH_2Cl_2$ (350 mL) was added and the resulting mixture was stirred at 0° C. for 45 min. and at r.t. for 30 min. Ether was then added and the mixture was filtered through a pad of silica and the silica was washed with EtOAc:toluene 20:80 to yield 40.35 g (70%) of the pure title compound.

$^1$H NMR ($CD_3COCD_3$): δ4.62 (2H, s), 5.40 (2H, s), 7.04 (1H, d), 7.08 (1H, d), 7.21 (1H, s), 7.30 (1H, t), 7.60 (1H, dd), 7.76 (1H, d), 8.02 (1H, d), 8.05 (1H, s), 8.42 (1H, d).

Step 4: ((3-((7-chloro-2-quinolinyl)methoxy)phenyl)methyl)triphenylphosphonium bromide The bromide of Step 3 (26.45 g, 72.9 mmol) and triphenylphosphine (28.7 g, 109 mmol) were heated to reflux in $CH_3CN$ (250 mL) for 7 hours. At r.t., ether was added and an oil separated, which crystallized on trituration. The solid was filtered and was swished with ether for 20 hours to yield 44.87 g (98%) of the title phosphonium salt.

$^1$H NMR ($CD_3COCD_3$/$CD_3SOCD_3$): δ5.15 (2H, s), 5.23 (2H, d), 6.69 (1H, d), 6.77 (1H, s), 7.02 (1H, d), 7.19 (1H, dd), 7.56 (1H, d), 7.62–7.80 (13H, m), 7.85–7.95 (3H, m), 8.04 (1H, s), 8.08 (1H, d), 8.48 (1H, d).

Step 5: 2-(3-(3-((7-chloro-2-quinolinyl)methoxy)phenyl)-2-propenyl)benzenemethanol At −10° C., a solution of 0.65M KHMDS (potassium hexamethyldisilazide) in toluene (21 mL, 13.65 mmol) was added dropwise to a suspension of the phosphonium salt of Step 4 (8.457 g, 13.53 mmol) in THF (70 mL) and the mixture was stirred at 0° C. for 30 min. At −78° C., a solution of 1H-3-hydroxy-3,4-dihydrobenzo(c)pyran (1.141 g, 7.60 mmol) in THF (14 mL) was added slowly. The mixture was allowed to warm to r.t. and was stirred for a further 3 hours. Aqueous NH₄OAc 25% was added and the products were extracted with EtOAc, dried over Na₂SO₄ and purified by flash chromatography on silica using EtOAc:toluene 10:90 and 15:85. The title compound (2.84 g, 90% yield) was obtained as a cis:trans mixture and was used as such for the next step.

¹H NMR (CD₃COCD₃): δ 3.60 (2H, d), 4.55 and 4.72 (2H, s), 5.37 (2H, s), 5.75 and 6.35-6.57 (2H, m), 6.91 (1H, d), 6.99 (1H, d), 7.12-7.30 (5H, m), 7.43 (1H, m), 7.60 (1H, d), 7.73 (1H, d), 8.00 (2H, m), 8.40 (1H, d).

Step 6: 2-(3-(3-((7-chloro-2-quinolinyl)methoxy)-phenyl)-2-propenyl)benzaldehyde To a solution of the benzylic alcohol of Step 5 (2.899 g, 6.20 mmol) in EtOAc (120 mL) was added portionwise activated MnO₂ (10.15 g, 114 mmol) and the reaction was followed by TLC (EtOAc:toluene 7.5:92.5). When the reaction was completed (approximately 2 h), the mixture was filtered through silica, concentrated, and the title product was purified by flash chromatography on silica using EtOAc:toluene 2.5:97.5. Yield 2.18 g, 85%.

¹H NMR (CD₃COCD₃): δ 4.00 (2H, d), 5.35 (2H, s), 5.72 and 6.30-6.60 (2H, m, cis:trans mixture), 6.90-8.10 (12H, m), 8.39 (1H, d), 10.33 (1H, s).

Step 7: Methyl 2-(3-(3-((7-chloro-2-quinolinyl)methoxy)phenyl)-2-propenyl)benzoate To a solution of the aldehyde of Step 6 (17.26 g, 41.7 mmol) in 1.5 L of MeOH:THF 2:1, NaCN (20 g, 408 mmol), AcOH (5.7 mL, 98.9 mmol) and activated MnO₂ (90 g, 1.01 mol) were added and the mixture was stirred for 16 h. The inorganic solid was then removed by filtration and washed with EtOAc. To the combined organic phases, 25% aq NH₄OAc (1.7 L) was added. The two phases were separated and the aqueous layer was reextracted with EtOAc. The organic phases were washed with brine and dried over Na₂SO₄. Flash chromatography of the residue on silica with toluene and EtOAc:toluene 2.5:97.5 afforded 15.63 g (84%) of the title ester.

¹H NMR (CD₃COCD₃): δ 3.70 and 3.82-3.95 (5H, m, cis:trans mixture), 5.38 (2H, 2s), 5.70 and 6.47 (2H, 2m), 6.87-8.05 (12H, m), 8.38 (1H, 2d).

Step 8: 3-((1-(3-((7-chloro-2-quinolinyl)methoxy)-phenyl)-3-(2-(methoxycarbonyl)phenyl)propyl)thio)-2-methylpropanoic acid At −10° C., AlCl₃ (2.437 g, 18.3 mmol) was added to a solution of the styrene of Step 7 (1.013 g, 2.28 mmol) and 3-mercapto-2-methylpropanoic acid (356 mg, 2.96 mmol, obtained from the hydrolysis of ethyl 3-mercapto-2-methylpropanoate (Example 1, Method B, Step 6) as in Example 7, Step 4, or alternatively from the NaOH hydrolysis of ethyl 3-(acetylthio)-2-methylpropanoate) in 25 mL of CH₂Cl₂ and the mixture was stirred at 0° C. in the dark for 2 h. Cold aq NH₄OAc, EtOAc and THF were then added and the mixture was stirred until complete dissolution of the oil. The product was extracted with EtOAc:THF 1:1, dried over Na₂SO₄ and concentrated. The sodium salt of the acid was formed in EtOH with 500 μl of 10N NaOH. It was purified on an Amberlite ion exchange resin XAD-8: elution with water separate the sodium 3-mercapto-2-methyl-propanoate and elution with methanol afforded the title acid as an impure sodium salt. The compound was dissolved in saturated aq NH₄Cl, extracted with EtOAc:THF 1:1, dried over Na₂SO₄ and purified by flash chromatography on silica using acetone:toluene:acetic acid 5:95:1 to yield 766 mg (60%) of the title acid.

¹H NMR (CD₃COCD₃): δ 1.12 (3H, 2d, mixture of diastereomers), 2.12 (2H, td), 2.30-3.08 (5H, m), 3.84 (3H, s), 3.95 (1H, dd), 5.45 (2H, s), 7.01 (2H, m), 7.16-7.36 (4H, m), 7.45 (1H, dd), 7.60 (1H, d), 7.78 (1H, d), 7.83 (1H, d), 8.00 (1H, d), 8.05 (1H, s), 8.42 (1H, d).

Step 9: 3-((1-(3-((7-chloro-2-quinolinyl)methoxy)-phenyl)-3-(2-(2-hydroxy-2-propyl)phenyl)propyl)thio)-2-methylpropanoic acid To the ester of Step 8 (626 mg, 1.11 mmol) dissolved in 10 mL of THF at 0° C., 1.5M MeMgBr (4.0 mL, 6.0 mmol) was added slowly and the mixture was stirred at 0° C. for 2 h and at r.t. for 2 h. At 0° C., aq saturated NH₄Cl was added and the product was extracted with EtOAc, dried over Na₂SO₄ and purified by flash chromatography on silica using acetone:toluene:AcOH 5:95:1 and 7.5:92.5:1. The pure title compound was finally obtained by HPLC on a μPorasil column (diameter: 12 mm; flow rate: 8.9 ml min⁻¹) using acetone:toluene:AcOH 5:95:1. Yield 246 mg, 39%.

¹H NMR (CD₃COCD₃): δ 1.10 (3H, 2d, mixture of diastereomers), 1.54 (6H, s), 2.16 (2H, m), 2.36 (1H, m), 2.46-2.87 (3H, m), 3.12 (1H, m), 4.00 (1H, dd), 5.42 (2H, s), 6.95-7.34 (7H, m), 7.40 (1H, m), 7.60 (1H, dd), 7.77 (1H, d), 8.01 (1H, d), 8.06 (1H, s), 8.43 (1H, d).

Step 10

To the acid of Step 9 (243 mg, 431 μmol) in 10 mL of EtOH was added 1.0N NaOH (430 μl). The solvents were evaporated and the product was freeze-dried to give 250 mg of the title compound as a yellowish solid.

Anal. calcd for C₃₂H₃₃ClNO₄SNa.H₂O: C, 63.61; H, 5.84; N, 2.32. Found: C, 63.40; H, 5.62; N, 2.37.

Method B

Step 1: 3,4-dihydro-1-naphthalenyl acetate

A mixture of α-tetralone (200 mL, 1.5 mol) and conc. H₂SO₄ (4 mL) in isopropenyl acetate (1.0 L, 9.08 mol) was heated to reflux overnight. It was cooled to r.t. and filtered through a mixture of celite, NaHCO₃ and silica (approx. 1:1:0.2) with EtOAc and concentrated to yield 317.1 g of the crude title product; bp: 90° C./0.5 mm Hg.

¹H NMR (CDCl₃): δ 2.30 (3H, s), 2.44 (2H, td), 2.87 (2H, t), 5.70 (1H, t), 7.10 (1H, m), 7.13-7.20 (3H, m).

Step 2: 2-(3-oxopropyl)benzoic acid

At −50° C., 200 mL of MeOH were added to a solution of the enol acetate of Step 1 (214 g, approx. 1.04 mol) in 800 mL of acetone. At −78° C., ozone was bubbled through this solution for 7 h (or until the excess of O₃ produced a green color). The excess of ozone was blown away by a stream of N₂ and a solution of triphenylphosphine (327 g, 1.25 mol) in 1 L of acetone was then added slowly at −78° C. The temperature was slowly raised to −10° C. over 30 min. 1N HCl (700 mL) was slowly added and the mixture was stirred at 3° C. for 16 h. The organic solvent were evaporated, 500 mL of EtOAc were added and the mixture was alkalinized with an excess of NaHCO₃ (approx. 270 g). The aqueous phase was washed with EtOAc (2×1 L) and the organic layers were reextracted with 1 L of saturated NaHCO₃ by agitation over 2 h. The combined aqueous extracts were then acidified with conc. HCl and extracted with EtOAc. The extract was dried over Na₂SO₄, the solvent was evaporated and the acetic acid was co-evaporated with toluene to yield 139.6 g of the title compound (75% for Steps 1 and 2) as a white solid.

$^1$H NMR (CDCl$_3$): δ 2.88 (2H, t), 3.36 (2H, t), 7.35 (2H, dd), 7.53 (1H, dd), 8.11 (1H, d), 9.86 (1H, s).

Step 3: 2(3-hydroxy-3-(3-(2-tetrahydropyranyloxy)-phenyl)propyl)benzoic acid

At −10° C., a solution of the aldehyde of Step 2 (5.045 g, 28.3 mmol) in 50 mL of THF was added dropwise to 0.57M 3-(2-tetrahydropyranyloxy)phenylmagnesium bromide in THF (120 mL, 68.4 mmol, prepared from 2-(3-bromophenoxy)tetrahydropyran and Mg in THF and filtered to remove the excess of Mg) and the mixture was stirred at r.t. for 30 min. At 0° C., 25% aq NH$_4$OAc was added. The title product was extracted with EtOAc, dried over Na$_2$SO$_4$ and purified by flash chromatography on silica using acetone:toluene:AcOH 5:95:1 and 15:85:1. Yield: 9.74 g, 97%.

$^1$H NMR (CDCl$_3$): δ 1.54–1.78 (3H, m), 1.78–2.20 (5H, m), 2.97–3.14 (2H, m), 3.62 (1H, m), 3.93 (1H, ddd), 4.74 (1H, t), 5.47 (1H, dt), 6.92–7.03 (2H, m), 7.08 (1H, br s), 7.20–7.33 (3H, m), 7.46 (1H, dd), 7.98 (1H, m).

Step 4: 3-(3-(2-acetylphenyl)-1-hydroxypropyl)-phenol

At 0° C., 1.5M MeLi (7.5 mL, 11.25 mmol) was added dropwise to a solution of the hydroxyacid of Step 3 (943 mg, 2.65 mmol) in 30 mL of THF and the mixture was stirred at 0° C. for an hour. At 0° C., freshly distilled TMSCl (chlorotrimethylsilane, 2.8 mL, 22.1 mmol) was added and the mixture was stirred at r.t. for an hour. At 0° C., 50 mL of 2N HCl were then added and the solution was stirred at r.t. for 1.5 h. The title product was extracted with EtOAc, dried over Na$_2$SO$_4$ and purified by flash chromatography on silica with acetone:toluene 10:90 and 15:85. Yield 436 mg, 61%.

$^1$H NMR (CD$_3$COCD$_3$): δ 1.94 (2H, td), 2.56 (3H, s), 2.97 (2H, m), 4.26 (1H, d, OH), 4.56 (1H, br t), 6.68 (1H, br d), 6.82 (1H, d), 6.88 (1H, br s), 7.12 (1H, dd), 7.30 (1H, dd), 7.32 (1H, d), 7.43 (1H, dd), 7.75 (1H, d), 8.21 (1H, s, OH).

Step 5: 3-(2-acetylphenyl)-1-(3-((7-chloro-2-quinolinyl)methoxy)phenyl)propanol

A mixture of the phenol of Step 4 (3.322 g, 12.3 mmol), K$_2$CO$_3$ (4.08 g, 29.5 mmol) and 2-(bromomethyl)-7-chloroquinoline (3.771 g, 14.7 mmol) in 60 mL of acetone was heated to reflux for 8 h. CD$_2$Cl$_2$ (100 mL) was added and the mixture was filtered through silica with EtOAc. Flash chromatography of the residue on silica using EtOAc:toluene 15:85 and 20:80 afforded 5.145 g (94%) of the title compound.

$^1$H NMR (CDCl$_3$): δ 2.02 (2H, td), 2.61 (3H, s), 2.94 (2H, m), 3.27 (1H, d, OH), 4.65 (1H, td), 5.36 (2H, s), 6.88 (1H, dd), 6.96 (1H, d), 7.08 (1H, s), 7.20–7.32 (3H, m), 7.42 (1H, dd), 7.48 (1H, d), 7.64–7.78 (3H, m), 8.07 (1H, s), 8.15 (1H, d).

Step 6: Ethyl 3-mercapto-2-methylpropanoate

At −20° C., 3N NaOH (150 mL, 450 mmol) was added dropwise to a solution of ethyl 3-(acetylthio)-2-methylpropanoate (66.47 g, 349 mmol, obtained from ethyl methacrylate as in Example 10, Step 1) in 700 mL of MeOH and the mixture was stirred at that temperature for 30 min. 25% Aq NH$_4$OAc was then added and the title thiol was extracted with EtOAc, dried over MgSO$_4$, concentrated and distilled to yield 42.52 g (82%) of the title compound as an oil; bp: 96°–98° C./15 mm Hg.

$^1$H NMR (CDCl$_3$): δ 1.21–1.36 (6H, m), 1.50 (1H, t, SH), 2.66 (2H, m), 2.81 (1H, m), 4.19 (2H, q).

Step 7: Ethyl 3-((3-(2-acetylphenyl)-1-(3-((7-chloro-2-quinolinyl)methoxy)phenyl)propyl)thio)-2-methylpropanoate At −40° C., Et$_3$N (triethylamine) (1.60 mL, 11.5 mmol) and methanesulfonyl chloride (750 μL, 9.69 mmol) were added to a solution of the alcohol of Step 5 (3.296 g, 7.39 mmol) in 74 mL of CH$_2$Cl$_2$ and the mixture was stirred at −40° C. for an hour and at −10° C. for 45 min. Saturated aq NaHCO$_3$ was then added and the mesylate was extracted with CH$_2$Cl$_2$, dried over Na$_2$SO$_4$ and concentrated. To this mesylate in 150 mL of anhydrous CH$_3$CN, ethyl 3-mercapto-2-methylpropanoate (2.20 mL, approx. 15 mmol) and Cs$_2$CO$_3$ (7.57 g, 23.2 mmol) were added and the mixture was stirred under a stream of N$_2$ for 2 h. 25% Aq NH$_4$OAc was then added and the title product was extracted with EtOAc, dried over Na$_2$SO$_4$ and purified by flash chromatography on silica with EtOAc:toluene 2.5:97.5 and 5:95. Yield 3.881 g, 91%.

$^1$H NMR (CDCl$_3$): δ 1.13 (3H, 2d, mixture of diastereomers), 1.23 (3H, 2t), 2.09 (2H, td), 2.30 (1H, dd), 2.40–2.78 (6H, m), 2.90 (1H, m), 3.81 (1H, 2t), 4.11 (2H, 2q), 5.38 (2H, s), 6.90 (1H, br d), 6.95 (1H, d), 7.07 (1H, br d), 7.14 (1H, d), 7.20–7.30 (2H, m), 7.37 (1H, dd), 7.50 (1H, dd), 7.66 (1H, d), 7.73 (1H, d), 7.76 (1H, d), 8.09 (1H, s), 8.18 (1H, d).

Step 8: 3-((3-(2-acetylphenyl)-1-(3-((7-chloro-2-quinolinyl)methoxy)phenyl)propyl)thio)-2-methylpropanoic acid A mixture of the ester of Step 7 (3.844 g, 6.67 mmol) and 1.0N NaOH (13 mL) in 55 mL of MeOH:THF 3:2 was stirred at r.t. for 24 h. 25% Aq NH$_4$OAc was then added and the mixture was acidified with AcOH. The title acid was extracted with EtOAc, dried over Na$_2$SO$_4$ and purified by flash chromatography on silica with acetone:toluene:AcOH 5:95:1. Yield 3.491 g, 95%.

$^1$H NMR (CDCl$_3$): δ 1.16 (3H, 2d, mixture of diastereomers), 2.08 (2H, td), 2.38 (1H, m), 2.57–2.78 (6H, m), 2.91 (1H, m), 3.83 (1H, 2t), 5.38 (2H, s), 6.88 (1H, d), 6.94 (1H, d), 7.07 (1H, br s), 7.12–7.30 (3H, m), 7.35 (1H, dd), 7.49 (1H, d), 7.65 (1H, d), 7.70 (1H, d), 7.75 (1H, d), 8.10 (1H, s), 8.18 (1H, d).

Step 9

To a well stirred solution of the methyl ketone of Step 8 (2.955 g, 5.39 mmol) in 100 mL of anhydrous toluene, 1.5M MeMgBr (9.0 mL, 13.5 mmol) was added dropwise at −10° C. and the suspension was stirred at 0° C. for 30 min. Saturated aq NH$_4$Cl was then added and the product was extracted with EtOAc, dried over Na$_2$SO$_4$ and purified by flash chromatography on silica using acetone:toluene:AcOH 4:96:1. The impure acid was dissolved in ether and diazomethane was added at 0° C. When the reaction was completed, AcOH was added, followed by 25% aq NH$_4$OAc. The ester was extracted with EtOAc, washed with 5% aq NaHCO$_3$, dried over Na$_2$SO$_4$ and purified by flash chromatography on silica twice: first with EtOAc:hexane 20:80, then with EtOAc:toluene 7.5:92.5. The pure ester was hydrolyzed with NaOH as in Step 8 and the sodium salt was formed as in Method A, Step 10.

EXAMPLE 2

Sodium 3-((1-(3-((7-chloro-2-quinolinyl)methoxy)phenyl)-3-(2-(1-hydroxy-1-cyclopentyl)phenyl)propyl)thio)propanoate Step 1: 2-(3-(3-(diphenyl(2-methyl-2-propyl)siloxy)phenyl)-3-hydroxypropyl) benzoic acid Using the procedure of Example 1, Method B, Step 3, but replacing 3-(2-tetrahydropyranyloxy)phenylmagnesium bromide by 3-(diphenyl(2-methyl-2-propyl)siloxy)phenylmagnesium bromide, the title compound was obtained. Yield: 90%.

$^1$H NMR (CD$_3$COCD$_3$): δ 1.09 (9H, s), 1.83 (2H, td), 2.97 (2H, m), 4.49 (1H, dd), 6.63 (1H, br d), 6.86 (1H, br s), 6.90 (1H, d), 7.05 (1H, dd), 7.24 (1H, d), 7.32 (1H, dd), 7.35–7.53 (7H, m), 7.73–7.78 (4H, m), 7.94 (1H, d).

Step 2: 4,5-dihydro-3-(3-(diphenyl(2-methyl-2-propyl)siloxy)phenyl-2-benzoxepin-1(3H)-one To the hydroxyacid of Step 1 (25.58 g, 50.09 mmol) and Et$_3$N (22 mL, 158 mmol) in 250 mL of CH$_2$Cl$_2$:CH$_3$CN 4:1 at 0° C., 2-chloro-1-methylpyridinium iodide (ground, 20.35 g, 79.7 mmol) was added and the resulting mixture was stirred at 0° C. for 2.5 h. 25% Aq NH$_4$OAc was then added and the title lactone was extracted with EtOAc, dried over Na$_2$SO$_4$ and purified by flash chromatography on silica with EtOAc:hexane 10:90 and 15:85. Yield: 23.00 g, 93%.

Step 3: 4,5-dihydro-3-(3-hydroxyphenyl)-2-benzoxepin-1(3H)-one

At 0° C., 1.0M Bu$_4$NF (tetrabutylammonium fluoride, 60 mL) was added to a solution of the lactone of Step 2 (23.00 g, 46.7 mmol) and AcOH (7.0 mL, 122 mmol) in 250 mL of anhydrous THF and the resulting mixture was stirred at 0° C. for 2 h. 25% Aq NH$_4$OAc was then added and the title phenol was extracted with EtOAc, dried over Na$_2$SO$_4$ and purified by flash chromatography on silica with EtOAc:toluene 10:90 and 15:85. Yield: 11.45 g, 96%.

Step 4: 3-(3-((7-chloro-2-quinolinyl)methoxy)phenyl)-4,5-dihydro-2-benzoxepin-1(3H)-one Using the procedure of Example 1, Method B, Step 5, the product of Step 3 was converted to the title compound. Yield: 90%.

$^1$H NMR (CD$_3$COCD$_3$/CD$_3$SOCD$_3$): δ 2.16–2.45 (2H, m), 2.86–3.10 (2H, m), 5.11 (1H, dd), 5.38 (2H, s), 7.01–7.12 (2H, m), 7.24 (1H, br s), 7.30 (1H, dd), 7.39–7.50 (2H, m), 7.57–7.70 (3H, m), 7.74 (1H, d), 8.04 (1H, s), 8.07 (1H, d), 8.47 (1H, d).

Step 5: 1-(2-(3-(3-((7-chloro-2-quinolinyl)methoxy)phenyl)-3-hydroxypropyl)phenyl)cyclopentanol To the lactone of Step 4 (1.004 g, 2.335 mmol) in 5 mL of anhydrous THF at r.t., a suspension of 0.70M 1,4-di(bromomagnesio)butane in THF (J. Org. Chem., 45, 1828 (1980); 5.3 mL, 3.7 mmol) was added dropwise and the mixture was stirred for 30 min and was quenched at 0° C. with cold 25% aq NH$_4$OAc. The title cyclopentanol was extracted with EtOAc, dried over Na$_2$SO$_4$ and purified by flash chromatography on silica using EtOAc:toluene 15:85 and 20:80. Yield: 1.006 g, 88%.

$^1$H NMR (CDCl$_3$): δ1.65–1.82 (2H, m), 1.82–2.30 (9H, m, including OH), 2.95–3.20 (3H, m, including OH), 4.63 (1H, dd), 5.34 (2H, s), 6.88 (1H, d), 6.95 (1H, d), 7.06 (1H, br s), 7.10–7.30 (4H, m), 7.38 (1H, d), 7.50 (1H, d), 7.67 (1H, d), 7.76 (1H, d), 8.06 (1H, br s), 8.14 (1H, d).

Step 6

Using the procedure of Example 1, Method B, Step 7, the benzyl alcohol of Step 5 was substituted by methyl 3-mercaptopropanoate with a yield of 50%. The ester was then hydrolyzed using the procedure of Example 1, Method B, Step 8, and the sodium salt was formed as in Example 1, Method A, Step 10.

Anal. calcd for C$_{33}$H$_{33}$ClNO$_4$SNa.1.5H$_2$O: C, 63.40; H, 5.80; N, 2.24 Found: C, 63.44; H, 5.74; N, 2.21.

EXAMPLE 3

Sodium 3-((3-(4-chloro-2-(2-hydroxy-2-propyl)-phenyl)-1-(3-((7-chloro-2-quinolinyl)methoxy)-phenyl)propyl)thio)-propanoate Using the procedure of Example 1, Method B, Steps 1 and 2,7-chlorotetralone (Can. Pat. No. 974,997) was converted to 5-chloro-2-(3-oxopropyl) benzoic acid. Using the procedure of Example 2, but substituting 1,4-di(bromomagnesio)butane and THF (as solvent) for MeMgCl and toluene in Step 5, the title compound was obtained from 5-chloro-2-(3-oxopropyl)benzoic acid.

Anal. calcd for C$_{31}$H$_{30}$Cl$_2$NO$_4$SNa.0.5H$_2$O: C, 60.49; H, 5.08; N, 2.28; S, 5.21; Na, 3.73 Found: C, 60.46; H, 4.88; N, 2.24; S, 5.37; Na, 3.69.

EXAMPLE 5

Sodium N-acetyl-2-(R)-amino-3-((1-(3-((7-chloro-2-quinolinyl)-methoxy)phenyl)-3-(2-(2-hydroxy-2-propyl)phenyl)-propyl)thio)propanoate Step 1: 2-(3-(3-((7-chloro-2-quinolinyl)methoxy)-phenyl)-3-hydroxypropyl)-α,α-dimethylbenzenemethanol Using the procedure of Example 2, Steps 1–5, but substituting 1,4-di(bromomagnesio)butane and THF (as solvent) for MeMgCl and toluene in Step 5, the title compound was prepared.

$^1$H NMR (CDCl$_3$): δ 1.67 (6H, d), 2.07 (2H, td), 2.39 (1H, s, OH), 3.00–3.25 (3H, m, containing OH), 4.65 (1H, br t), 5.35 (2H, s), 6.89 (1H, dd), 6.96 (1H, d), 7.06 (1H, s), 7.12–7.29 (4H, m), 7.47 (1H, d), 7.50 (1H, dd), 7.68 (1H, d), 7.75 (1H, d), 8.06 (1H, s), 8.15 (1H, d).

Step 2

The mesylate of the diol of Step 1 (729 mg, 1.58 mmol) was prepared using the procedure of Example 1, Method B, Step 7. To a solution of this crude mesylate and N-acetyl-L-cysteine (546 mg, 3.35 mmol) in 15 mL of anhydrous DMF at 0° C. was added 60% NaH in oil (530 mg, 13.3 mmol) and the mixture was stirred at r.t. for 2 h. 25% Aq NH$_4$OAc was then added and the solution was acidified with AcOH and extracted with EtOAc:THF 1:1. The organic layers were dried over Na$_2$SO$_4$ and evaporated. Flash chromatography of the residue on silica using MeOH:CH$_2$Cl$_2$:AcOH 2.5:97.5:1, 3.7:96.3:1 and 7.5:92.5:1 yielded first, N-acetyl-2-(R)-amino-3-((1-(3-((-7-chloro-2-quinolinyl)methoxy)-phenyl)-3-(2-(2-propenyl)phenyl)propyl)thio)propanoic acid, then, the title acid. The sodium salt of the latter was formed using the procedure of Example 1, Method B, Step 10. Yield 480 mg, 50%.

Anal. calcd for C$_{33}$H$_{34}$ClN$_2$O$_5$SNa.H$_2$O: C, 61.25; H, 5.61; N, 4.33. Found: C, 61.14; H, 5.24; N, 4.27.

EXAMPLE 6

Sodium 3-((1-(R)-(3-((7-chloro-2-quinolinyl)methoxy)phenyl)-3-(2-(2-hydroxy-2-propyl)phenyl)propyl)thio)-2-(S)-methylpropanoate Step 1: Methyl 2-(3-(3-(diphenyl(2-methyl-2-propyl)siloxy)phenyl)-3-hydroxypropyl)benzoate To the product of Example 2, Step 1 (95 g, 0.187 mol) in acetone (1 L) was added $K_2CO_3$ (55 g, 0.374 mol) and MeI (128 mL, 1.31 mol). After refluxing for 1.5 h, the reaction mixture was cooled to r.t. EtOAc (1 L) was then added to the reaction mixture and the $K_2CO_3$ was removed by filtration. The filtrate was evaporated to dryness to provide 93 g (98%) of the title ester.

$^1$H NMR ($CD_3COCD_3$): δ 1.08 (9H, s), 1.76 (2H, m), 2.86 (2H, m), 3.80 (3H, s), 4.20 (1H, d), 4.50 (1H, m), 6.66 (1H, d), 6.91 (2H, m), 7.05 (1H, t), 7.25 (1H, t), 7.30 (1H, t), 7.35–7.53 (6H, m), 7.75 (5H, m), 7.83 (1H, d).

Step 2: Methyl 2-(3-(3-(diphenyl(2-methyl-2-propyl)siloxy)phenyl)-3-oxopropyl)benzoate The alcohol of Step 1 (93 g, 0.179 mol), dissolved in $CH_2Cl_2$ (300 mL) was added to a mixture of 4A molecular sieve (94 g, milled) and PCC, (pyridinium chlorochromate, 69 g, 0.321 mol) in $CH_2Cl_2$ (1 L) at 10° C. The mixture was then allowed to warm to 20° C. for 2 h and ether (1 L) was introduced. The mixture was filtered through silica and was washed with ether (2 L) and EtOAc:hexane 1:1 (1 L). Evaporation of the filtrate and flash chromatography (10% EtOAc:hexane) of the crude mixture on silica gave the title product. Yield: 81 g, 87%.

$^1$H NMR ($CD_3COCD_3$): δ 1.16 (9H, s), 3.12 (2H, m), 3.23 (2H, m), 3.86 (3H, s), 7.08 (1H, m), 7.28 (1H, t), 7.38–7.45 (7H, m), 7.55 (1H, t), 7.80 (7H, m), 7.95 (1H, d).

Step 3: Methyl 2-(3-(3-(diphenyl(2-methyl-2-propyl)siloxy)phenyl)-3-(R)-hydroxy-propyl)benzoate At −20° C., (S)-tetrahydro-1-methyl-3,3-diphenyl-1H,3H-pyrrolo(1,2-c)(1,3,2)oxazaborole (J. Am. Chem. Soc., 104, 5551–5553 (1987), 3.82 g, 0.014 mol) was added to a solution of the ketone of Step 2 in THF (556 mL). To this mixture, 1.0M $BH_3$.THF (111 mL) was slowly added within 10 min. After 15 min, the reaction was quenched with 2M HCl (250 mL). After extraction with EtOAc, the organic phase was washed with 25% aq $NH_4OAc$ followed by saturated NaCl. The solvent was removed at reduced pressure to afford an oil which was purified by flash chromatography (20% EtOAc in hexane) to give 70 g (95%) of the title compound.

$[α]_D^{22}+10°$ (c 1.4, THF).

Step 4: α,α-dimethyl-2-(3-(3-(diphenyl(2-methyl-2-propyl)siloxy)phenyl)-3-(R)-hydroxypropyl)benzenemethanol At 0° C., 3.0M MeMgCl (90 mL, 270 mmol) was slowly added to a solution of methyl 2-(3-(3-(diphenyl(2-methyl-2-propyl)siloxy)phenyl)-3-(R)-hydroxypropyl)benzoate (Step 3, 32.0 g, 61 mmol) in 350 mL of toluene and the mixture was stirred at 0° C. for 30 min and at r.t. for 30 min. At 0° C., 25% aq $NH_4OAc$ was added and the products were extracted with EtOAc, dried over $Na_2SO_4$ and purified by flash chromatography on silica with EtOAc:toluene 5:95 and 10:90 to yield, first, the enolization product 3-(2-acetylphenyl)-1-(3-(diphenyl(2-methyl-2-propyl)siloxy)phenyl)-1-(R)-propanol, then, the title tertiary alcohol. Yield: 20.48 g, 64%.

(The enolization product can be resubjected to the Grignard reaction, using the same procedure, to give more of the title compound.)

Step 5: 2-(3-(3-((7-chloro-2-quinolinyl)methoxy)phenyl)-3-(R)-hydroxypropyl)-α,α-dimethylbenzenemethanol Using the procedure of Example 2, Step 3, the silyl ether of Step 4 was hydrolyzed to the phenol ($[α]_D+20.6°$ (c 1.85, THF)). This phenol was converted to the title compound using the procedure of Example 1, Method B, Step 5. Yield: 87%, $[α]_D+10.7°$ (c 2.02, THF).

$^1$H NMR ($CDCl_3$): δ 1.65 (6H, d), 2.07 (2H, td), 2.44 (1H, s, OH), 3.00–3.26 (3H, m, 1 OH), 4.64 (1H, t), 5.34 (2H, s), 6.88 (1H, dd), 6.95 (1H, d), 7.06 (1H, s), 7.10–7.30 (4H, m), 7.46 (1H, d), 7.50 (1H, d), 7.67 (1H, d), 7.76 (1H, d), 8.06 (1H, s), 8.15 (1H, d).

Step 6: 2-(3-(3-((7-chloro-2-quinolinyl)methoxy)phenyl)-3-(R)-(diphenyl(2-methyl-2-propyl)siloxy)propyl)-α,α-dimethylbenzenemethanol A mixture of the diol of Step 5 (24.37 g, 52.75 mmol), $Et_3N$ (22.0 mL, 158 mmol), 4-(dimethylamino)pyridine (10.96 g, 89.7 mmol) and tert-butylchlorodiphenylsilane (28.0 mL, 108 mmol) in 260 mL of $CH_2Cl_2$ was stirred at r.t. for 18 h and at reflux for 4 h. At 0° C., 25% aq $NH_4OAc$ was added and the phases were separated. The aqueous phase was extracted with EtOAc and the combined organic layers were dried over $Na_2SO_4$ and concentrated. The residue was purified twice by flash chromatography on silica with EtOAc:toluene 2.5:97.5 and 5:95 to yield 28.92 g (79%) of the title silyl ether. $[α]_D+26.5°$ (c 1.91, THF).

Step 7: 7-chloro-2-((3-(3-(2-(2-(2-tetrahydropyranyloxy)-2-propyl)phenyl)-1-(R)-diphenyl(2-methyl-2-propyl)siloxy)propyl)phenoxy)methyl)quinoline The tertiary alcohol of Step 6 (28.88 g, 41.23 mmol), dihydropyran (12.5 mL, 137 mmol) and triphenylphosphine hydrobromide (725 mg, 2.11 mmol) were mixed together in 200 mL of $CH_2Cl_2$ and stirred for 2 days. The solvent was then evaporated and the title product was purified by a flash chromatography on silica using toluene and EtOAc:toluene 1.5:98.5 and 2.5:97.5. Yield: 29.90 g, 92%.

$^1$H NMR ($CDCl_3$): δ 1.05 (9H,s), 1.25–1.46 (9H,m), 1.55–1.77 (3H, m), 1.95 (2H, td), 2.32–2.62 (1H, m), 2.94–3.22 (1H, m), 3.30 (1H, m), 3.86 (1H, m), 4.23 (1H, t), 4.78 (1H, t), 5.34 (2H, s), 6.80–6.90 (2H, m), 6.90–7.55 (15H, m), 7.63–7.78 (4H, m), 8.09 (1H, s), 8.15 (1H, d).

Step 8: 1-(R)-(3-((7-chloro-2-quinolinyl)methoxy)phenyl)-3-(2-(2-(2-tetrahydropyranyloxy)-2-propyl)phenyl)propanol To a solution of the silyl ether of Step 7 (29.89 g, 38.11 mmol) in 130 mL of anhydrous THF, a 1.0M solution of $Bu_4NF$ in THF (100 mL) was added and the resulting solution was kept at 8° C. for 15 h and then stirred at r.t. for 2 h. AT 0° C., 25% aq $NH_4OAc$ was added and the title alcohol was extracted with EtOAc, dried over $Na_2SO_4$ and purified by flash chromatography on silica with EtOAc:toluene 10:90, 15:85 and 20:80. Yield: 17.51 g, 84%.

$[α]_D+7.35°$ (c 1.98, THF).

$^1$H NMR ($CDCl_3$): δ 1.38–1.90 (12H, m), 190–2.24 (2H, m), 2.88–3.50 (4H, m, 1OH), 4.00 (1H, m), 4.53 (1H, m), 4.80 (1H, m), 5.37 (2H, s), 6.90 (1H, m), 7.01 (1H, m), 7.07–7.36 (6H, m), 7.50 (1H, dd), 7.69 (1H, dd), 7.75 (1H, d), 8.08 (1H, s), 8.16 (1H, d).

Step 9: 1-(S)-(3-((7-chloro-2-quinolinyl)methoxy)-phenyl)-3-(2-(2-(2-tetrahydropyranyloxy)-2-propyl)-phenyl)propanol At 0° C., diethyl azodicarboxylate (7.6 mL, 48.3 mmol) was added dropwise to a solution of the alcohol of Step 8 (17.47 g, 31.97 mmol), triphenylphosphine (12.60 g, 48.04 mmol) and R-(—)-α-methoxyphenylacetic acid (8.07 g, 48.6 mmol) in 320 mL of anhydrous THF. The mixture was stirred at 0° C. for 30 min and the solvents were evaporated. Flash chromatography of the residue on silica using EtOAc:toluene 2.5:97.5, 5:95 and 7.5:92.5 afforded 21.84 g (98%) of the inverted alcohol as the mandelate ester. $[\alpha]_D - 6.02°$ (c 1.99, THF). This ester was hydrolyzed to the title alcohol as in Example 1, Method B, Step 8.

$[\alpha]_D - 8.95°$ (c 2.23, THF).

$^1$H NMR (CDCl$_3$) identical to isomer (Step 8).

Step 10 3-((1-(R)-(3-((7-chloro-2-quinolinyl)methoxy)phenyl)-3-(2-(2-(2-tetrahydropyranyloxy)-2-propyl)-phenyl)propyl)thio)-2-(S)-methylpropanoic acid Using the procedure of Example 5, Step 2, but replacing N-acetyl-L-cysteine for 3-mercapto-2-(S)-methylpropanoic acid (prepared from commercially available 3-(acetylthio)-2-(S)-methylpropanoic acid as in Example 7, Step 4), the title acid was prepared from the benzylic alcohol of Step 9. Yield: 70%. $^1$H NMR (CDCl$_3$): δ 1.20 (3H, d), 1.33–1.50 (7H, br s), 1.55–1.80 (5H, m), 2.12 (2H, m), 2.35 (1H, m), 1.97–3.40 (5H, m), 3.87 (2H, m), 4.33 (1H, m), 5.37 (2H, s), 6.88 (1H, d), 6.97 (1H, d), 7.04–7.34 (6H, m), 7.50 (1H, d), 7.69 (1H, d), 7.75 (1H, d), 8.10 (1H, s), 8.17 (1H, d).

Step 11

A mixture of the acid of Step 10 (3.254 g, 5.019 mmol) and pyridinium p-toluenesulfonate (500 mg, 1.99 mmol) in 30 mL of MeOH was stirred at r.t. for 16 h and then evaporated to dryness. Flash chromatography of the residue on silica with EtOAc:hexane:AcOH 25:75:1 and 30:70:1 afforded 2.453 g (87%) of the tertiary alcohol ($[\alpha]_D + 83.8°$ (c 1.42, THF)).

The sodium salt was then formed as in Example 1, Method A, Step 10. $[\alpha]_D + 95.2°$ (c 1.04, THF).

EXAMPLE 7

Sodium 3-((1-(R)-(3-((7-chloro-2-quinolinyl)methoxy)phenyl)-3-(2-(2-hydroxy-2-propyl)phenyl)propyl)thio)-2-(R)-methylpropanoate Step 1: Methyl 3-(methanesulfonyloxy)-2-(S)-methylpropanoate A solution of methyl 3-hydroxy-2-(S)-methylpropanoate (35 g, 295 mmol) in 830 mL of CH$_2$Cl$_2$, under N$_2$ atmosphere, was cooled to −60° C. With rapid stirring, methanesulfonyl chloride (24 mL, 310 mmol) was added, followed by Et$_3$N (50 mL, 354 mmol) over 90 s. As the addition ended, a heavy white precipitate formed which stopped the magnetic stirring. The cold bath was removed and the reaction allowed to reach r.t. The reaction mixture was poured into aq 25% NH$_4$OAc. After separation, the organic phase was dried over MgSO$_4$ and evaporated to give the title compound as a colorless oil (59.1 g, 102%).

$^1$H NMR (CDCl$_3$): δ 1.28 (3H,d), 2.93 (1H, m), 3.05 (3H, s), 3.74 (3H, s), 4.33 (2H, ddd).

$[\alpha]_D + 10.9°$ (c 2.0, CHCl$_3$).

Step 2: Methyl 3-acetylthio-2-(R)-methylpropanoate

Under inert atmosphere, 31.6 mL (442 mmol) of thiolacetic acid was cooled to −10° C. Et$_3$N (41.4 mL), 295 mmol) was added dropwise over ½ h to yield a light yellow solution. The mixture was allowed to warm up to 10° C. and the mesylate from Step 1 was added. After 5 min., the cold bath was removed. After ½ h stirring, the mixture had reached approx. 55° C., and was deep orange. It was cooled to r.t. and stirred for 36 h. The mixture was poured into aq 25% NH$_4$OAc and extracted twice with EtOAc. The organics were washed with 5% aq NH$_4$OAc, dried over Na$_2$SO$_4$ and the solvent evaporated. The residue was distilled to yield the title compound as a yellow oil: b.p. 64°–67° C./0.3 mmHg; yield: 43.17 g, 83%.

$^1$H NMR (CDCl$_3$): δ 1.31 (3H, d), 2.30 (3H, s), 2.67 (1H, m), 3.05 (2H, m), 3.72 (3H, s).

$[\alpha]_D + 51°$ (c 2.0, EtOH).

$[\alpha]_D + 49.6°$ (c 2.0, MeOH).

Step 3: 3-acetylthio-2-(R)-methylpropanoic acid

A solution of LiI (58.8 g, 438 mmol) and 38.6 g (219 mmol) of the ester from Step 3, under inert atmosphere, was heated to 125° C. for 16 h. The black solution was cooled and diluted with 600 mL EtOAc. This mixture was washed with aq 15% NaHSO$_4$ (400 mL) containing 1% Na$_2$SO$_3$. The aqueous phase was reextracted 4 times with 600 mL EtOAc, the organic phases were dried over Na$_2$SO$_4$, and the solvent was evaporated. The residue was distilled to yield the title compound as a yellow oil: b.p. 97°–104° C./0.06 mmHg; yield: 21.42 g, 60%.

$^1$H NMR (CDCl$_3$): δ 1.31 (3H, d), 2.38 (3H, s), 2.75 (1H, m), 3.10 (2H, m), 10.5 (1H, br s).

$[\alpha]_D 41.7°$ (c 1.0, EtOH).

Step 4: 3-mercapto-2-(R)-methylpropanoic acid

A suspension of K$_2$CO$_3$ (7.5 g, 55 mmol) in 50 mL of MeOH was degassed by bubbling N$_2$ in it for 15 min. It was then cooled to −5° C., and NaBH$_4$ (38 mg, 1 mmol) was added. After 5 min, the thiolester from Step 3 (4 g, 25 mmol) was added. The cold bath was removed. When the reaction reached r.t., glacial AcOH (7.5 mL, 125 mmol) was added slowly, and the reaction mixture was poured into a mixture of aq 10% HCl (25 mL) and brine (25 mL). Extraction with 2×50 mL CH$_2$Cl$_2$ followed by washing of the organic phase with HCl 10% (10mL), brine (10 mL), drying over Na$_2$SO$_4$ and evaporation yielded a yellow residue. Kugelrohr distillation at 100° C./15 mm Hg yielded the title compound as a colorless oil.

$^1$H NMR (CDCl$_3$): δ 1.30 (3H, d), 1.58 (1H, t), 2.8 (3H, m), 10.3 (1H, very br s).

$[\alpha]_D + 26.5°$ (c 2.0, MeOH).

(For the enantiomeric compound, Chem. Pharm. Bull. 30, 3139 (1982) reported $[\alpha]_D - 27.6°$ (c 2.0, MeOH)).

Step 5: 3-((1-(R)-(3-((7-chloro-2-quinolinyl)methoxy)phenyl)-3-(2-(2-(2-tetrahydropyranyloxy)-2-propyl)-phenyl)propyl)thio)-2-(R)-methylpropanoic acid Using the procedure of Example 5, Step 2, but substituting 3-mercapto-2-(R)-methylpropanoic acid for N-acetyl-L-cysteine, the title compound was prepared from the benzylic alcohol of Example 6, Step 9.

$^1$H NMR (CD$_3$COCD$_3$): δ 1.08 (3H, d), 1.36 (6H, m), 1.53–1.70 (8H, m), 2.08 (1H, m), 2.33 (1H, dd), 2.58 (2H, m), 2.91 (1H, t), 3.25 (1H, m), 3.83 (1H, m), 4.03 (1H, m), 4.41 (1H, m), 5.38 (2H, s), 6.93–7.33 (8H, m), 7.58 (1H, dd), 7.75 (1H, d), 8.00 (2H, m), 8.41 (1H, d).

Step 6

Using the procedure of Example 6, Step 11, the title compound was obtained from the tetrahydropyranyl ether of Step 1.

[α]$_D^{22}$ +75.8° (c 0.86, THF).

$^1$H NMR (CD$_3$COCD$_3$): δ 1.03 (3H, d), 1.41 and 1.53 (6H, 2s), 1.95 (1H, m), 2.30 (3H, m), 2.53 (1H, dt), 2.83 (1H, m), 3.11 (1H, m), 3.91 (1H, dd), 5.38 (2H, s), 6.86–7.08 (5H, m), 7.15 (1H, s), 7.23 (1H, t), 7.30 (1H, m), 7.55 (1H, dd), 7.72 (1H, d), 8.00 (2H, m), 8.38 (1H, d).

Anal. calcd for C$_{32}$H$_{33}$ClNO$_4$SNa.H$_2$O: C, 63.61; H, 5.84; N, 2.31. Found: C, 63.76; H, 5.69; N, 2.26.

EXAMPLE 8

Sodium 3-((1-(S)-(3-((7-chloro-2-quinolinyl)methoxy)phenyl)-3-(2-(2-hydroxy-2-propyl)phenyl)propyl)thio)-2-(S)-methylpropanoate Step 1: 3-((1-(S)-(3-((7-chloro-2-quinolinyl)methoxy)-phenyl)-3-(2-(2-(2-tetrahydropyranyloxy)-2-propyl)-phenyl)propyl)thio-2-(S)-methylpropanoic acid Using the procedure of Example 5, Step 2, but substituting 3-mercapto-2-(S)-methylpropanoate for N-acetyl-L-cysteine the title compound was prepared from the benzylic alcohol of Example 6, Step 8.

$^1$H NMR (CD$_3$COCD$_3$): δ 1.08 (3H, d), 1.40 (6H, m), 1.50–1.70 (8H, m), 2.11 (1H, m), 2.36 (1H, dd), 2.58 (2H, m), 2.85 (1H, t), 3.26 (1H, m), 3.71 (1H, m), 4.03 (1H, m), 4.38 (1H, m), 5.30 (2H, s), 6.93–7.33 (8H, m), 7.51 (1H, dd), 7.66 (1H, d), 8.03 (2H, m), 8.35 (1H, d).

Step 2

Using the procedure of Example 6, Step 11, the title compound was obtained from the tetrahydropyranyl ether of Step 1.

[α]$_D^{22}$ −77.8° (c 0.74, THF).

$^1$H NMR (CD$_3$COCD$_3$): δ 1.03 (3H, d), 1.40 and 1.53 (6H, 2s), 1.91 (1H, m), 2.36 (3H, m), 2.53 (1H, dt), 2.85 (1H, m), 3.11 (1H, m), 3.91 (1H, dd), 5.33 (2H, s), 6.83–7.03 (5H, m), 7.11 (1H, s), 7.20 (1H, t), 7.28 (1H, m), 7.53 (1H, dd), 7.70 (1H, d), 7.91 (1H, d), 8.00 (1H, br s), 8.30 (1H, d).

Anal. calcd for C$_{32}$H$_{33}$ClNO$_4$SNa.H$_2$O: C, 63.61; H, 5.84; N, 2.32. Found: C, 63.64; H, 5.67; N, 2.28.

EXAMPLE 9

Sodium 3-((1-(S)-(3-((7-chloro-2-quinolinyl)methoxy)phenyl)-3-(2-(2-hydroxy-2-propyl)phenyl)propyl)thio)-2-(R)-methylpropanoate Step 1: 3-((1-(S)-(3-((7-chloro-2-quinolinyl)-methoxy)phenyl)-3-(2-(2-(2-tetrahydropyranyloxy)-2-propyl)-phenyl)propyl)thio-2-(R)-methylpropanoic acid Using the procedure of Example 5, Step 2, but substituting 3-mercapto-2-(R)-methylpropanoate for N-acetyl-L-cysteine, the title compound was prepared from the benzylic alcohol of Example 6, Step 8.

$^1$H NMR (CD$_3$COCD$_3$): δ 1.11 (3H, d), 1.38 (6H, m), 1.51–1.70 (8H, m), 2.11 (1H, m), 2.36 (1H, m), 2.53 (1H, m), 2.66 (1H, dd), 2.93 (1H, t), 3.28 (1H, m), 3.83 (1H, m), 4.03 (1H, m), 4.41 (1H, m), 5.41 (2H, s), 6.93–7.33 (8H, m), 7.58 (1H, dd), 7.76 (1H, d), 8.00 (2H, m), 8.41 (1H, d).

Step 2

Using the procedure of Example 6, Step 11, the title compound was obtained from the tetrahydropyranyl ether of Step 1.

[α]$_D^{22}$ −99.5° (c 0.63, THF).

$^1$H NMR (CD$_3$COCD$_3$): δ 1.03 (3H, d), 1.43 and 1.50 (6H, 2s), 1.95 (1H, m), 2.27 (3H, m), 2.58–3.10 (3H, m), 3.88 (1H, br t), 5.33 (2H, s), 6.86–7.03 (5H, m), 7.15 (1H, s), 7.20 (1H, t), 7.33 (1H, m), 7.53 (1H, dd), 7.71 (1H, d), 7.95 (1H, d), 8.00 (1H, s), 8.33 (1H, d).

Anal. calcd for C$_{32}$H$_{33}$ClNO$_4$SNa.H$_2$O: C, 63.61; H, 5.84; N, 2.32. Found: C, 63.71; H, 5.70; N, 2.29.

EXAMPLE 10

Sodium 3-((1-(3-((7-chloro-2-quinolinyl)methoxy)-phenyl)-3-(2-(2-hydroxy-2-propyl)phenyl)propyl)thio)-2-ethylpropanoate Step 1: Ethyl 2-((acetylthio)methyl)butanoate Ethyl 2-ethylpropenoate (5 g, 39 mmol) was diluted with 5.6 mL (78 mmol) of thiolacetic acid and stirred at 65° C. for 36 h. The mixture was then diluted with ether, washed with water and the organic phase was dried with Na$_2$SO$_4$. Evaporation to dryness yielded the title material as an orange oil which was used as such for the next step.

$^1$H NMR (CDCl$_3$): δ 0.96 (3H, t), 1.28 (3H, t), 1.70 (3H, m), 2.35 (3H, s), 3.10 (2H, m), 4.18 (2H, q).

Step 2: Ethyl 2-(mercaptomethyl)butanoate

To a solution of the thioester of Step 1 (5.00 g, 24.5 mmol) in MeOH (15 mL) at 0° C., under nitrogen, was added K$_2$CO$_3$ (9.67 g, 73.5 mmol). The resulting mixture was stirred at 0° C. for a half hour, and then AcOH (8.82 g, 147 mmol) and 25% aq NH$_4$OAc were added. The title compound was extracted with EtOAc, dried over Na$_2$SO$_4$ and purified by distillation on a Kugelrohr apparatus (200° C., 760 mm Hg). Yield: 1.700 g, 45%.

$^1$H NMR (CD$_3$COCD$_3$): δ 0.86 (3H, t), 1.25 (3H, t), 1.65 (2H, quintet), 1.78 (1H, t), 2.45 (1H, quintet), 2.68 (2H, m), 4.15 (2H, q).

Step 3: Ethyl 3-((1-(3-((7-chloro-2-quinolinyl)methoxy)phenyl)-3-(2-(2-hydroxy-2-propyl)phenyl)-propyl)thio)-2-ethylpropanoate Starting from the diol of Example 5, Step 1, and using the procedure of Example 1, Method B, Step 7, but substituting the thiol of Step 2 for ethyl 2-(mercaptomethyl)butanoate, the title compound was prepared. Yield: 64%.

$^1$H NMR (CD$_3$COCD$_3$): δ 0.75 (3H, 2t), 1.21 (3H, m), 1.46 (2H, quintet), 1.51 (6H, s) 2.08 (2H, m), 2.25–2.63 (3H, m), 2.78 (1H, m), 3.08 (1H, m), 3.91 (1H, m), 4.08 (2H, m), 5.40 (2H, s), 6.92–7.10 (5H, m), 7.16 (1H, m), 7.25 (1H, t), 7.38 (1H, m), 7.58 (1H, dd), 7.75 (1H, dd), 8.00 (2H, m), 8.41 (1H, d).

Step 4

To a solution of the ester of Step 3 (540 mg, 0.89 mmol) in MeOH (20 mL) was added H$_2$O (4 mL). To the resulting suspension, K$_2$CO$_3$ was then added, followed by 10N NaOH (120 μL). The mixture was then heated at 45° C. overnight. The reaction was then neutralized by the addition of 25% aq NH$_4$OAc and the title compound was extracted with EtOAc and dried on Na$_2$SO$_4$. After evaporation at reduced pressure and flash chromatography on silicic acid (20% acetone in toluene), the pure acid was obtained (300 mg, 59%). The sodium salt was then formed as in Example 1, Method A, Step 10.

Anal. calcd for C$_{33}$H$_{35}$ClNO$_4$SNa.2.5H$_2$O: C, 61.46; H, 6.20; N, 2.17. Found: C, 61.42; H, 6.03; N, 2.12.

EXAMPLE 11

Sodium
3-((1-(3-((7-chloro-2-quinolinyl)methoxy)phenyl)-3-(2-(2-hydroxy-2-propyl)phenyl)propyl)thio)propanoate Starting from the diol of Example 5, Step 1, and using the procedures of Example 10, Steps 3 and 4, but substituting methyl 3-mercaptopropanoate for the thiol of Step 2, the title compound was prepared.

Anal. calcd for $C_{31}H_{31}ClNO_4SNa.1.5H_2O$: C, 62.18; H, 5.07; N, 2.33; Found: C, 62.29; H, 5.52; N, 2.31.

EXAMPLE 12

Sodium
3-((-1(3-((7-chloro-2-quinolinyl)methoxy)phenyl)-3-(2-(2-hydroxy-2-propyl)phenyl)propyl)thio)-2,2-dimethylpropanoate Step 1: Methyl 2,2-dimethyl-3-mercaptopropanoate Using the procedure described in Chem. Abstr. 58, 11490c, the title thiol was prepared from methyl 3-bromo-2,2-dimethylpropanoate (J. Am. Chem. Soc., 77, 3016 (1955)).

Step 2

Starting from the diol of Example 5, Step 1, and using the procedure of Example 10, Step 3 and 4, but substituting methyl 2,2-dimethyl-3-mercaptopropanoate for the thiol of Step 2, the title compound was prepared.

Anal. calcd for $C_{33}H_{35}ClNO_4SNa.2H_2O$: C, 62.36; H, 6.13; N, 2.20. Found: C, 62,58; H, 5.98; N, 2.15.

EXAMPLE 30

3-((1-(3-((7-chloro-2-quinolinyl)methoxy)phenyl)-3-(2-(1-hydroxy-2,2,2-trifluoroethyl)phenyl)propyl)thio)propanoic acid Anal. calcd for $C_{30}H_{27}ClF_3SNO_4S$: C, 61.07; H, 4.61; N, 2.37; S, 5.43. Found: C, 61.27; H, 4.69; N, 2.40; S, 5.44.

EXAMPLE 62

Sodium
3-((1-(S)-(3-((7-chloro-2-quinolinyl)methoxyphenyl)-3-(2-(2-hydroxy-2-propyl)phenyl)propyl)thio)-2(S)-ethylpropanoate Anal. calcd for $C_{33}H_{35}ClNO_4SNa.2H_2O$: C, 62.31; H, 6.13; N, 2.20 Found: C, 62.40; H, 6.25; N, 2.10

EXAMPLE 64

Sodium
3-((1(S)-(3-((7-chloro-2-quinolinyl)methoxy)phenyl)-3-(2-(2-hydroxy-2-propyl)phenyl)propyl)thio)-2-((4-chlorophenyl)methyl)propanoate Anal. calcd for $C_{38}H_{36}Cl_2NO_4SNa.3H_2O$: C, 60.80; H, 5.64; N, 1.87 Found: C, 60.91; H, 5.08; N, 1.88

EXAMPLE 65

2-(((1(S)-(3-((7-chloro-2-quinolinyl)methoxy)phenyl)-3-(2-(2-hydroxy-2-propyl)phenyl)propyl)thio)methyl)-4-pentenoic acid $^1$H NMR (CDCl$_3$): δ 1.58 (6H, s), 2.05–2.20 (2H, m), 2.20–2.40 (2H, m), 2.40–2.70 (3H, m), 2.70–2.85 (1H, m), 3.00–3.15 (1H, m), 3.90 (1H, q), 4.95–5.10 (2H, m), 5.40 (2H, s), 5.55–5.75 (1H, m), 6.88 (1H, dd), 6.95 (1H, dd), 7.05–7.18 (4H, m), 7.20 (1H, d), 7.35 (1H, d), 7.50 (1H, dd), 7.70 (1H, dd), 7.75 (1H, dd), 8.10 (1H, br s), 8.15 (1H, d).

Anal. calcd for $C_{34}H_{35}ClNO_4SNa.2H_2O$ (sodium salt of the title compound): C, 63.00; H, 6.06; N, 2.16 Found: C, 63.25; H, 6.05; N, 2.22

EXAMPLE 67

Sodium
3-((1(S)-(3-((7-chloro-2-quinolinyl)methoxy)phenyl)-3-(2-(2-hydroxy-2-propyl)phenyl)propyl)thio)-2-(methylthiomethyl)propanoate Anal. calcd for $C_{33}H_{35}ClNO_4S_2Na.1.5H_2O$: C, 60.07; H, 5.81; N, 2.12 Found: C, 60.02; H, 6.01; N, 2.10

EXAMPLE 68

Sodium
3-((1(S)-(3-((7-chloro-2-quinolinyl)methoxy)phenyl)-3-(2-(2-hydroxy-2-propyl)phenyl)propyl)thio)-2-cyclopropylpropanoate Anal. calcd for $C_{34}H_{35}ClNO_4SNa$: C, 66.71; H, 5.76; N, 2.29 Found: C, 66.74; H, 5.74; N, 2.05

EXAMPLE 69

Sodium
2-(((1(S)-(3-((7-chloro-2-quinolinyl)methoxy)phenyl)-3-(2-(2-hydroxy-2-propyl)phenyl)propyl)thio)methyl)-4-pentynoate $[α]_D$ −80° (c 1.00, EtOH).

Anal. calcd for $C_{34}H_{33}ClNO_4SNa.2H_2O$: C, 63.20; H, 5.77; N, 2.17 Found: C, 63.13; H, 5.25; N, 2.14

EXAMPLE 70

Sodium
3-((1(S)-(3-((7-chloro-2-quinolinyl)methoxy)phenyl)-3-(2-(2-hydroxy-2-propyl)phenyl)propyl)thio)-2-(phenylmethyl)propanoate $[α]_D$ −72° (c 1.0, EtOH).

EXAMPLE 71

Sodium
3-((1-(3-((7-chloro-2-quinolinyl)methoxy)phenyl)-3-(2-(1-hydroxyethyl)phenyl)propyl)thio)-2-methylpropanoate Anal. calcd for $C_{31}H_{31}ClNO_4SNa.H_2O$: C, 63.10; H, 5.64; N, 2.37 Found: C, 63.15; H, 5.74; N, 2.34

EXAMPLE 72

Sodium
3-((1(S)-(3-((7-chloro-2-quinolinyl)methoxy)phenyl)-3-(2-(2-hydroxy-2-propyl)phenyl)propyl)thio)-2-phenylpropanoate Anal. calcd for $C_{37}H_{35}ClNO_4SNa.1.5H_2O$: C, 65.82; H, 5.67; N, 2.07 Found: C, 65.64; H, 5.68; N, 2.03

EXAMPLE 131

3-((1(R)-(3-((7-chloro-2-quinolinyl)methoxy)phenyl)-3-(2-(2-hydroxy-2-propyl)phenyl)-propyl)thio)-3-methylbutanoic acid Step 1: 3-Benzylthio-3-methylbutanoic acid A solution of 3,3-dimethylacrylic acid (7 g, 70 mmol) and benzyl mercaptan (8.9 mL, 7.5 mmol) in piperidine (70 mL) was heated to reflux for 2 days. Piperidine was then evaporated and the product was partitioned between EtOAc and an aqueous solution of 1N HCl. The organic phase was washed with brine and dried over MgSO$_4$. After evaporation of the solvent the product was distilled with a Kugelrohr apparatus under high vacuum (1 mmHg) to give 15.5 g of the title compound (99% yield).

$^1$H NMR (CDCl$_3$) δ 1.50 (6H, s), 2.67 (2H, s), 3.82 (2H, s), 7.30 (5H, m).

Step 2: 3-Mercapto-3-methylbutanoic acid

Approximately 300 mL of ammonia was condensed in a three neck flask maintained at −70° C. Then, 8.3 g of Na (0.35 mol) was added in small pieces with very vigorous stirring. The 3-benzylthio-3-methylbutanoic acid from Step 1 (15.5 g, 69 mmol) dissolved in THF (50 mL) was added dropwise at −78° C. The deep blue solution was stirred for 1 h at −78° C. and solid NH$_4$Cl and an aqueous solution of NH$_4$Cl was added until the blue color vanished. The solution was then warmed to room temperature and ammonia was evaporated with a stream of nitrogen. The reaction mixture was then acidified with HOAc, extracted with EtOAc, washed with brine and dried over MgSO$_4$. The solvent was evaporated and the residual oil was used without further purification.

$^1$H NMR (CDCl$_3$) δ 1.50 (6H, s), 2.38 (1H, s) and 2.72 (2H, s).

Step 3:

The title compound was prepared using the enantiomer of the alcohol of Example 6, Step 8, and 3-mercapto-3-methylbutanoic acid, following Method J.

What is claimed is:

1. A compound of the formula:

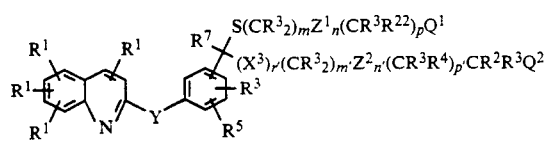

wherein:
$R^1$ is H, halogen, —CF$_3$, —CN, —NO$_2$ or N$_3$;
$R^2$ is lower alkyl, lower alkenyl, lower alkynyl, —CF$_3$, —CH$_2$F, —CHF$_2$, CH$_2$CF$_3$, substituted or unsubstituted phenyl, substituted or unsubstituted benzyl, substituted or unsubstituted 2-phenethyl, or two $R^2$ groups joined to the same carbon may form a ring of up to 8 members containing 0–2 heteroatoms chosen from O, S, and N;
$R^3$ is H or $R^2$;
$CR^3R^{22}$ may be the radical of a standard amino acid;
$R^4$ is halogen, —NO$_2$, —CN, —OR$^3$, —SR$^3$, NR$^3$R$^3$, NR$^3$C(O)R$^7$ or R$^3$;
$R^5$ is H, halogen, —NO$_2$, —N$_3$, —CN, —SR$^2$, —NR$^3$R$^3$, —OR$^3$, lower alkyl, or —C(O)R$^3$;
$R^6$ is —(CH$_2$)$_s$—C(R$^7$R$^7$)—(CH$_2$)$_s$—R$^8$ or —CH$_2$C(O)NR$^{12}$R$^{12}$;
$R^7$ is H or C$_1$-C$_4$ alkyl;
$R^8$ is
  A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or
  B) the radical W-R$^9$;
$R^9$ contains up to 20 carbon atoms and is (1) an alkyl group, or (2) an alkylcarbonyl group of an organic acyclic or monocyclic carboxylic acid containing 0–1 heteroatom in the ring;
$R^{10}$ is —SR$^{11}$, —OR$^{12}$, or —NR$^{12}$R$^{12}$;
$R^{11}$ is lower alkyl, —C(O)R$^{14}$, unsubstituted phenyl, or unsubstituted benzyl;
$R^{12}$ is H, R$^{11}$, or two R$^{12}$ groups joined to the same N may form a ring of 5 or 6 members containing 1–2 heteroatoms chosen from O, S, and N;
$R^{13}$ is lower alkyl, lower alkenyl, lower alkynyl, —CF$_3$ or substituted or unsubstituted phenyl, benzyl, or 2-phenethyl;
$R^{14}$ is H or R$^{13}$;
$R^{16}$ is H, C$_1$-C$_4$ alkyl, or OH;
$R^{17}$ is lower alkyl, lower alkenyl, lower alkynyl, or substituted or unsubstituted phenyl, benzyl, or 2-phenethyl;
$R^{18}$ is lower alkyl, lower alkenyl, lower alkynyl, —CF$_3$ or substituted or unsubstituted phenyl, benzyl, or 2-phenethyl;
$R^{19}$ is lower alkyl, lower alkenyl, lower alkynyl, —CF$_3$ or substituted or unsubstituted phenyl, benzyl, or 2-phenethyl;
$R^{20}$ is H, C$_1$-C$_4$ alkyl, substituted or unsubstituted phenyl, benzyl, phenethyl, or pyridinyl or two R$^{20}$ groups joined to the same N may form a saturated ring of 5 or 6 members containing 1–2 heteroatoms chosen from O, S, and N;
$R^{21}$ is H or R$^{17}$;
$R^{22}$ is R$^4$, CHR$^7$OR$^3$, or CHR$^7$SR$^2$;
m and m' are independently 0–8;
n and n' are independently 0 or 1,
p and p' are independently 0–8;
m+n+p is 1–10 when r is 1 and X$^2$ is O, S, S(O), or S(O)$_2$;
m+n+p is 0–10 when r is 1 and X$^2$ is CR$^3$R$^{16}$;
m+n+p is 0–10 when r is 0;
m'+n'+p' is 0–10;
r and r' are independently 0 or 1;
s is 0–3;
$Q^1$ is —C(O)OR$^3$, —1H (or 2H)-tetrazol-5-yl, —C(O)OR$^6$, —C(O)NHS(O)$_2$R$^{13}$, —CN, —C(O)NR$^{12}$R$^{12}$, —NR$^{21}$S(O)$_2$R$^{13}$, —NR$^{12}$C(O)NR$^{12}$R$^{12}$, —NR$^{21}$C(O)R$^{18}$, —OC(O)NR$^{12}$R$^{12}$, —C(O)R$^{19}$, —S(O)R$^{18}$, —S(O)$_2$R$^{18}$, —S(O)$_2$NR$^{12}$R$^{12}$, —NO$_2$, —NR$^{21}$C(O)OR$^{17}$, —C(NR$^{12}$R$^{12}$)=NR$^{12}$, —C(R$^{13}$)=NOH; or if Q$^1$ is —C(O)OH and R$^{22}$ is —OH, —SH, —CHR$^7$OH or —NHR$^3$, then Q$^1$ and R$^{22}$ and the carbons through which they are attached may form a heterocyclic ring by loss of water;
$Q^2$ is OH or NR$^{20}$R$^{20}$;
W is O, S, or NR$^3$;
$X^1$ is O, S, S(O), S(O)$_2$, or NR$^3$;
$X^3$ is O, S, S(O), S(O)$_2$, or CR$^3$R$^{16}$;
Y is —CR$^3$R$^3$—X$^1$—, —X$^1$—CR$^3$R$^3$—, —CR$^3$R$^3$—X$^1$—CR$^3$R$^3$—, —NR$^3$C(O)—, or —C(O)NR$^3$—;
$Z^1$ and $Z^2$ are independently —HET(—R$^3$—R$^5$)—;
HET is the diradical of a benzene, a pyridine, a furan, or a thiophene;
and the pharmaceutically acceptable salts thereof.

2. A compound of claim 1 wherein:
$R^1$ is H, halogen, CF$_3$ or —CN;
$R^2$ is C$_1$-C$_4$ alkyl, —CF$_3$, —CHF$_2$, —CH$_2$F, or two R$^2$ groups joined to the same carbon may form a ring of up to 6 carbons;
$R^3$ is H or R$^2$;
$CR^3R^{22}$ may be the radical of a standard amino acid;
$R^4$ is —OR$^3$, —SR$^3$, NR$^3$R$^3$, NHC(O)CH$_3$, or R$^3$;
$R^5$ is H or halogen;
$R^6$ is —(CH$_2$)$_s$—C(R$^7$R$^7$)—(CH$_2$)$_s$—R$^8$ or —CH$_2$C(O)NR$^{12}$R$^{12}$;
$R^7$ is H or C$_1$-C$_4$ alkyl;

R⁸ is
A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or
B) the radical W-R⁹;
R⁹ contains up to 20 carbon atoms and is (1) an alkyl group or (2) an alkylcarbonyl group;
$R^{10}$ is —SR¹¹, —OR¹², or —NR¹²R¹²;
R¹¹ is lower alkyl, —C(O)R¹⁴, unsubstituted phenyl, or unsubstituted benzyl;
R¹² is H, R¹¹, or two R¹² groups joined to the same N may form a ring of 5 or 6 members containing 1-2 heteroatoms chosen from O, S, and N;
R¹³ is lower alkyl, —CF₃, or unsubstituted phenyl, benzyl, or 2-phenethyl;
R¹⁴ is H or R¹³;
R¹⁶ is H, C₁-C₄ alkyl, or OH;
R²² is R⁴, —CH₂OR³, or —CH₂SR²;
m and m' are independently 0-4;
n and n' are independently 0 or 1;
p and p' are independently 0-4;
m+n+p is 1-9 when r is 1 and X² is O or S;
m+n+p is 0-9 when r is 1 and X² is CR³R¹⁶;
m+n+p is 0-9 when r is 0;
m'+n'+p' is 1-9;
r and r' are independently 0 or 1;
s is 0-3;
Q¹ is —C(O)OR³, 1H(or 2H)-tetrazol-5-yl, —C(O)OR⁶, —C(O)NHS(O)₂R¹³, —C(O)NR¹²R¹², —NHS(O)₂R¹³; or if Q¹ is C(O)OH and R²² is —OH, —SH, —CH₂OH or —NHR³ then Q¹ and R²² and the carbons through which they are attached may form a heterocyclic ring by loss of water;
Q² is OH;
W is O, S, or NH;
X¹ is O, S, or NR³;
X³ is O, S, or CR³R¹⁶;
Y is —CR³R³—X¹—;
Z¹ and Z² are independently —HET(—R³—R⁵)—;

HET is the diradical of a benzene, pyridine, furan, or thiophene;
and the pharmaceutically acceptable salts thereof.

3. A compound of claim 1 wherein the R²² α to Q¹ is lower alkyl, CF₃ or substituted or unsubstituted phenyl.

4. A compound of claim 1 of the Formula Ia:

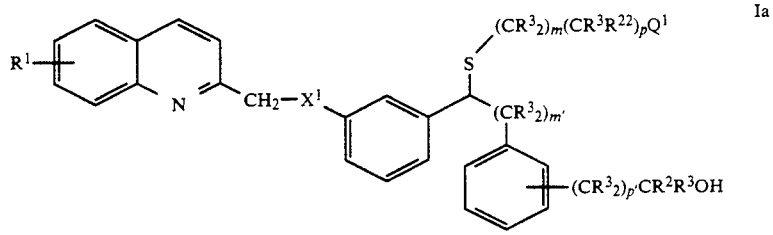

wherein:
R¹ is H, halogen, CF₃, or CN;
R²² is R³, —CH₂OR³, or —CH₂SR²;
Q¹ is —C(O)OH, 1H (or 2H)-tetrazol-5-yl, —C(O)NHS(O)₂R¹³, —C(O)NR¹²R¹², or —NHS(O)₂R¹³;
m' is 2 or 3;
p' is 0 or 1;
m+p is 1-5;
and the pharmaceutically acceptable salts thereof.

5. A compound of claim 4 wherein m' is 0.
6. A compound of claim 4 wherein X¹ is 0.
7. A compound of claim 6 wherein the carbon α to Q¹ is lower alkyl-substituted.
8. A compound of claim 1 of the Formula Ib:

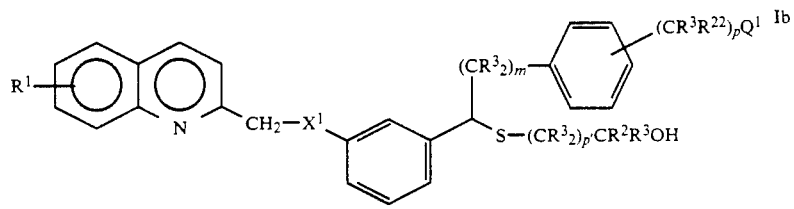

wherein:
R¹ is H, halogen, CF₃, or CN;
R²² is R³, —CH₂OR³, or —CH₂SR²;
Q¹ is —C(O)OH, 1H (or 2H)-tetrazol-5-yl, —C(O)NHS(O)₂R¹³, —C(O)NR¹²R¹², or —NHS(O)₂R¹³;
m is 0, 2 or 3;
p is 0 or 1;
p' is 1-4;
m+p is 0-4;
and the pharmaceutically acceptable salts thereof.

9. A compound of claim 8 wherein X¹ is 0.
10. A compound of claim 1 of Formula I':

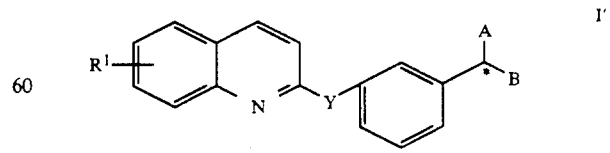

wherein the substituents are as follows:

TABLE I

| COMPOUND | * | R¹ | Y | A | B |
|---|---|---|---|---|---|
| 1 | RS | 7-Cl | CH₂O | SCH₂CHMeCO₂H | (CH₂)₂(1,2-phe)CMe₂OH |

TABLE I-continued

| COMPOUND | * | R¹ | Y | A | B |
|---|---|---|---|---|---|
| 2 | RS | 7-Cl | $CH_2O$ | $S(CH_2)_2CO_2H$ | $(CH_2)_2(1,2\text{-phe})C((CH_2))_4OH$ |
| 3 | RS | 7-Cl | $CH_2O$ | $S(CH_2)_2CO_2H$ | $(CH_2)_2(4\text{-Cl-1,2-phe})CMe_2OH$ |
| 4 | RS | 7-Cl | $CH_2O$ | $SCH_2CHMeCO_2H$ | $(1,3\text{-phe})CMe_2OH$ |
| 5 | RS | 7-Cl | $CH_2O$ | $SCH_2(R)CH(NHAc)CO_2H$ | $(CH_2)_2(1,2\text{-phe})CMe_2OH$ |
| 6 | R | 7-Cl | $CH_2O$ | $SCH_2(S)CHMeCO_2H$ | $(CH_2)_2(1,2\text{-phe})CMe_2OH$ |
| 7 | R | 7-Cl | $CH_2O$ | $SCH_{12}(R)(CHMeCO_2H$ | $(CH_2)_2(1,2\text{-phe})CMe_2OH$ |
| 8 | S | 7-Cl | $CH_2O$ | $SCH_2(S)CHMeCO_2H$ | $(CH_2)_2(1,2\text{-phe})CMe_2OH$ |
| 9 | S | 7-Cl | $CH_2O$ | $SCH_2(R)CHMeCO_2H$ | $(CH_2)_2(1,2\text{-phe})CMe_2OH$ |
| 10 | RS | 7-Cl | $CH_2O$ | $SCH_2CHEtCO_2H$ | $(CH_2)_2(1,2\text{-phe})CMe_2OH$ |
| 11 | RS | 7-Cl | $CH_2O$ | $S(CH_2)_2CO_2H$ | $(CH_2)_2(1,2\text{-phe})CMe_2OH$ |
| 12 | RS | 7-Cl | $CH_2O$ | $SCH_2CMe_2CO_2H$ | $(CH_2)_2(1,2\text{-phe})CMe_2OH$ |
| 13 | RS | 7-Cl | $CH_2S$ | $SCH_2CHMeCO_2H$ | $(CH_2)_2(1,2\text{-phe})CMe_2OH$ |
| 14 | RS | 7-Cl | $CH_2O$ | $S(CH_2)_2CO_2H$ | $(CH_2)_2(1,2\text{-phe})CMe_2OH$ |
| 15 | RS | 7-Br | $CH_2O$ | $SCH_2CHMeCO_2H$ | $(CH_2)_2(1,2\text{-phe})CMe_2OH$ |
| 16 | S | 7-Br | $CH_2O$ | $SCH_2(S)CHMeCO_2H$ | $(CH_2)_2(1,2\text{-phe})CMe_2OH$ |
| 17 | R | 7-Br | $CH_2O$ | $SCH_2(S)CHMeCO_2H$ | $(CH_2)_2(1,2\text{-phe})CMe_2OH$ |
| 18 | S | 7-Cl | $CH_2O$ | $S(CH_2)_2CO_2H$ | $S(CH_2)_2CMe_2OH$ |
| 19 | S | 7-Cl | $CH_2O$ | $SCH_2CHMeCO_2H$ | $(CH_2)_2(1,3\text{-phe})C(CF_3)_2OH$ |
| 20 | RS | 7-Cl | $CH_2O$ | $SCH_2CHMeCO_2H$ | $(CH_2)_2(1,2\text{-phe})C(CF_3)_2OH$ |
| 21 | RS | 7-Cl | $CH_2O$ | $SCH_2CHMeCO_2H$ | $(CH_2)_2(1,3\text{-phe})CMe_2OH$ |
| 22 | RS | 7-Cl | $CH_2O$ | $SCH_2CHEtCO_2H$ | $SCH_2CMe_2CMe_2OH$ |
| 23 | RS | 7-Cl | $CH_2O$ | $SCH_2CHMeCMe_2OH$ | $(CH_2)_2(1,2\text{-phe})CO_2H$ |
| 24 | RS | 7-Cl | $CH_2O$ | $SCH_2CHMeCMe_2OH$ | $(CH_2)_2(1,2\text{-phe})CONH_2$ |
| 25 | RS | 7-Cl | $CH_2O$ | $SCH_2CHMeCO_2H$ | $SCH_2(1,2\text{-phe})CMe_2OH$ |
| 26 | RS | 7-Cl | $CH_2O$ | $SCH_2CHMeCO_2H$ | $(CH_2)_2(1,4\text{-phe})CMe_2OH$ |
| 27 | RS | 7-Cl | $CH_2S$ | $SCH_2CHEtCO_2H$ | $(CH_2)_2(1,3\text{-phe})CMe_2OH$ |
| 28 | RS | 7-Cl | $CH_2O$ | $SCH_2CH(OMe)CO_2H$ | $(CH_2)_2(1,2\text{-phe})CMe_2OH$ |
| 29 | S | 7-Cl | $CH_2O$ | $SCH_2(R)CHEtCO_2H$ | $(CH_2)_2(1,2\text{-phe})CMe_2OH$ |
| 30 | RS | 7-Cl | $CH_2O$ | $S(CH_2)_2CO_2H$ | $(CH_2)_2(1,2\text{-phe})CH(CF_3)OH$ |
| 31 | RS | 7-Cl | $CH_2OCH_2$ | $SCH_2CHEtCO_2H$ | $(CH_2)_2(1,2\text{-phe})CMe_2OH$ |
| 32 | RS | 7-F | $CH_2O$ | $SCH_2CH(n\text{-Pr})CO_2H$ | $(CH_2)_2(1,2\text{-phe})CMe_2OH$ |
| 33 | RS | 7-Cl | $CH_2O$ | $SCH_2CMe_2CO_2H$ | $(CH_2)_2(1,2\text{-phe})CMe_2OH$ |
| 34 | RS | 7-Cl | $CH_2O$ | $SCH_2CHEtCO_2H$ | $(CH_2)_2(1,3\text{-phe})CMe_2OH$ |
| 35 | RS | 7-$CF_3$ | $CH_2O$ | $SCH_2CHEtCO_2H$ | $(CH_2)_2(1,2\text{-phe})C(CF_3)_2OH$ |
| 36 | RS | H | $CH_2O$ | $SCH_2CHEtCO_2H$ | $(CH_2)_2(1,2\text{-phe})CMe_2OH$ |
| 37 | RS | H | $CH_2O$ | $SCH_2CHEtCO_2H$ | $(1,3\text{-phe})CMe_2OH$ |
| 38 | RS | 7-Cl | $CH_2O$ | $SCH_2CHEtCO_2H$ | $(CH_2)_2(4\text{-Br-1,2-phe})CMe_2OH$ |
| 39 | RS | 7-Cl | $CH_2O$ | $SCH_2CHEtCO_2H$ | $(CH_2)_2(1,2\text{-phe})CMeEtOH$ |
| 40 | RS | 7-Cl | $CH_2O$ | $SCH_2CHEtCO_2H$ | $(CH_2)_2(1,2\text{-phe})CEt_2OH$ |
| 41 | RS | 7-Cl | $CH_2O$ | $SCH_2CHEtCO_2H$ | $(CH_2)_2(1,2\text{-phe})C((CH_2)_3)OH$ |
| 42 | RS | 7-Cl | $CH_2O$ | $SCH_2CHMeCO_2H$ | $(CH_2)_2(1,2\text{-phe})CMe_2NH_2$ |
| 43 | RS | 7-CL | $CH_2O$ | $SCH_2CHEtCO_2H$ | $(CH_2)_2(1,2\text{-phe})CHMeNHMe$ |
| 44 | RS | 7-Cl | $CH_2O$ | $SCH_2CHEtCO_2H$ | $(CH_2)_2(1,2\text{-phe})CHMeNMe_2$ |
| 45 | RS | 7-Cl | $CH_2O$ | $SCH_2CHEtCO_2H$ | $(CH_2)_2(2,5\text{-fur})CMe_2OH$ |
| 46 | RS | 7-Cl | $CH_2O$ | $SCH_2CHEtCO_2H$ | $(CH_2)_2(2,6\text{-pye})CMe_2OH$ |
| 47 | RS | 7-Cl | $CH_2O$ | $SCH_2CHEtCO_2H$ | $(CH_2)_2(4,2\text{-pye})CMe_2OH$ |
| 48 | RS | 7-Cl | $CH_2O$ | $SCH_2CHEtCO_2H$ | $(CH_2)_2(2,5\text{-thio})CMe_2OH$ |
| 49 | RS | 7-Cl | $CH_2O$ | $SCH_2CHEtCO_2H$ | $(CH_2)_2(3,2\text{-pye})CMe_2OH$ |
| 50 | RS | 7-CN | $CH_2O$ | $SCH_2CHEtCO_2H$ | $(CH_2)_2(1,4\text{-phe})CMe_2OH$ |
| 51 | RS | 7-Cl | $CH_2O$ | $SCH_2CHEtCO_2H$ | $(CH_2)_2(1,4\text{-phe})CMe_2OH$ |
| 52 | RS | 7-Cl | $CH_2O$ | $SCH_2CHMeCONHS(O)_2Me$ | $(CH_2)_2(1,2\text{-phe})CMe_2OH$ |
| 53 | RS | 7-Cl | $CH_2O$ | $SCH_2CHMeCONH_2$ | $(CH_2)_2(1,2\text{-phe})CMe_2OH$ |
| 54 | RS | 7-Cl | $CH_2O$ | $SCH_2CHMeCONHMe$ | $(CH_2)_2(1,2\text{-phe})CMe_2OH$ |
| 55 | RS | 7-Cl | $CH_2O$ | $SCH_2CHMeTz$ | $(CH_2)_2(1,2\text{-phe})CMe_2OH$ |
| 56 | RS | 7-Cl | $CH_2O$ | $SCH_2CHEtTz$ | $(CH_2)_2(1,2\text{-phe})CEt_2OH$ |
| 57 | RS | 7-Cl | $CH_2O$ | $SCH_2CHEtCONHS(O)_2CF_3$ | $(CH_2)_2(1,2\text{-phe})CMe_2OH$ |
| 58 | RS | 7-Cl | $CH_2O$ | $SCH_2CHMeNO_2$ | $(CH_2)_2(1,2\text{-phe})CMe_2OH$ |
| 59 | RS | 7-Cl | $CH_2O$ | $S(CH_2)_2CONHS(O)_2Ph$ | $(CH_2)_2(1,2\text{-phe})CMe_2OH$ |
| 60 | R | 7-Cl | $CH_2O$ | $SCH_2(S)CHEtCO_2H$ | $(CH_2)_2(1,2\text{-phe})C(n\text{-Pr})_2OH$ |
| 61 | RS | 7-Cl | $CH_2O$ | $S(CH_2)_2CO_2H$ | $(CH_2)_2(1,2\text{-phe})CH_2CMe_2OH$ |
| 62 | S | 7-Cl | $CH_2O$ | $SCH_2(S)CHEtCO_2H$ | $(CH_2)_2(1,2\text{-phe})CMe_2OH$ |
| 63 | RS | 7-Cl | $CH_2O$ | $SCH_2CH(n\text{-Pr})CO_2H$ | $(CH_2)_2(1,2\text{-phe})CMe_2NH_2$ |
| 64 | S | 7-Cl | $CH_2O$ | $SCH_2CH(CH_2(4\text{-ClPh}))CO_2H$ | $(CH_2)_2(1,2\text{-phe})CMe_2OH$ |
| 65 | S | 7-Cl | $CH_2O$ | $SCH_2CH(CH_2CH=CH_2)CO_2H$ | $(CH_2)_2(1,2\text{-phe})CMe_2OH$ |
| 66 | S | 7-Cl | $CH_2S(O)_2$ | $SCH_2CHEtCO_2H$ | $(CH_2)_2(1,2\text{-phe})CHMeOH$ |
| 67 | S | 7-Cl | $CH_2O$ | $SCH_2CH(CH_2SMe)CO_2H$ | $(CH_2)_2(1,2\text{-phe})CMe_2OH$ |
| 68 | S | 7-Cl | $CH_2O$ | $SCH_2CH(c\text{-Pr})CO_2H$ | $(CH_2)_2(1,2\text{-phe})CMe_2OH$ |
| 69 | S | 7-Cl | $CH_2O$ | $SCH_2CH(CH_2C\equiv CH)CO_2H$ | $(CH_2)_2(1,2\text{-phe})CMe_2OH$ |
| 70 | S | 7-Cl | $CH_2O$ | $SCH_2CH(CH_2Ph)CO_2H$ | $(CH_2)_2(1,2\text{-phe})CMe_2OH$ |
| 71 | RS | 7-Cl | $CH_2O$ | $SCH_2CHMeCO_2H$ | $(CH_2)_2(1,2\text{-phe})CHMeOH$ |
| 72 | S | 7-Cl | $CH_2O$ | $SCH_2CHPhCO_2H$ | $(CH_2)_2(1,2\text{-phe})CMe_2OH$ |
| 73 | S | 7-Cl | $CH_2S$ | $SCH_2CHMeCO_2H$ | $(CH_2)_2(1,2\text{-phe})CH_2CMe_2OH$ |
| 74 | S | 7-Cl | $CH_2O$ | $SCH_2CHEtCO_2H$ | $(CH_2)_2(1,2\text{-phe})CH_2CMe_2OH$ |
| 75 | S | 7-Cl | $CH_2O$ | $SCH_2CH(n\text{-Pr})CO_2H$ | $(CH_2)_2(1,2\text{-phe})CMe_2OH$ |
| 76 | RS | 7-Cl | $CH_2O$ | $SCH_2CHEtCO_2H$ | $(1,2\text{-phe})CMe_2OH$ |
| 77 | S | 7-Cl | $CH_2O$ | $SCH_2CHEtCO_2H$ | $(CH_2)_2(1,2\text{-phe})C(CH_2OCH_2)OH$ |
| 78 | RS | 7-Cl | $CH_2O$ | $S(CH_2)_2CMe_2OH$ | $(CH_2)_2(1,2\text{-phe})CO_2H$ |
| 79 | RS | 7-Cl | $CH_2O$ | $S(CH_2)_2CMe_2OH$ | $(1,3\text{-phe})CO_2H$ |
| 80 | RS | 7-Cl | $CH_2O$ | $S(CH_2)_2CO_2H$ | $CH_2CHOH(1,4\text{-phe})CN$ |
| 81 | RS | 7-Cl | $CH_2O$ | $S(CH_2)_2CO_2H$ | $CH_2CHOH(1,3\text{-phe})CN_4H$ |
| 82 | RS | 7-Cl | $CH_2O$ | $S(CH_2)_2CO_2H$ | $CH_2CHOH(1,4\text{-phe})CN_4H$ |

TABLE I-continued

| COMPOUND | * | R$^1$ | Y | A | B |
|---|---|---|---|---|---|
| 83 | S | 7-Cl | CH$_2$O | S(CH$_2$)$_2$CO$_2$H | (CH$_2$)$_2$(1,2-phe)CMe$_2$OH |
| 84 | S | 7-Cl | CH$_2$O | SCH$_2$CHCF$_3$CO$_2$H | (CH$_2$)$_2$(1,2-phe)CMe$_2$OH |
| 85 | S | 7-Cl | CH$_2$O | S(CH$_2$)$_3$CO$_2$H | (CH$_2$)$_2$(1,2-phe)CMe$_2$OH |
| 86 | S | 7-Cl | CH$_2$O | S(CH$_2$)$_2$CHMeCO$_2$H | (CH$_2$)$_2$1,2-phe)CMe$_2$OH |
| 87 | S | 7-Cl | CH$_2$O | S(O)$_2$CH$_2$(S)CHEtCO$_2$H | (CH$_2$)$_2$(1,2-phe)CMe$_2$OH |
| 88 | S | 7-Cl | CH$_2$O | SCH$_2$CH(CH$_2$OMe)CO$_2$H | (CH$_2$)$_2$(1,2-phe)CMe$_2$OH |
| 89 | S | 7-Cl | CH$_2$O | S(CH$_2$)$_2$CMe$_2$OH | (CH$_2$)$_2$(1,2-phe)CO$_2$H |
| 90 | R | 7-Cl | CH$_2$O | S(CH$_2$)$_2$CMe$_2$OH | (CH$_2$)$_2$(1,2-phe)CO$_2$H |
| 91 | S | 7-Cl | CH$_2$O | SCH$_2$(S)CHEtCO$_2$H | (CH$_2$)$_2$(1,3-phe)CMe$_2$OH |
| 92 | S | 7-Cl | CH$_2$O | SCH$_2$CHEtCO$_2$H | (CH$_2$)$_2$(1,3-phe)(1,1-c-Bu)OH |
| 93 | S | 7-Cl | CH$_2$O | S(CH$_2$)$_2$CMe$_2$OH | (CH$_2$)$_3$(1,2-phe)COOH |
| 94 | R | 7-Cl | CH$_2$O | S(CH$_2$)$_2$CO$_2$H | S(CH$_2$)$_2$(1-1-c-Pen)OH |
| 95 | S | 7-Cl | CH$_2$O | SCH$_2$CH(CH$_2$CF$_3$)CO$_2$H | (CH$_2$)$_2$(1,2-phe)CMe$_2$OH |
| 96 | S | 7-Cl | CH$_2$O | S(CH$_2$)$_2$CMe$_2$OH | (CH$_2$)$_2$(4-Cl-1,2-phe)CO$_2$H |
| 97 | R | 7-Cl | CH$_2$O | SCH$_2$(S)CHEtCONHS(O)$_2$Me | (CH$_2$)$_2$(1,2-phe)CMe$_2$OH |
| 98 | S | 7-Cl | CH$_2$O | S(CH$_2$)$_2$CMeOH | (CH$_2$)$_2$(1,3-phe)CMe$_2$CO$_2$H |
| 99 | S | 7-Cl | CH$_2$O | S(CH$_2$)$_2$CMeOH | (CH$_2$)$_2$(1,3-phe)CHMeCO$_2$H |
| 100 | S | 7-Cl | CH$_2$O | S(CH$_2$)$_3$CMe$_2$OH | (CH$_2$)$_2$(1,2-phe)CO$_2$H |
| 101 | S | 7-Cl | CH$_2$O | SCH$_2$(S)CHEtCO$_2$H | (CH$_2$)$_2$(1,4-phe)CMe$_2$OH |
| 102 | RS | 7-Cl | CH$_2$O | S(CH$_2$)$_2$CMe$_2$OH | (CH$_2$)$_2$(1,3-phe)CN$_4$H |
| 103 | S | 7-Cl | CH$_2$O | S(CH$_2$)$_3$CMe$_2$OH | (CH$_2$)$_2$(1,2-phe)CHMeCO$_2$H |
| 104 | S | 7-Cl | CH$_2$O | S(CH$_2$)$_3$CMe$_2$OH | (CH$_2$)$_2$(1,2-phe)CHMeCONHS(O)$_2$CH$_3$ |
| 105 | S | 7-Cl | CH$_2$O | S(CH$_2$)$_2$CMe$_2$OH | (CH$_2$)$_3$(1,2-phe)CO$_2$H |
| 106 | R | 7-Cl | CH$_2$O | S(O)$_2$CH$_2$(S)CHEtCO$_2$H | (CH$_2$)$_2$(1,2-phe)CMe$_2$OH |
| 107 | S | 7-Cl | CH$_2$O | S(CH$_2$)$_2$CMe$_2$OH | (CH$_2$)$_2$(4-Cl-1,2-phe)CHMeCO$_2$H |
| 108 | S | 7-Cl | CH$_2$O | SCH$_2$(S)CHMeCO$_2$H | (CH$_2$)$_2$(1,2-phe)CH$_2$CMe$_2$OH |
| 109 | S | 7-Cl | CH$_2$O | S(CH$_2$)$_3$CMe$_2$OH | (CH$_2$)$_2$(4-Cl-1,2-phe)CO$_2$H |
| 110 | R | 7-Cl | CH$_2$O | S(CH$_2$)$_2$CMe$_2$OH | (CH$_2$)$_2$(4-Cl-1,2-phe)CO$_2$H |
| 111 | S | 7-Cl | CH$_2$O | S(CH$_2$)$_3$CMe$_2$OH | (CH$_2$)$_2$(1,2-phe)CMe$_2$CO$_2$H |
| 112 | S | 7-Cl | CH$_2$O | S(CH$_2$)$_2$CMe$_2$OH | (CH$_2$)$_3$(R)CHMe$_2$CO$_2$H |
| 113 | S | 7-Cl | CH$_2$O | S(CH$_2$)$_3$CEt$_2$OH | (CH$_2$)$_2$(1,2-phe)CO$_2$H |
| 114 | S | 7-Cl | CH$_2$O | S(CH$_2$)$_3$CEt$_2$OH | (CH$_2$)$_2$(1,2-phe)CHMeCO$_2$H |
| 115 | R | 7-Cl | CH$_2$O | SCHMeCH$_2$CO$_2$H | (CH$_2$)$_2$(1,2-phe)CMe$_2$OH |
| 116 | S | 7-Cl | CH$_2$O | S(CH$_2$)$_3$CMe$_2$OH | (CH$_2$)$_2$(1,2-phe)CHEtCO$_2$H |
| 117 | S | 7-Cl | CH$_2$O | S(CH$_2$)$_3$CMe$_2$OH | (CH$_2$)$_2$(1,2-phe)CH(n-Pr)CO$_2$H |
| 118 | S | 7-Cl | CH$_2$O | S(CH$_2$)$_3$CMe$_2$OH | (CH$_2$)$_2$(1,2-phe)CH(i-Pr)CO$_2$H |
| 119 | R | 7-Cl | CH$_2$O | SCH$_2$MeCHMeCO$_2$H | (CH$_2$)$_2$(1,2-phe)CMe$_2$OH |
| 120 | R | 7-Cl | CH$_2$O | S(CH$_2$)$_2$CMe$_2$OH | (CH$_2$)$_3$(R)CHMeCO$_2$H |
| 121 | R | 7-Cl | CH$_2$O | SCH$_2$(S)CHMeCN$_4$H | (CH$_2$)$_2$(1,2-phe)CMe$_2$OH |
| 122 | S | 7-Cl | CH$_2$O | SCH$_2$(S)CHMeCO$_2$H | (CH$_2$)$_2$(3-OH-1,4-phe)CHMeOH |
| 123 | S | 7-Cl | CH$_2$O | S(CH$_2$)$_3$CMeOH | (CH$_2$)$_2$(1,2-phe)CHMeCO$_2$H |
| 124 | R | 7-Cl | CH$_2$O | S(S)CHMeCH$_2$CO$_2$H | (CH$_2$)$_2$(1,2-phe)CMe$_2$OH |
| 125 | R | 7-Cl | CH$_2$O | S(R)CHMeCH$_2$CO$_2$H | (CH$_2$)$_2$(1,2-phe)CMe$_2$OH |
| 126 | R | 7-Cl | CH$_2$O | S(S)CHMe(S)CHMeCO$_2$H | (CH$_2$)$_2$(1,2-phe)CMe$_2$OH |
| 127 | R | 7-Cl | CH$_2$O | S(R)CHMe(R)CHMeCO$_2$H | (CH$_2$)$_2$(1,2-phe)CMe$_2$OH |
| 128 | R | 7-Cl | CH$_2$O | SCHEtCH$_2$CO$_2$H | (CH$_2$)$_2$(1,2-phe)CMe$_2$OH |
| 129 | S | 7-Cl | CH$_2$O | S(CH$_2$)$_3$CHMeOH | (CH$_2$)$_2$(1,2-phe)CHEtCO$_2$H |
| 130 | S | 7-Cl | CH$_2$O | SCH$_2$(S)CHMeCO$_2$H | (CH$_2$)$_2$(1,2-phe)CH(OH)CH$_2$(OH)Ph |
| 131 | R | 7-Cl | CH$_2$O | SCMe$_2$CH$_2$CO$_2$H | (CH$_2$)$_2$(1,2-phe)CMe$_2$OH |
| 132 | R | 7-Cl | CH$_2$O | SCH$_2$CHMeCH$_2$CO$_2$H | (CH$_2$)(1,2-phe)CMe$_2$OH |
| 133 | R | 7-Cl | CH$_2$S | SCH$_2$(1,1-c-Pr)CH$_2$CO$_2$H | (CH$_2$)$_2$(1,2-phe)CMe$_2$OH |
| 134 | S | 7-Cl | CH$_2$SO$_2$ | SCH$_2$(1,1-c-Pr)CH$_2$CO$_2$H | (CH$_2$)$_2$(1,2-phe)CO$_2$H |
| 135 | S | 7-Cl | CH$_2$O | S(CH$_2$)$_3$CMe$_2$OH | (CH$_2$)$_2$(1,2-phe)(R)CHEtCO$_2$H |
| 136 | S | 7-Cl | CH$_2$O | S(CH$_2$)$_3$CMe$_2$OH | (CH$_2$)$_2$(1,2-phe)(S)CHEtCO$_2$H |
| 137 | S | 7-Cl | CH$_2$O | S(CH$_2$)$_3$CMe$_2$OH | (CH$_2$)$_2$(4-Cl-1,2-phe)CHEtCO$_2$H |
| 138 | S | 7-Cl | CH$_2$O | S(CH$_2$)$_3$CMe$_2$OH | (CH$_2$)$_2$(1,2-phe)CEt$_2$CO$_2$H |
| 139 | S | 7-Cl | CH$_2$O | S(CH$_2$)$_3$CMe$_2$OH | (CH$_2$)$_2$(1,2-phe)CH$_2$CO$_2$H |
| 140 | S | 7-Cl | CH$_2$O | S(CH$_2$)$_3$CMe$_2$OH | (CH$_2$)$_2$(1,2-phe)CH(OH)CO$_2$H |
| 141 | S | 7-Cl | CH$_2$S | SCH$_2$Me$_2$CH$_2$CO$_2$H | (CH$_2$)$_2$(1,2-phe)CHEtCO$_2$H |
| 142 | S | 7-Cl | CH$_2$O | S(CH$_2$)$_3$CMe$_2$OH | (CH$_2$)$_2$CHMeCH$_2$CO$_2$H |
| 143 | R | 7-Cl | CH$_2$O | SCH$_2$CMe$_2$CH$_2$CO$_2$H | (CH$_2$)$_2$(1,2-phe)CMe$_2$OH |
| 144 | S | 7-Cl | CH$_2$O | S(CH$_2$)$_4$CMe$_2$OH | (CH$_2$)$_2$(1,2-phe)CHEtCO$_2$H |
| 145 | S | 7-F | CH$_2$O | SCH$_2$CMe$_2$CH$_2$CO$_2$H | (CH$_2$)$_2$(1,2-phe)CO$_2$H |
| 146 | S | 7-Br | CH$_2$O | SCH$_2$CMe$_2$CH$_2$CO$_2$H | (CH$_2$)$_2$(1,2-phe)CO$_2$H |
| 147 | S | 7-I | CH$_2$O | SCH$_2$(1,1-c-Pr)CH$_2$CO$_2$H | (CH$_2$)$_2$(1,2-phe)CHEtCO$_2$H |
| 148 | S | 7-CF$_3$ | CH$_2$O | SCH$_2$(1,1-c-Bu)CH$_2$CO$_2$H | (CH$_2$)$_2$(1,2-phe)CHMeCO$_2$H |
| 149 | S | 7-CN | CH$_2$O | SCH$_2$Me$_2$CH$_2$CO$_2$H | (CH$_2$)$_2$(1,2-phe)CHEtCO$_2$H |
| 150 | S | 7-NO$_2$ | CH$_2$O | SCH$_2$(1,1-c-Pr)CH$_2$CO$_2$H | (CH$_2$)$_2$(1,2-phe)CO$_2$H |
| 151 | R | 7-N$_3$ | CH$_2$O | SCH$_2$(1,1-c-Pr)CH$_2$CO$_2$H | (CH$_2$)$_2$(1,2-phe)CMe$_2$OH |
| 152 | RS | 7-Cl | CH$_2$O | S(CH$_2$)$_2$CMe$_2$OH | (CH$_2$)$_2$CMe$_2$CH$_2$CO$_2$H |
| 153 | R | 7-Cl | CH$_2$O | S(1,2-phe)CH$_2$CO$_2$H | (CH$_2$)$_2$(1,2-phe)CMe$_2$OH |
| 154 | R | 7-Cl | CH$_2$O | S(CH$_2$)$_3$CMe$_2$OH | (CH$_2$)$_2$(1,2-phe)CHEtCO$_2$H |
| 155 | S | 7-Cl | CH$_2$O | S(CH$_2$)$_2$CMe$_2$OH | (CH$_2$)$_2$(1,2-phe)CHEtCO$_2$H |
| 156 | S | 7-Cl | CH$_2$O | S(CH$_2$)$_3$CMe(4-Cl—Ph)OH | (CH$_2$)$_2$(1,2-phe)CHEtCO$_2$H |
| 157 | R | 7-Cl | CH$_2$O | SCH$_2$(1,2-phe)CMe$_2$OH | (CH$_2$)$_2$CMe$_2$CH$_2$CO$_2$H |
| 158 | R | 7-Cl | CH$_2$O | SCH$_2$(1,1-c-Pr)CH$_2$CO$_2$H | (CH$_2$)$_2$(1,2-phe)CMe$_2$OH |
| 159 | R | 7-Cl | CH$_2$O |  | (CH$_2$)$_2$(1,2-phe)CMe$_2$OH |
| 160 | R | 7-Cl | CH$_2$O | SCH$_2$CMe$_2$CHMeCO$_2$H | (CH$_2$)$_2$(1,2-phe)CMe$_2$OH |
| 161 | S | 7-Cl | CH$_2$O | SCH$_2$(1,2-phe)CMe$_2$OH | (CH$_2$)$_2$CMe$_2$CH$_2$CO$_2$H |
| 162 | R | 7-Cl | CH$_2$O | SCHMeCMe$_2$CH$_2$CO$_2$H | (CH$_2$)$_2$(1,2-phe)CMe$_2$OH |
| 163 | R | 7-Cl | CH$_2$O | S(1,1-c-Pr)CH$_2$CO$_2$H | (CH$_2$)$_2$(1,2-phe)CMe$_2$OH |

TABLE I-continued

| COMPOUND | * | R¹ | Y | A | B |
| --- | --- | --- | --- | --- | --- |
| 164 | R | 7-Cl | $CH_2O$ | $S(1,1-c-Pr)CHMeCO_2H$ | $(CH_2)_2(1,2-phe)CMe_2OH$ |
| 165 | R | 7-Cl | $CH_2O$ | $S(1,1-c-Pr)CH_2CO_2H$ | $(CH_2)_2(1,3-phe)CMe_2OH$ |
| 166 | R | 7-Cl | $CH_2O$ | $S(1,1-c-Pr)CH_2CO_2H$ | $(CH_2)_2(1,2-phe)(1,1-c-Bu)OH$ |
| 167 | R | 7-Cl | $CH_2O$ | $S(1,1-c-Pr)CH_2CO_2H$ | $(CH_2)_2(1,3-phe)(1,1-c-Bu)OH$ |
| 168 | R | 7-Cl | $CH_2O$ | $SCH_2(1,1-c-Pr)CH_2CO_2H$ | $(CH_2)_2(1,3-phe)CMe_2OH$ |
| 169 | R | 7-Cl | 1 & 2 | $SCH_2(1,1-c-Pr)CH_2CO_2H$ | $(CH_2)_2(1,2-phe)CMe_2OH$ |
| 170 | R | 7-Cl | $OCH_2$ | $S(1,1-c-Pr)CH_2CO_2H$ | $(CH_2)_2(1,2-phe)CMe_2OH$ |
| 171 | R | 7-F | 1 & 2 | $S(1,1-c-Pr)CH_2CO_2H$ | $(CH_2)_2(1,2-phe)CMe_2OH$ |
| 172 | R | 6,7-$F_2$ | $CH_2O$ | $S(1,1-c-Pr)CH_2CO_2H$ | $(CH_2)_2(1,2-phe)CMe_2OH$ |

11. A pharmaceutical composition comprising a therapeutically effective amount of a compound of claim 1 and a pharmaceutically acceptable carrier.

12. The pharmaceutical composition of claim 11 additionally comprising an effective amount of a second active ingredient selected from the group consisting of non-steroidal anti-inflammatory drugs; peripheral analgesic agents; cyclooxygenase inhibitors; leukotriene antagonists; leukotriene bisynthesis inhibitors; $H_2$-receptor antagonists; antihistaminic agents; prostaglandin antagonists; thromboxane antagonists; thromboxane synthetase inhibitors; and ACE antagonists.

13. A pharmaceutical composition according to claim 12, wherein the second active ingredient is a non-steroidal anti-inflammatory drug.

14. A pharmaceutical composition of claim 13, wherein the weight ratio of said compound of claim 1 to said second active ingredient ranges from about 1000:1 to 1:1000.

15. A method of preventing the synthesis, the action, or the release of SRS-A or leukotrienes in a mammal which comprises administering to said mammal an effective amount of a compound of claim 1.

16. The method of claim 15 wherein the mammal is man.

17. A method of treating asthma in a mammal comprising administering to a mammal in need of such treatment a therapeutically effective amount of a compound of claim 1.

18. A method of treating inflammatory diseases of the eye in a mammal which comprises administering to a mammal in need of such treatment a therapeutically effective amount of a compound of claim 1.

19. The method of claim 18 wherein the mammal is man.

* * * * *